(12) United States Patent
Lee et al.

(10) Patent No.: US 11,365,215 B2
(45) Date of Patent: Jun. 21, 2022

(54) METHOD FOR PREVENTING, IMPROVING, OR TREATING INFLAMMATORY BOWEL DISEASE

(71) Applicants: Research & Business Foundation Sungkyunkwan University, Gyeonggi-do (KR); Korea Research Institute of Chemical Technology, Daejeon (KR)

(72) Inventors: Kwangho Lee, Daejeon (KR); Sang Dal Rhee, Daejeon (KR); Gildon Choi, Daejeon (KR); Imran Ali, Daejeon (KR); Chong Hak Chae, Daejeon (KR); Moon Kook Jeon, Daejeon (KR); Seok Hee Park, Gyeonggi-do (KR); Youn Sook Lee, Gyeonggi-do (KR)

(73) Assignees: Korea Research Institute of Chemical Technology, Daejeon (KR); Research & Business Foundation Sungkyunkwan University, Suwon-si (KR)

( * ) Notice: Subject to any disclaimer, the term of this patent is extended or adjusted under 35 U.S.C. 154(b) by 0 days.

(21) Appl. No.: 15/921,596

(22) Filed: Mar. 14, 2018

(65) Prior Publication Data

US 2018/0208625 A1    Jul. 26, 2018

Related U.S. Application Data

(62) Division of application No. 15/205,853, filed on Jul. 8, 2016.

(30) Foreign Application Priority Data

Jul. 8, 2015   (KR) .................. 10-2015-0097040

(51) Int. Cl.

| A61K 47/54 | (2017.01) |
| C07K 5/117 | (2006.01) |
| C07K 5/103 | (2006.01) |
| C07K 5/107 | (2006.01) |
| C07K 5/097 | (2006.01) |
| C07D 207/04 | (2006.01) |
| A61P 1/00 | (2006.01) |
| C07D 403/06 | (2006.01) |
| A61K 38/00 | (2006.01) |

(52) U.S. Cl.
CPC .......... *C07K 5/1024* (2013.01); *A61K 47/542* (2017.08); *A61P 1/00* (2018.01); *C07D 207/04* (2013.01); *C07D 403/06* (2013.01); *C07K 5/0823* (2013.01); *C07K 5/1008* (2013.01); *C07K 5/1016* (2013.01); *A61K 38/00* (2013.01)

(58) Field of Classification Search
None
See application file for complete search history.

(56) References Cited

U.S. PATENT DOCUMENTS

| 5,068,242 A | 11/1991 | Nickel et al. |
| 6,069,254 A | 5/2000 | Costanzo et al. |
| 6,114,361 A | 9/2000 | Robinson et al. |
| 9,227,997 B2 | 1/2016 | Park et al. |
| 2002/0123459 A1* | 9/2002 | Ault .................. A61P 5/18 514/11.9 |
| 2002/0180780 A1 | 12/2002 | Honda |
| 2003/0022938 A1 | 1/2003 | Burstein et al. |
| 2006/0069254 A1 | 3/2006 | Schneider et al. |
| 2006/0114361 A1 | 6/2006 | Suzu |
| 2011/0102302 A1 | 5/2011 | Watanabe et al. |
| 2011/0142800 A1 | 6/2011 | Kidron et al. |
| 2013/0172231 A1 | 7/2013 | Park et al. |
| 2013/0237484 A1* | 9/2013 | Chung .................. C07K 14/51 514/16.6 |
| 2017/0008924 A1 | 1/2017 | Lee et al. |

FOREIGN PATENT DOCUMENTS

| KR | 10-2010-0053774 A | 5/2010 |
| KR | 10-2010-0110282 A | 10/2010 |
| KR | 101151878 B1 | 5/2012 |
| KR | 20120048864 A | 5/2012 |
| KR | 20130038426 A | 4/2013 |
| KR | 10-2013-0075934 A | 7/2013 |
| WO | 1996013507 A1 | 5/1996 |
| WO | 2006113942 A2 | 10/2006 |
| WO | 2008060552 A2 | 5/2008 |
| WO | 2010-059922 A1 | 5/2010 |
| WO | 2013-190497 A2 | 12/2013 |

OTHER PUBLICATIONS

Vicenova, B. et al, "Emerging role of interleukin-1 in cardiovascualr diseases." Physiol. Res. (2009) 58 p. 481-489.*
Sauder, D. N. et al, "Interleukin-1 enhances epidermal wound healing." Lymphokine Res. (1990) 9(4) p. 465-473.*
Allaire, Joannie M. et al, "Loss of smad5 leads to the disassembly of the apical junction complex and increased susceptibility to experimental colitis." Am. J. Phydiol. Gastrointest. Liver Physiol. (2011) 300 p. G586-G597.*
Kabanov, Alexander V. et al, "Lipid modification of proteins and their membrane transport." Prot. Eng. (1989) 3(1) p. 39-42.*
Maric, I. et al. Bone, "Bmp signaling pathway in experimental inflammatory bowel disease." (2011) 48 p. S238, abstract PP439-S.*

(Continued)

*Primary Examiner* — Fred H Reynolds
(74) *Attorney, Agent, or Firm* — Perkins Coie LLP

(57) ABSTRACT

Pyrrolidine carboxamido derivatives, optical isomers thereof, and salts thereof that are able to prevent, improve, and/or treat inflammatory conditions, including inflammatory bowel disease, and methods for preparing and using the same are provided.

16 Claims, 34 Drawing Sheets

Specification includes a Sequence Listing.

(56) References Cited

OTHER PUBLICATIONS

Rinehart, Roy K. etal, "Benzodiazepine interactions with central thyroid releasing hormone binding sites: characterization and physiological significance." J. Pharmacol. Exp Therapeut. (1986) 238(1) p. 178-185.*

Silvente-Poirot, Sandrine and Wank, Stephen A.; "A segment of five amino acids in the second extracellular loop of the cholecystokinin-b receptor is essential for selectivity of the peptide agonist gastrin." J. Biol. Chem. (1996) 271(25) p. 14698-14706.*

Knudsen, Lotte Bjerre et al, "Small molecule agonists for the glucagon like peptide 1 receptor." PNAS (2007) 104(3) p. 937-942.*

Richard, Jean Philippe etal, "Cell penetrating peptides." J. Biol. Chem. (2003) 278(1) p. 585-590.*

Li et al., "Fatty acid conjugation enhances the activities of antimicrobial peptides", Recent Pat Food Nutr Agric. 5(1):52-6 (2013).

Masschelein et al., "A combination of polyunsaturated fatty acid, nonribosomal peptide and polyketide biosynthetic machinery is used to assemble the zeamine antibiotics." Chemical Science 6(2):923-929 (2015).

G.M. Walsh, "Anti-IL-4/-13 based therapy in asthma", Expert Opinion on emerging drugs, 20(3), pp. 349-352 (2015).

S.I. Grivennikov et al., "Immunity, Inflammation, and Cancer", Cell, 140(6), pp. 883-899 (Mar. 19, 2010).

D. Ardeljan et al., "Aging is not a disease: Distinguishing age-related macular degeneration from aging", Progress in Retinal and Eye Research, vol. 37, pp. 68-89 (2013).

S. Barlas, "Medicare Part B Drug Reimbursement Program Distresses Pharmacy Players", P&T, 41(6), (2016).

G. D'Haens, "Risks and Benefits of Biologic Therapy for Inflammatory Bowel Diseases", GUT, vol. 56, pp. 725-732 (2007).

Q.K. Chen et al., "Characteristics and therapeutic efficacy of sulfasalazine in patients with mildly and moderately active ulcerative colitis", World Journal of Gastroenterology, 11(16), pp. 2462-2466 (2005).

H.Y. Park et al., "Pellino 1 promotes lymphomagenesis by deregulating BCL6 polyubiquitination", The Journal of Clinical Investigation, 124(11), pp. 4976-4988 (2014).

J.A. Bennett et al., "Pellino-1 Selectively Regulates Epthelial Cell Responses to Rhinovirus", Journal of Virology, 86 (12), pp. 6595-6604 (2012).

N. Contractor et al., "Cutting Edge: Peyer's Patch Plasmacytoid Dendritic Cells (pDCs) Produce Low Levels of Type I Interferons: Possible Role for IL-10, TGFb, and Prostaglandin E2 in Conditioning a Unique Mucosal pDC Phenotype", The Journal of Immunology, vol. 179, pp. 2690-2694 (2007).

V. Tarallo et al., "DICER1 Loss and Alu RNA Induce Age-Related Macular Degeneration via the NLRP3 Inflammasome and MyD88", Cell, 149(4), pp. 847-859 (2012).

Y. Xiao et al., "Peli1 promotes microglia-mediated CNS inflammation by regulating Traf3 degradation", Nature Medicine, 19(5), pp. 595-602 (2013).

S. Miranda-Heranandez et al., "Role for MyD88, TLR2 and TLR9 but not TLR1, TLR4 or TLR6 in Experimental Autoimmune Encephalomyelitis", The Journal of Immunology, vol. 187,pp. 1-14 (2011).

M.H. Kwack et al., "Dihydrotestosterone-Inducible IL-6 Inhibits Elongation of Human Hair Shafts by Suppressing Matrix Cell Proliferation and Promotes Regression of Hair Follicles in Mice", The Socieity for Investigative Dermatology, vol. 132, pp. 43-49 (2012).

S. Gregoriou et al., "Cytokines and Other Mediators in Alopecia Areata", Mediators of Inflammation, vol. 2010, Article IDS 928030, 5 pages (2010).

I. Brajac et al., "Human Hair Follicle: An Update on Biology and Perspectives in Hair Growth Disorders Treatment", Hair The Transplant, 4(1), 6 pages (2014).

M. Yu et al., "Interleukin-6 cytokine family member oncostatin M is a hair-follicle-expressed factor with hair growth inhibitory properties", Experimental Dermatology, vol. 17, pp. 12-19 (2007).

K.J. McElwee et al., "Hair physiology and its disorders", Drug Discovery Today: Disease Mechanisms, 5(2), pp. e163-e171 (2008).

S.A. Jones, Directing Transition from Innate to Acquired Immunity: Defining a Role for IL-61, The Journal of Immunology, vol. 175, pp. 3463-3468 (2005).

R.M. Grossman et al., "Interleukin 6 is expressed in high levels in psoriatic skin and stimulates proliferation of cultured human keratinocytes", Proc Natl Acad. Sci USA, vol. 86, pp. 6367-6371 (1989).

A. Bertoia et al., Mouse model of chronic and binge ethanol feeding (the NIAAA model), Nature Protocols, 8(3), pp. 627-637 (2013).

M. Kobayashi et al., "Toll-like receptor-dependent production of IL-12p40 causes chronic enterocolitis in myeloid cell-specific Stat3-deficient mice", The Journal of Clinical Investigation, 111(9), pp. 1297-1308 (2003).

K. Takeda et al., "Enhanced TH1 Activity and Development of Chronic Enterocolitis in Mice Devoid of Stat3 in Macrophages and Neutrophils", Immunity, vol. 10, pp. 39-49 (1999).

M. Butler et al., "Modulation of dendritic cell phenotype and function in an in vitro model of the intestinal epithelium", European Journal of Immunology, vol. 36, pp. 864-874 (2006).

M.F. Neurath et al., "The Many Roads to Inflammatory Bowel Diseases", Immunity, vol. 25, pp. 189-191 (2006).

S. Rakoff-Nahoum et al., "Recogniation of Commensal Microflora by Toll-Like Receptors is Required for Intestinal Homeostasis", Cell, vol. 118, pp. 229-241 (2004).

S.M. Gu et al., "CCR5 knockout suppresses experiemental autoimmune encephalomyelitis in C57BL/6 mice", Oncotarget, 7(13), pp. 15382-15393 (2016).

H. Zhao et al., "Isoliquiritigenin, a flavonoid from licorice, blocks M2 macrophage polarization in colitis-associated tumorigenesis through downregulating PGE2 and IL-6", Toxicology and Applied Pharmacology, vol. 279, pp. 311-321 (2014).

L. Cui et al., "The anti-inflammation effect of baicalin on experimental colitis through inhibiting TLR4/NF-kB pathway activation", International Immunopharmacology, vol. 23, pp. 294-303 (2014).

M.J. Waldner et al., "Master regulator of intestinal disease: IL-6 in chronic inflammation and cancer development", Seminars In Immunology, vol. 26, pp. 75-79 (2014).

A. Papassotiropoulos et al., "Genetics of interleukin 6: implications for Alzheimer's disease", Neurobiology of Aging, vol. 22, pp. 863-871 (2001).

M. Kawano et al., "Autocrine generation and requirement of BSF-2/IL-6 for human multiple myelomas", Nature, 323(3), pp. 83-85 (1988).

R. Sen et al., "Multiple Nuclear Factors Interact with the Immunoglobulin Enhancer Sequences", Cell, vol. 46, pp. 705-716 (1986).

S. Ghosh et al., "NF-kB and REL Proteins: Evolutionarily Conserved Mediators of Immune Responses", Annu Rev. Immunol., vol. 16, pp. 225-260 (1998).

D.M. Rothwarf et al., "IKK-g is an essential regulatory subunit of the IkB kinase complex", Nature, vol. 395, pp. 297-300 (1998).

M.A. Travis et al., "Loss of integrin avb8 on dendritic cells causes autoimmunity and colitis in mice", Nature, vol. 449, pp. 361-366 (2007).

P.L. Beck et al., "Transforming Growth Factor-b Mediates Intestinal Healing and Susceptibility to Injury in Vitro and in Vivo Through Epithelial Cells", American Journal of Pathology, 162(2), pp. 597-608 (2003).

M. Rimoldi et al., "Intestinal immune homeostasis is regulated by the crosstalk between epithelial cells and dendritic cells", Nature Immunology, 6(5), pp. 507-515 (2005).

I. Maric et al., "Bone Morphogenetic Protein-7 Reduces the Severity of Colon Tissue Damage and Accelerates the Healing of Inflammatory Bowel Disease in Rats", Journal of Cellular Physiology, vol. 196, pp. 258-264 (2003).

S. Akira et al., "Biology of multifunctional cytokines: IL 6 and related molecules (IL 1 and TNF)", The FASEB Journal, vol. 4, pp. 2860-2867 (1990).

(56) References Cited

OTHER PUBLICATIONS

Y. Horii et al., "Involvement of IL-6 in Mesangial Proliferative Glomerulonephritis", The Journal of Immunology, 143(12), pp. 3943-3955 (1989).
G. Voraberger et al., "Cloning of the Human Gene for Intercellular Adhesion Molecule 1 and Analysis of its 5'-Regulatory Region", The Journal of Immunology, 147(8), pp. 2777-2786 (1991).
S. Yamaoka et al., "Complementation Cloning of NEMO, a Component of the IkB Kinase Complex Essential for NF-kB Activation", Cell, vol. 143, pp. 1231-1240 (1998).
Y.S. Lee et al., "Inhibition of lethal inflammatory responses through the targeting of membrane-associated Toll-like receptor 4 signaling complexes with a Smad6-derived peptide", EMBO Molecular Medicine, 7(5), pp. 577-592 (2015).
Cyprotex, "Everything you need to know about ADME," 2nd Edition, Nov. 2016.
International Search Report and Written Opinion for International Application No. PCT/US2016/041563 dated Oct. 19, 2016.
Supplementary European Search Report for EP Application No. 16822053 dated Oct. 2, 2018.
Zhao et al., "Evaluation of human intestinal absorption data and subsequent derivation of a quantitative structure—Activity Relationship (QSAR) with the Abraham Descriptors," Journal of Pharmaceutical Sciences, 90(6):749-784 (2001).
Sun, H. et al., "Design of Small-Molecule Peptidic and Nonpeptidic Smac Mimetics", Accounts of Chemical Research, vol. 41, No. 10, pp. 1264-1277 (Oct. 2008).
Choi, K.C. et al., "Smad6 negatively regulates interleukin 1-receptor-Toll-like receptor signaling through direct interaction with the adaptor Pellino-1", Nature Immunology, vol. 7, No. 10, pp. 1057-1065 (Oct. 2006).
L. Covic, et al., "Pepducin-based intervention of thrombin-receptor signaling and systemic platelet activation", Nature Medicine, vol. 8, No. 10, pp. 1161-1165 (Oct. 2002).
L. Covic, "Activation and inhibition of G protein-coupled receptors by cell-penetrating membrane-tethered peptides", PNAS, vol. 99, No. 2, pp. 643-648 (Jan. 22, 2002).
"FDA approves Rybelsus® (semaglutide), the first GLP-1 analog treatment available in a pill for adults with type 2 diabetes" (https://www.novonordisk-us.com/media/news-releases.html?122973, last accessed Jan. 3, 2020).
Knudsen et al., "The Discovery and Development of Liraglutide and Semaglutide," Frontiers in Endocrinology, 10(155):1-32 (2019).
Rybelsus: Highlights of Prescribing Information, revised Sep. 2019 (https://www.accessdata.fda.gov/drugsatfda_docs/label/2019/213051s000lbl.pdf, last accessed Dec. 31, 2019).
Liu et al., "Overexpressed LIM Mineralization Proteins Do Not Require LIM Domains to Induce Bone," J Bone Min Res 17(3):406-414 (2002).
Muranishi et al., "Trials of lipid modification of peptide hormones for intestinal delivery," Journal of Controlled Release, 19:179-188 (1992).

Zhang et al., "A brain-targeting lipidated peptide for neutralizing RNA-mediated toxicity in Polyglutamine Diseases," Sci Rep 7(12077):1-13 (2017).
Hochstrasser, "Ubiquitin, proteasomes, and the regulation of intracellular protein degradation," Curr. Opin. Cell Biol, 7:215-223 (1995).
Noble et al., "Effect of age on plasma membrane asymmetry and membrane fluidity in human leukocytes and platelets," J. Gerontology: Medical Sciences, 54a(12):m601-m606 (1999).
Ring et al., "Characterization of Inverted Membrane Vesicles from the Halophilic Archaeon Haloferax volcanii," J. Membrane Biology, 183:195-204 (2001).
Zanetti-Domingues et al., "Hydrophobic fluorescent probes introduce artifacts into single molecule tracking experiments due to non-specific binding," PLOS One, 8(9):e74200 (2013).
"GLP-1 Analog Semaglutide—Oral Formulation starts Phase 3a Development," Diabetes News Journal, Aug. 27, 2015, retreived from https://diabetesnewsjournal.com/2015/08/27/glp1-analog-semaglutide/ on Aug. 13, 2021 (2 pages).
"New Diabetes Drug Comes in a Pill," Chemical and Engineering News, Sep. 30, 2019, p. 10.
"Novo Nordisk Starts Phase I Trial with Long-Acting Oral GLP-1 Analogue," Business Wire, Jan. 13, 2010, retreived from https://www.bloomberg.com/press-releases/2010-01-13/novo-nordisk-starts-phase-i-trial-with-long-acting-oral-glp-1 on Aug. 13, 2021 (3 pages).
Brooks et al., 2005, "Tat peptide-mediated cellular delivery: back to basics," Adv. Drug Deliv. Rev., 57(4):559-577.
Brown et al., 2014, "Intranasal delivery of a peptide with antidepressant like effect," Neuropsychopharmacology, 39:2131-2141.
Erdos et al., 1966, "Automated peptide synthesis," Hypotensive Peptides, Merrifield, R. B., 1-13.
Green et al., 2003, "Protein transduction domains: are they delivering?," Trends in Pharmacological Sciences, 24(5):213-215.
Koyama et al., 2018, "Fluorinated polymer surfactants bearing an alternating peptide skeleton prepared by three-component polycondensation," RSC Adv., 8(14):7509-7513.
Kurtzhals et al., 1995, "Albumin binding of insulins acylated with fatty acids: characterization of the ligand-protein interaction and correlation between binding affinity and timing of the insulin effect in vivo," Biochem. J., 312(Pt 3):725-731.
Lindgren et al., 2000, "Cell-penetrating peptides," Trends Pharmacol. Sci., 21(3):99-103.
Patent Trial and Appeal Board Decision issued under Appeal No. 2021-002105 for U.S. Appl. No. 15/921,596 dated Jun. 14, 2021 (12 pages).
Patent Trial and Appeal Board Decision issued under Appeal No. 2021-002503 for U.S. Appl. No. 15/205,853 dated Jun. 14, 2021 (22 pages).
Potocky et al., 2003, "Cytoplasmic and nuclear delivery of a TAT-derived peptide and a beta-peptide after endocytic uptake into HeLa cells," J. Biol. Chem., 278(50):50188-50194.
Spector et al., 2019, "Genetic variation and function of the HIV-1 Tat protein," Med. Microbiol. Immunol., 208(2):131-169.
Tolls et al., 2002, "Bioconcentration of n-dodecane and its highly branched isomer 2,2,4,6,6-pentamethylheptane in fathead minnows," Chemosphere, 47(10):1049-1057.

* cited by examiner

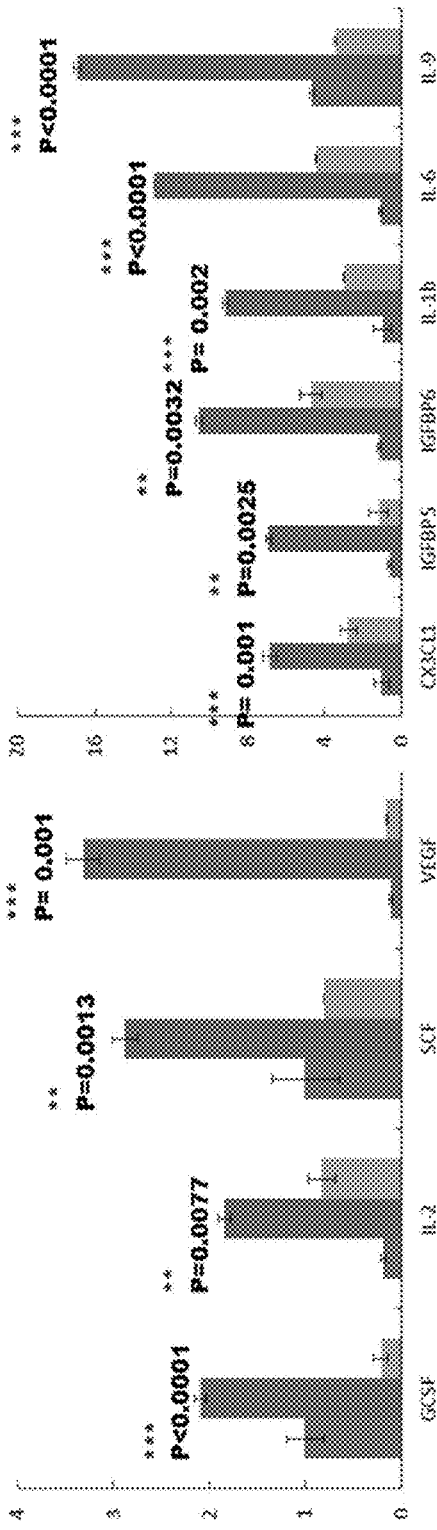
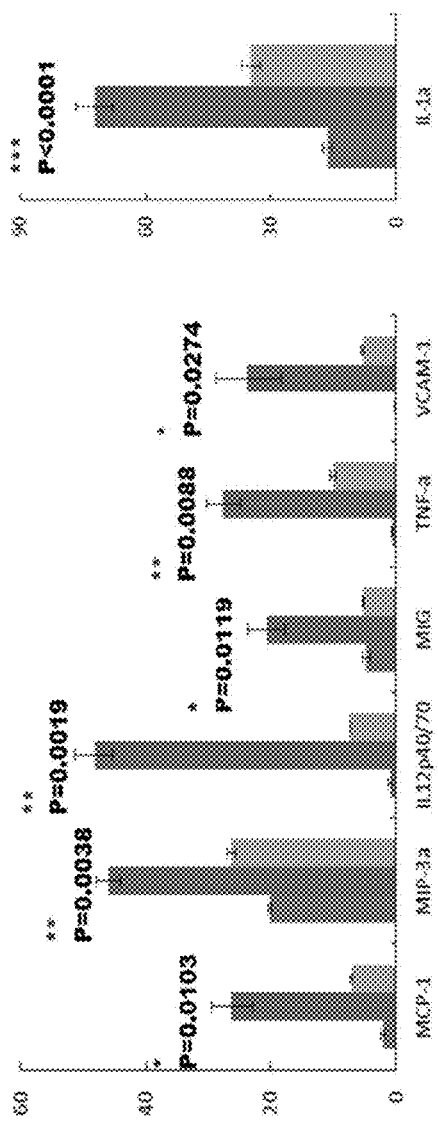
FIG. 2A  FIG. 2B  FIG. 2C  FIG. 2D

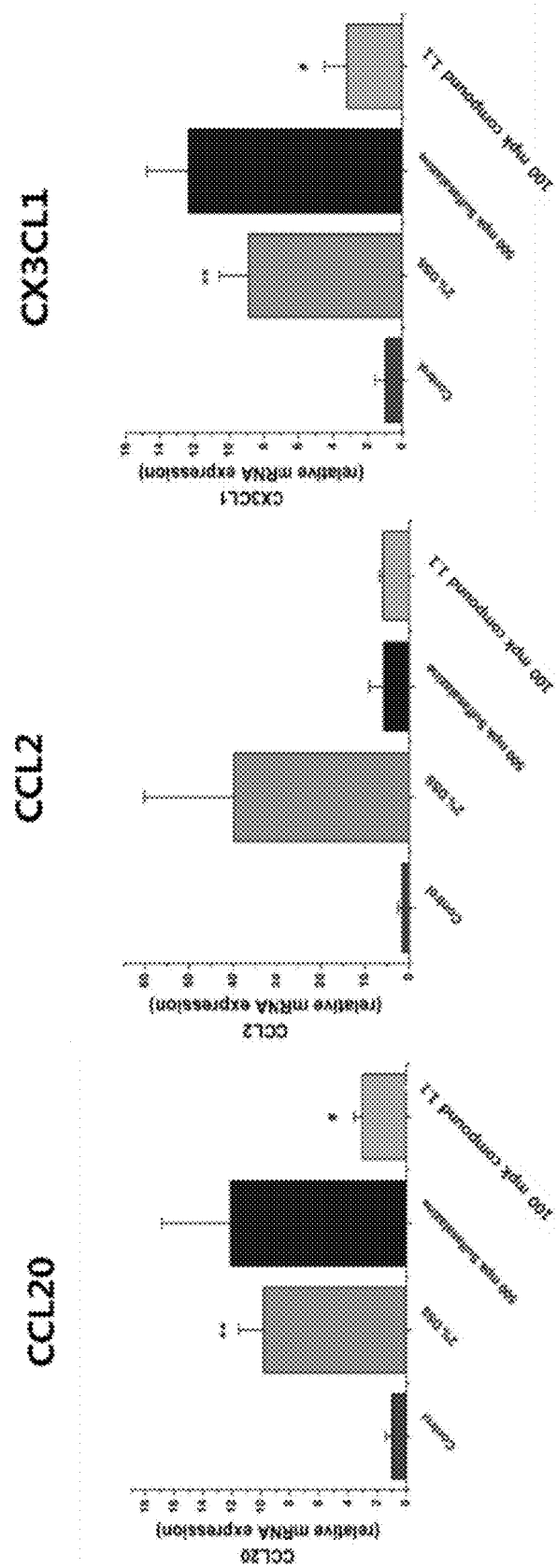

DSS: dextran sodium sulfate (DSS) treated

METHOD FOR PREVENTING, IMPROVING, OR TREATING INFLAMMATORY BOWEL DISEASE

CROSS REFERENCE TO RELATED APPLICATION

This application is a divisional application of U.S. application Ser. No. 15/205,853 filed on Jul. 8, 2016, which claims priority to Korean Application No. 10-2015-0097040 filed on Jul. 8, 2015. The applications are incorporated herein by reference.

INCORPORATION-BY-REFERENCE OF SEQUENCE LISTING

The contents of the sequence listing text file named "BBH-00202 20190621.txt", which was created on Jun. 21, 2019 and is 5,178 bytes in size, is hereby incorporated by reference in its entirety.

TECHNICAL FIELD

The present invention relates to pyrrolidine carboxamido derivatives, optical isomers thereof, or pharmaceutically acceptable salts thereof, and methods for preparing and using the same.

BACKGROUND ART

Various compounds/compositions/methods including, but not limited to, immunosuppressive drugs (e.g., infliximab), aminosalicylic acids (e.g., sulfasalazine), and steroids have been proposed as means for reducing cytokines and/or chemokines to prevent and/or treat various diseases including, but not limited to, inflammatory indications, cancers, and ophthalmic indications (Expert opinion on emerging drugs (2015) 20(3):349-352; Cell. (2010) Mar. 19; 140(6): 883-899; Progress in Retinal and Eye Research 37(2013) 68e89, which are incorporated herein by reference). They are, however, unsatisfactory at least because they are expensive, and/or involve side effects, and/or show low therapeutic efficacy (P&T 41(2016), Jun no 6; Gut 56(2007):725-732; World J Gastroenterol (2005); 11(16):2462-2466, which are incorporated herein by reference). Therefore, there remains a need for a new compound, composition, and/or a method.

SUMMARY

The present invention is based on the discovery that certain pyrrolidine carboxamido derivatives are able to suppress the expression and activity of inflammatory cytokines (e.g., IL-6) and/or chemokines and are able to remain at a sufficiently high concentration in a target tissue/cell while being less exposed to blood. The present invention is also based on the discovery that certain pyrrolidine carboxamido derivatives are able to inhibit the activity of NF-κB by stabilizing of IκB. The present invention is further based on the discovery that certain pyrrolidine carboxamido derivatives are able to disrupt the formation of inflammatory signal transduction complex mediated by myeloid differentiation primary response gene 88 (MyD88) and/or receptor-interacting protein 1 (RIP1) that act in the downstream of signaling pathway involving toll-like receptor 2/4 and IL-1β.

In one aspect, the present invention provides compounds represented by the following Formula 1, optical isomers thereof, or pharmaceutically acceptable salts thereof.

SEQ ID NO: 1

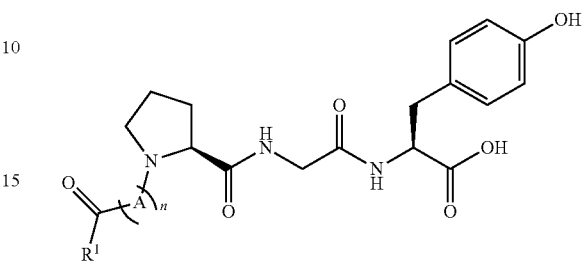

[Formula 1]

wherein: n is 0, 1, or 2; A is -a¹-, which is an amino acid independently selected from the group consisting of alanine, (Ala, A), arginine (Arg, R), asparagine (Asn, N), aspartic acid (Asp, D), cysteine (Cys, C), glutamic acid (Glu, E), glutamine (Gln, Q), glycine (Gly, G), histidine (His, H), isoleucine (Ile, I), leucine (Leu, L), lysine (Lys, K), methionine (Met, M), phenylalanine (Phe, F), proline (Pro, P), serine (Ser, S), threonine (Thr, T), tryptophan (Trp, W), tyrosine (Tyr, Y), and valine (Val, V), both terminal ends of the amino acid being coupled to a carbonyl group or an amine group by an amide bond; and $R^1$ is a straight chain or branched chain $C_{1-36}$ alkyl, a straight chain or branched chain $C_{2-36}$ alkenyl including at least one double bond, or a straight chain or branched chain $C_{2-36}$ alkynyl including at least one triple bond.

In another aspect, the present invention provides methods for preparing the compounds, the optical isomers, and the salts.

In still another aspect, the present invention provides compositions for preventing, improving, and treating various diseases (e.g., inflammatory indications, cancers, and ophthalmic indications). The compositions each comprise, as an active component, at least one of the compounds, at least one of the optical isomers, or at least one of the salts.

In still yet another aspect, the present invention provides methods for preventing, improving, or treating various diseases (e.g., inflammatory indications, cancers, and ophthalmic indications). The methods each comprise administering to a subject in need a composition containing, as an active component, at least one of the compounds, at least one of the optical isomers, or at least one of the salts.

Compounds according to certain embodiments of the present invention may inhibit decomposition of IκB in inflammation signaling pathway mediated by MyD88 (myddosome complex) and/or RIP 1, thereby preventing NF-κB from being transported into nucleus of a cell, resulting in suppression of expression of cytokines and chemokines (e.g., G-CSF, IL-2, SCF, VEGF, CX3CL1, IGFBP5, IGFBP6, IL-1α, IL-1β, IL-6, IL-9, MCP-1, MIP-3α, IL12p40/70, MIG, TNF-α, and VCAM-1) and preventing inflammation reaction that could otherwise be caused by the expression thereof.

Other aspects and advantages of the present invention will become apparent to the skilled in the art from a consideration of the detailed description and the drawings.

BRIEF DESCRIPTION OF DRAWINGS

FIGS. 2A-2D are bar graphs that show that compounds according to embodiments of the present invention suppress the expression of cytokines and chemokines in a cell line RAW 264.7. FIG. 2A is a bar graph that shows that the expression of GCSF, IL-2, SCF, and VEGF was suppressed as statistically meaningful when the cells were treated with the compounds of the present invention. FIG. 2B is a bar graph that shows that the expression of CX3CL1, IGFBP5, IGFBP6, IL-1 b, IL-6, and IL-9 was suppressed as statistically meaningful when the cells were treated with the compounds of the present invention. FIG. 2C is a bar graph that shows that the expression of MCP-1, MIP-3a, IL12p40/70, MIG, TNF-a, and VCAM-1 was suppressed as statistically meaningful when the cells were treated with the compounds of the present invention. FIG. 2D is a bar graph that shows that the expression of IL-1a was suppressed as statistically meaningful when the cells were treated with the compounds of the present invention.

FIGS. 11B-11D shows the compounds according to embodiments of the present invention affect the amount of expression of chemokines (CCL2 (FIG. 11C), CCL20 (FIG. 11B), and CXCL1 (FIG. 11D)) in a mice model with DSS-induced chronic colitis. (Compound 1.1 (SEQ ID NO: 2)).

FIG. 23A is an immunoblot image showing cells pretreated with compound 1.1 (SEQ ID NO: 2) (100 nM), IRAK1/4 inhibitor (25 μM) and smaducin-6 (100 nM) and then further treated with LPS (100 ng/ml). FIG. 23B is an immunoblot image showing that RAK1/4 inhibitor also suppressed degradation of IκB similar to compound 1.1 (SEQ ID NO: 2).

FIG. 25A is a Western blot image confirming that compounds according to embodiments of the present invention (Compound 1.1 (SEQ ID NO: 2)) suppress, in ARPE-19, expression of Nox-4, VEGF, VEGFR1, and VEGFR2. FIG. 25B is a Western blot image confirming that compounds according to embodiments of the present invention (Compound 1.1 (SEQ ID NO: 2)) suppress, in ARPE-19, Ang-2, EPO, and EPOR, and can increase expression of Ang-1 and Tie2.

FIG. 27A shows an image of the administration schedule. FIG. 27B are images showing retina tissues stained with 5 μM of dihydroethidium and measured active oxygen rates from each group. (Compound 1.1 (SEQ ID NO: 2)).

DETAILED DESCRIPTION

1. Definitions

Figure 1A:
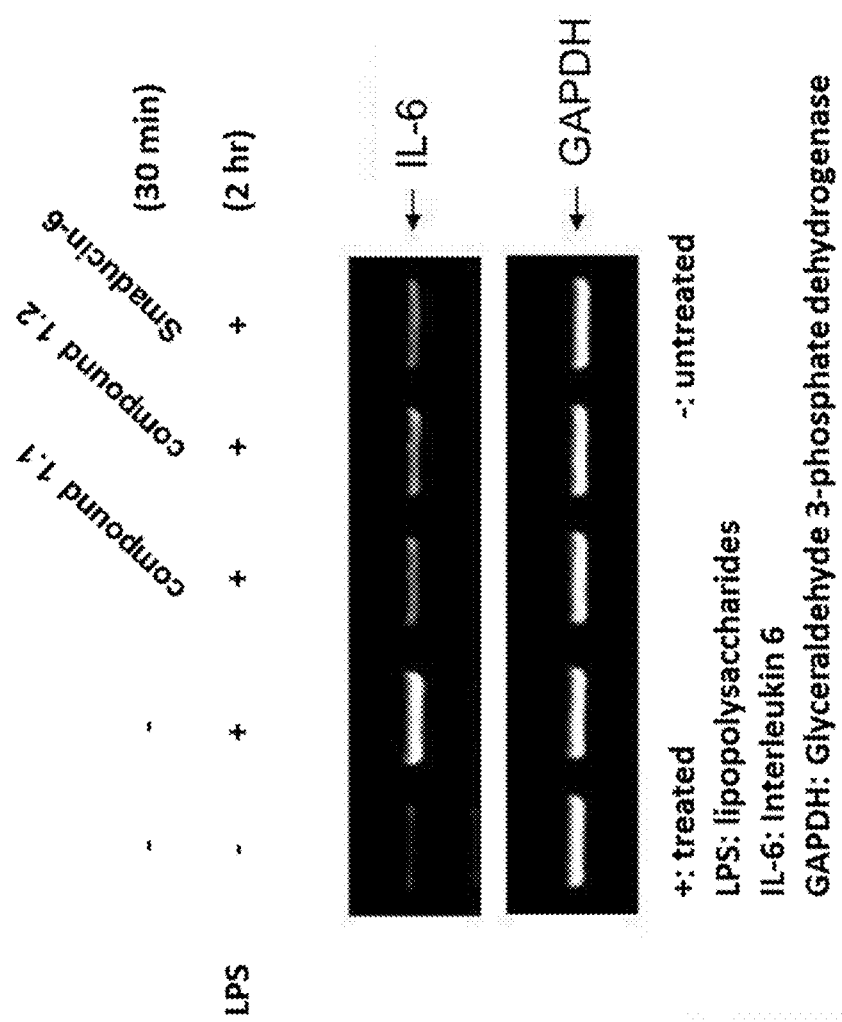
FIG. 1A is an electrophoresis result showing that compounds according to embodiments of the present invention suppress the expression of IL-6. (Compound 1.1 (SEQ ID NO: 2)).

Unless defined otherwise, all technical and scientific terms used herein have the meaning commonly understood by a person skilled in the art to which this disclosure belongs. The following references, which are incorporated herein by reference, provide one of skill with a general definition of many of the terms used in this invention: The Cambridge Dictionary of Science and Technology (Walker ed., 1988); The Glossary of Genetics, 5th Ed., R. Rieger et. al. (eds.), Springer Verlag (1991); and Hale & Marham, The Harper Collins Dictionary of Biology (1991). As used herein, the following terms have the meanings ascribed to them below, unless specified otherwise.

Unless specifically stated or obvious from context, as used herein, the term "or" is understood to be inclusive.

Unless specifically stated or obvious from context, as used herein, the terms "a", "an", and "the" are understood to be singular or plural. Thus, for example, reference to "a compound" includes mixtures of such compounds; reference to "a carrier" includes mixtures of two or more carriers; and the like.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The terms "active agent," "drug," and "pharmaceutical agent" are used interchangeably herein to refer to a chemical material or compound which, when administered to a subject (e.g., any animal including a human or non-human animal) by any means and/or routes induces a desired pharmacologic effect (e.g., such as a reduction of inflammation).

The term "additive" as used herein may refer to any additional components that may be added to the compositions described herein. For example, additives may include excipients (e.g., one or more excipients), antioxidants (e.g., one or more antioxidants), stabilizers (e.g., one or more stabilizers), preservatives (e.g., one or more preservatives), pH adjusting and/or buffering agents (e.g., one or more pH adjusting and/or buffering agents), tonicity adjusting agents (e.g., one or more tonicity adjusting agents), thickening agents (e.g., one or more thickening agents), suspending agents (e.g., one or more suspending agents), binding agents (e.g., one or more binding agents), viscosity-increasing agents (e.g., one or more viscosity-increasing agents), and the like, provided that the additional components are pharmaceutically acceptable for the particular condition to be treated. The additives may also include processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-beta-cyclodextrin, polyvinylpyrrolidinone, low melting waxes, ion exchange resins, and the like, as well as combinations of any two or more thereof. Other suitable pharmaceutically acceptable excipients are described in "Remington's Pharmaceutical Sciences," Mack Pub. Co., New Jersey (1991), and "Remington: The Science and Practice of Pharmacy," Lippincott Williams & Wilkins, Philadelphia, 20th edition (2003) and 21st edition (2005), which are incorporated herein by reference. The additives described herein may be used in any suitable amounts.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., oral, nasal, pulmonary, rectal, buccal, vaginal, ocular and transdermal routes).

The terms "derivative" and 'analog" are used herein interchangeably, and refer to a compound that possesses the same core as a parent compound, but differs from the parent compound in bond order, in the absence or presence of one or more atoms and/or groups of atoms, and combinations thereof. The derivative can differ from the parent compound, for example, in one or more substituents present on the core, which may include one or more atoms, functional groups, or substructures. The derivative can also differ from the parent compound in the bond order between atoms within the core. In general, a derivative can be imagined to be formed, at least theoretically, from the parent compound via chemical and/or physical processes.

As used herein, "antioxidants" may refer to are man-made or natural substances that may prevent or delay some types of cell damage and/or oxidation. Antioxidants are found in many foods, including fruits and vegetables. They are also available as dietary supplements. Exemplary antioxidants may include: β-eta-carotene, Lutein, Lycopene, Selenium, Vitamin A, Vitamin C, and Vitamin E. Other antioxidants known to one of skill in the art may also be used. The antioxidants described herein may be used in any suitable amount.

By "co-administer" it is meant that a compound or composition described herein is administered at the same time, just prior to, or just after the administration of additional therapies or active agents or additives described herein. The compound or the composition of the disclosure can be administered alone or can be co-administered to a subject in need. Co-administration is meant to include simultaneous or sequential administration of the compound individually or in combination (more than one compound or agent). The preparations can also be combined, when desired, with other active substances.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

As used herein, "concurrent administration" includes overlapping in duration at least in part. For example, when two agents (e.g., any of the agents or class of agents described herein that has bioactivity) are administered concurrently, their administration occurs within a certain desired time. The agents' administration may begin and end on the same day. The administration of one agent can also precede the administration of a second agent by day(s) as long as both agents are taken on the same day at least once. Similarly, the administration of one agent can extend beyond the administration of a second agent as long as both agents are taken on the same day at least once. The active agent(s) does not have to be taken at the same time each day to include concurrent administration.

As used herein, an "effective amount" or "therapeutically effective amount" is that amount sufficient to affect a desired biological effect, such as beneficial results, including clinical results. As such, an "effective amount" depends upon the context in which it is being applied. An effective amount may vary according to factors known in the art, such as the disease state, age, sex, and weight of the individual being treated. Several divided doses may be administered daily or the dose may be proportionally reduced as indicated by the exigencies of the therapeutic situation. In addition, the compounds, compositions, or formulations of this disclosure can be administered as frequently as necessary to achieve a therapeutic amount.

The term, "gel" as used herein may refer to a material which is not a readily flowable liquid and not a solid, i.e., semi-solid. Gels may be formed from naturally occurring or synthetic materials. The gels can be non-ordered to slightly ordered showing some birefringence, liquid crystal character. Gels may be administered topically.

The term "inflammatory bowel disease" as used herein has its usual medical meaning, and refers to a group of inflammatory indications/conditions of a colon and small intestine. Exemplary inflammatory bowel diseases may include, but are not limited to, Crohn's disease, ulcerative colitis, Johne's disease, Behget's syndrome, collagenous colitis, diversion colitis, indeterminate colitis, infective colitis, ischaemic colitis, lymphocytic colitis, and closely related diseases and disorders of the gastrointestinal tract.

The term "inhibit," as used herein, means to prevent, decrease, slow-down or arrest. In one embodiment, a compound, composition, or formulation may be considered to inhibit the viability of at least one protein (e.g., G-CSF, IL-2, SCF, VEGF, CX3CL1, IGFBP5, IGFBP6, IL-1α, IL-1β, IL-6, IL-9, MCP-1, MIP-3α, IL12p40/70, MIG, TNF-α, VCAM-1, and NF-κB) when the amount or rate of the process or reaction that takes place in the presence of the compound, composition, or formulation is decreased by at least about 10% when compared to the amount or rate in the absence of the compound, composition, or formulation. In another embodiment, a compound, composition, or formulation may be considered to inhibit a process or reaction when the amount or rate of the process or reaction that takes place in the presence of the compound, composition, or formulation is decreased by at least about 20% when compared to the amount or rate in the absence of the compound, composition, or formulation. In other embodiments, a compound, composition, or formulation may be considered to inhibit viability of one or more proteins (e.g., G-CSF, IL-2, SCF, VEGF, CX3CL1, IGFBP5, IGFBP6, IL-1α, IL-1β, IL-6, IL-9, MCP-1, MIP-3α, IL12p40/70, MIG, TNF-α, VCAM-1, and NF-κB) when the amount or rate of viability that takes place in the presence of the compound, composition, or formulation is decreased by at least about 25%, about 30%, about 40%, about 50%, about 60%, about 70%, about 75% or about 80% when compared to the amount or rate in the absence of the compound, composition, or formulation. In still other embodiments, a compound, composition, or formulation may be considered to inhibit viability of one or more proteins, i.e. arresting its development.

As used herein, "intermittent administration" includes the administration of an active agent for a period of time (which can be considered a "first period of administration"), followed by a time during which the agent is not taken or is taken at a lower maintenance dose (which can be considered "off-period") followed by a period during which the agent is administered again (which can be considered a "second period of administration"). Generally, during the second phase of administration, the dosage level of the agent will match that administered during the first period of administration but can be increased or decreased as medically necessary.

"Jelly" according to the current disclosure is a class of gels, which are semisolid systems that consist of suspensions made up either small inorganic particles or large organic molecules interpenetrated by a liquid, in which the structural coherent matrix contains a high portion of liquid, usually water.

"Liquid" as used herein is a dosage form consisting of a composition in its liquid state. A liquid is pourable; it flows and conforms to its container at room temperature. Liquids display Newtonian or pseudoplastic flow behavior. In embodiments, a "semi-liquid" as used herein may have properties of both a liquid and another formulation (i.e., a suspension, an emulsion, a solution, a cream, a gel, a jelly, and the like).

"Myeloid differentiation primary response gene 88" or "MYD88" is a protein that, in humans, is encoded by the MYD88 gene. MyD88 plays a central role in the innate and adaptive immune response. This protein functions as an essential signal transducer in the interleukin-1 and Toll-like receptor signaling pathways. These pathways regulate that activation of numerous proinflammatory genes. The encoded protein consists of an N-terminal death domain and a C-terminal Toll-interleukin1 receptor domain.

As used herein, the term "ointment" may refer to a highly viscous liquid or semi-liquid formulation that may be used for therapeutic treatment of a disease, syndrome, or condition (e.g., inflammatory bowel disease).

As used herein "pharmaceutically acceptable carrier" includes any and all solvents, dispersion media, coatings, antibacterial and antifungal agents, isotonic and absorption delaying agents, and the like that are physiologically compatible. The type of carrier can be selected based upon the intended route of administration. Pharmaceutically acceptable carriers include sterile aqueous solutions or dispersions and sterile powders for the extemporaneous preparation of sterile topical solutions or dispersion. The use of such media and agents for pharmaceutically active substances is well known in the art. Except insofar as any conventional media or agent is incompatible with the composition (e.g., Formula I (SEQ ID NO: 1) as described herein, derivatives/analogues of Formula I (SEQ ID NO: 1), or a pharmaceutically acceptable salt, solvent, hydrate, or polymorph thereof), use thereof in the ophthalmic compositions for the disclosure is contemplated.

"Pharmaceutical carriers" or "carriers" as used herein can further include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween™, polyethylene glycol (PEG), and Pluronics™.

Additionally, "pharmaceutically acceptable" means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

The terms, "pH agent" or "buffering agent" as used herein may refer to compounds or buffers useful as pH regulators. These include, but are not limited to, glycerol buffers, citrate buffers, borate buffers, acetate buffers, gluconate buffers, phosphate buffers, or citric acid-phosphate buffers may also be included. The pH agent or buffering agent may be used in any suitable amount.

The term, "preservative" as described herein may refer to a substance or chemical that prevents undesirable chemical changes of the compound or compositions or formulas described herein. Suitable preservatives may include, for example, benzalkonium chloride, thimerosal, chlorobutanol, methyl paraben, propyl paraben, phenylethyl alcohol, edetate disodium sorbic acid, Onamer M Polyquat, cetyl bromide, cetyl pyridinium chloride, benzyl bromide, EDTA, phenylmercury nitrate, phenylmercury acetate, thimerosal, merthiolate, acetate and phenylmercury borate, polymyxin B sulphate, methyl and propyl parabens, quaternary ammonium chloride, sodium benzoate, sodium proprionate, and sodium perborate, and other agents known to those skilled in the art, or a combination thereof. The preservative may be used in any suitable amount.

The terms "prevent," "preventing," or "prevention," and other grammatical equivalents as used herein, include to keep from developing, occur, hinder or avert a disease or condition symptoms as well as to decrease the occurrence of symptoms. The prevention may be complete (i.e., no detectable symptoms) or partial, so that fewer symptoms are observed than would likely occur absent treatment. The terms further include a prophylactic benefit. For a disease or condition to be prevented, the compositions may be administered to a patient at risk of developing a particular disease, or to a patient reporting one or more of the physiological symptoms of a disease, even though a diagnosis of this disease may not have been made.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction. Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it is understood that the particular value forms another aspect. It is further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. It is also understood that throughout the application, data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

"Receptor interacting protein" or "RIP1" as used herein describes a protein kinase which is a crucial regulator of cell survival and death. RIP1 and RIP2 also bear a C-terminal domain belonging to the death domain superfamily, allowing recruitment to large protein complexes initiating different signaling pathways.

As used herein, "salts" or "salt form" or "pharmaceutically accepted salts" may include base addition salts (formed with free carboxyl or other anionic groups) which are derived from inorganic bases such as, for example, sodium, potassium, ammonium, calcium, or ferric hydroxides, and such organic bases as isopropylamine, triethylamine, 2-ethylamino-ethanol, histidine, procaine, and the like. Such salts are formed as acid addition salts with any free cationic groups and generally are formed with inorganic acids such as, for example, hydrochloric, sulfuric, or phosphoric acids, or organic acids such as acetic, citric, p-toluenesulfonic, methanesulfonic acid, oxalic, tartaric, mandelic, and the like. Salts of the disclosure may include amine salts formed by the protonation of an amino group with inorganic acids such as hydrochloric acid, hydrobromic acid, hydroiodic acid, sulfuric acid, phosphoric acid, and the like. Salts of the disclosure also include amine salts formed by the protonation of an amino group with suitable organic acids, such as p-toluenesulfonic acid, acetic acid, and the like. Additional excipients which are contemplated for use in the practice of the present disclosure are those available to those of ordinary skill in the art, for example, those found in the United States Pharmacopoeia Vol. XXII and National Formulary Vol. XVII, U.S. Pharmacopoeia Convention, Inc., Rockville, Md. (1989), the relevant contents of which is incorporated herein by reference.

The "semisolid gel" according to the current disclosure is a semisolid. The semisolid formulation apparent viscosity may increase with concentration.

As used herein, "sequential administration" includes that the administration of two agents (e.g., the compounds or compositions described herein) occurs separately on the same day or do not occur on a same day (e.g., occurs on consecutive days).

"Solution" according to the current disclosure may be a clear, homogeneous liquid dosage form that contains one or more chemical substances dissolved in a solvent or mixture of mutually miscible solvents. A solution is a liquid preparation that contains one or more dissolved chemical substances in a suitable solvent or mixture of mutually miscible solvents. Because molecules of a drug substance in solution are uniformly dispersed, the use of solutions as dosage forms generally provides assurance of uniform dosage upon administration and good accuracy when the solution is diluted or otherwise mixed.

The term "solvent," as used herein, refers to a liquid solvent either aqueous or non-aqueous. The selection of the solvent depends notably on the solubility of the composition on said solvent and on the mode of administration. Aqueous solvent may consist solely of water, or may consist of water plus one or more miscible solvents, and may contain dissolved solutes such as sugars, buffers, salts or other excipients. The more commonly used non-aqueous solvents are the short-chain organic alcohols, such as, methanol, ethanol, propanol, short-chain ketones, such as acetone, and poly alcohols, such as glycerol. The solvent may be present in any suitable amount By "subject" or "patient" is meant either a human or non-human animal, such as a mammal. "Subject" may include any animal, including horses, dogs, cats, pigs, goats, rabbits, hamsters, monkeys, guinea pigs, rats, mice, lizards, snakes, sheep, cattle, fish, and birds. A human subject may be referred to as a patient.

"Suspension" as used herein is a liquid dosage form that contains solid particles dispersed in a liquid vehicle.

As used herein, the term "syndrome" may refer to a group of symptoms that consistently occur together or a condition characterized by a set of associated symptoms. A syndrome (e.g., inflammatory bowel syndrome) may be a set of medical signs and symptoms that are correlated with each other and often, are correlated with a specific disease. A disease, on the other hand, may be a health condition that has a clearly defined reason behind it. A syndrome (from the Greek word meaning 'run together') however, may produce a number of symptoms without an identifiable cause. They may suggest the possibility of an underlying disease or even the chances of developing a disease.

The terms "treat," "treating" or "treatment," and other grammatical equivalents as used herein, include alleviating, abating, ameliorating, or preventing a disease, condition (e.g., inflammatory bowel disease) or symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition, and are intended to include prophylaxis. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder.

As used herein, "viscosity" refers to a fluid's resistance to flow. Viscosity agents may be used herein and include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, other agents known to those skilled in the art, or a combination thereof.

The term "weight percent" or "% (w/w)" refers to a percentage of a component in a solution that is calculated on the basis of weight for the component and the solvent. For example, a 1% (w/w) solution of a component would have 1 g of the component dissolved in a 100 g of solvent. The term "volume percent" or "% (v/v)" refers to a percentage of a component in a solution that is calculated on the basis of volume for the component and the solvent. For example, a 1% (v/v) solution of a component would have 1 ml of the component dissolved in a 100 ml of solvent. The term "weight/volume percent" or "% (w/v)" refers to a percentage of a component in a solution that is calculated on the basis of weight for the component and on the basis of volume for the solvent. For example, a 1.0% (w/v) solution of a component would have 1 g of the component dissolved in a 100 ml of solvent

2. Compounds

As discussed above, one aspect of the present invention provides a compound represented by the following Formula 1, an optical isomer thereof, or a pharmaceutically acceptable salt thereof.

SEQ ID NO: 1

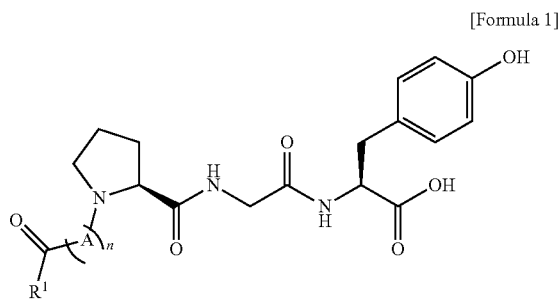

[Formula 1]

wherein: n is 0, 1, or 2; A is -a¹-, which is an amino acid independently selected from the group consisting of alanine, (Ala, A), arginine (Arg, R), asparagine (Asn, N), aspartic acid (Asp, D), cysteine (Cys, C), glutamic acid (Glu, E), glutamine (Gln, Q), glycine (Gly, G), histidine (His, H), isoleucine (Ile, I), leucine (Leu, L), lysine (Lys, K), methionine (Met, M), phenylalanine (Phe, F), proline (Pro, P), serine (Ser, S), threonine (Thr, T), tryptophan (Trp, W), tyrosine (Tyr, Y), and valine (Val, V), both terminal ends of the amino acid being coupled to a carbonyl group or an amine group by an amide bond; and $R^1$ is a straight chain or branched chain $C_{1-36}$ alkyl, a straight chain or branched chain $C_{2-36}$ alkenyl including at least one double bond, or a straight chain or branched chain $C_{2-36}$ alkynyl including at least one triple bond.

The term "compound of the present invention", and equivalent expressions, are meant to embrace the compound of the Formula as hereinbefore described, which expression includes the pharmaceutically acceptable salts, and the solvates, e.g., hydrates, and the solvates of the pharmaceutically acceptable salts where the context so permits.

In accordance with some embodiments of the invention, $a^1$ may be

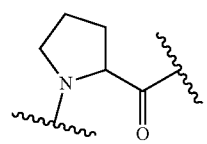 [SMILES: *C(=O)C1CCCN1*]

and $R^1$ may be a straight chain or branched chain $C_{1-36}$ alkyl (SEQ ID NO: 17).

Non-limiting examples of the compounds include the following compounds:

SEQ ID NO: 2

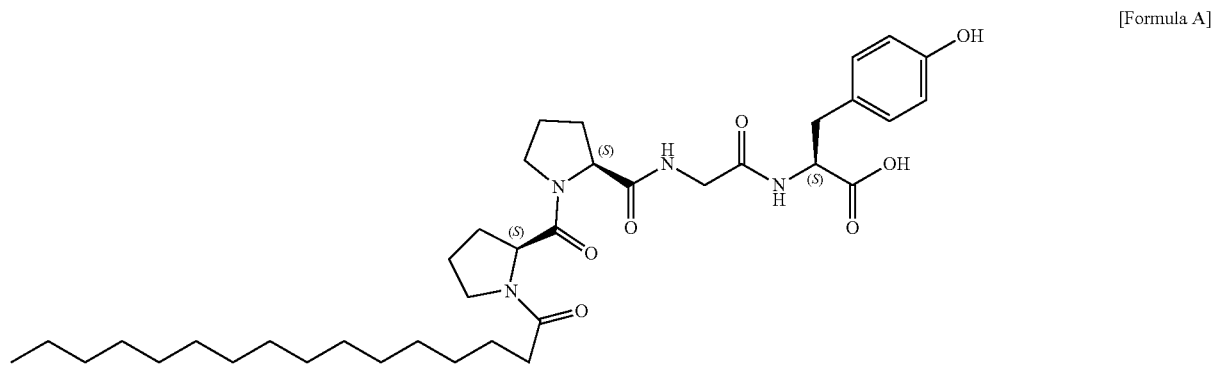

[Formula A]

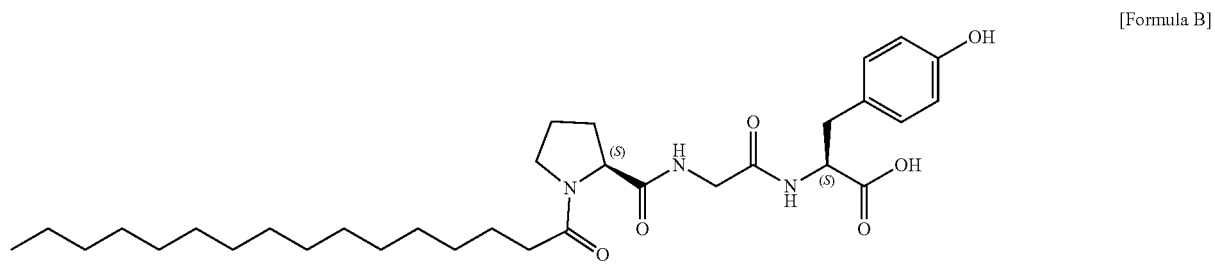

[Formula B]

-continued
SEQ ID NO: 3
[Formula C]
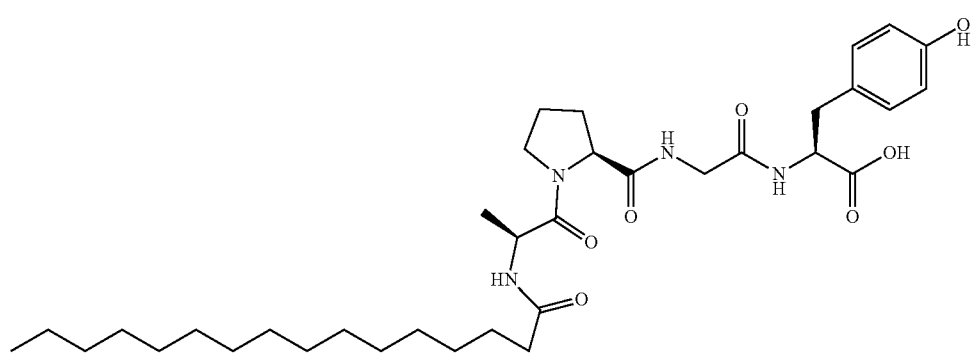
SEQ ID NO: 4
[Formula D]
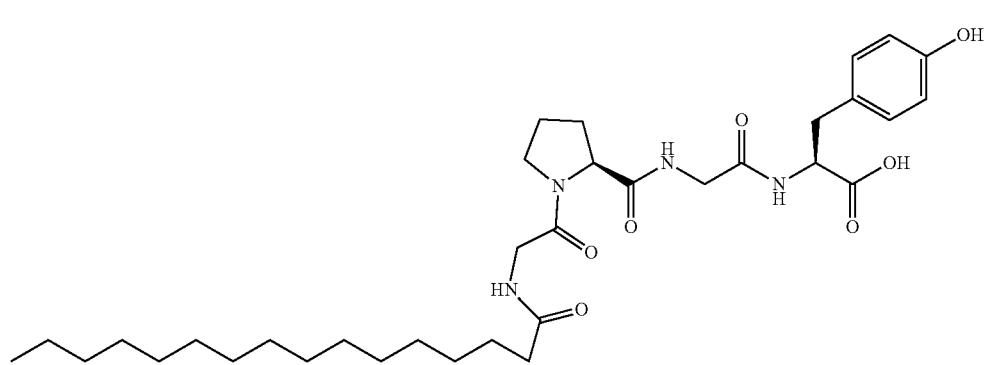
SEQ ID NO: 5
[Formula E]
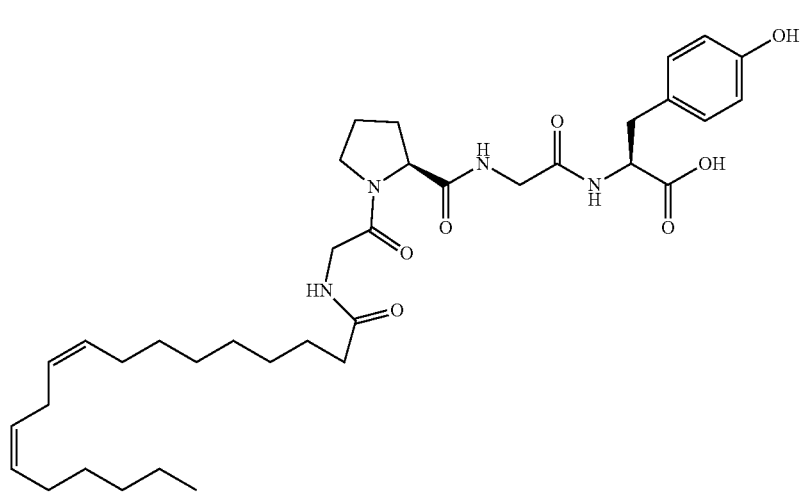

SEQ ID NO: 6
[Formula F]
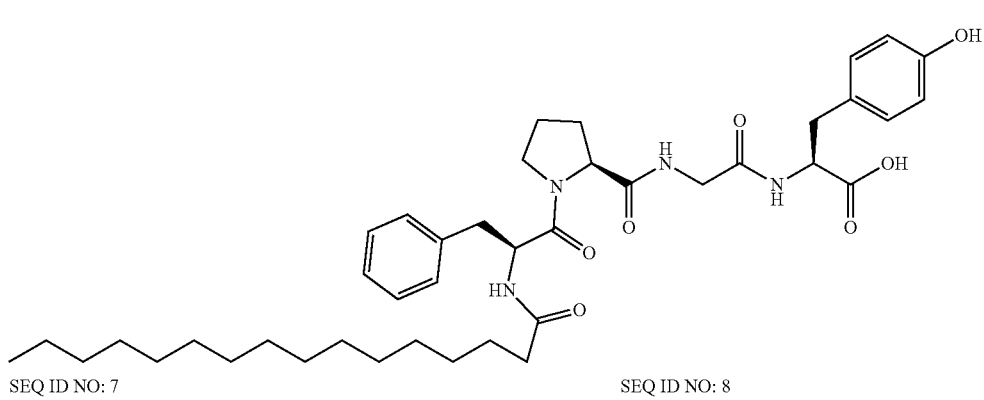
SEQ ID NO: 7
SEQ ID NO: 8
[Formula G]
[Formula H]
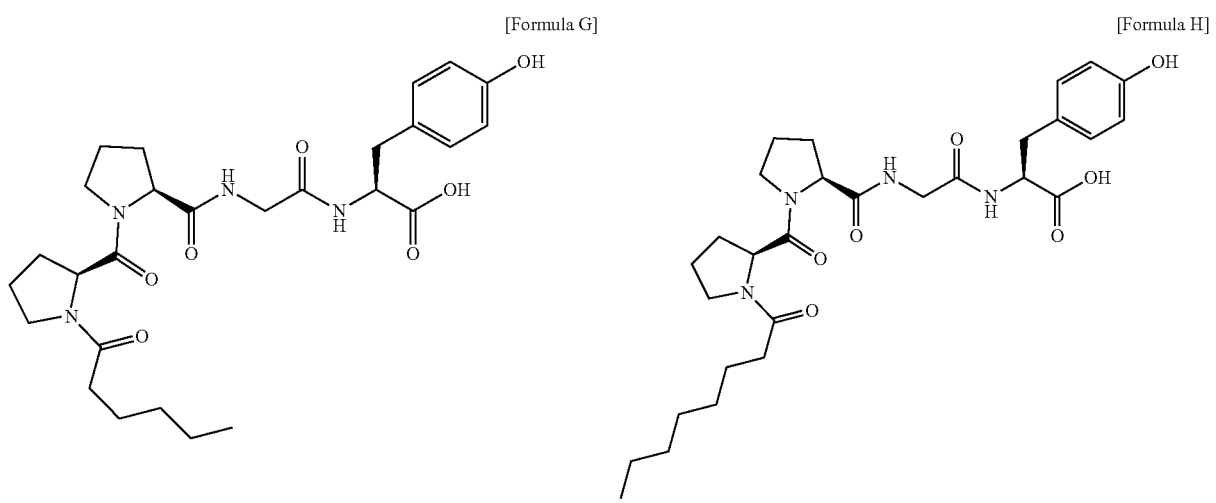
SEQ ID NO: 9
[Formula I]
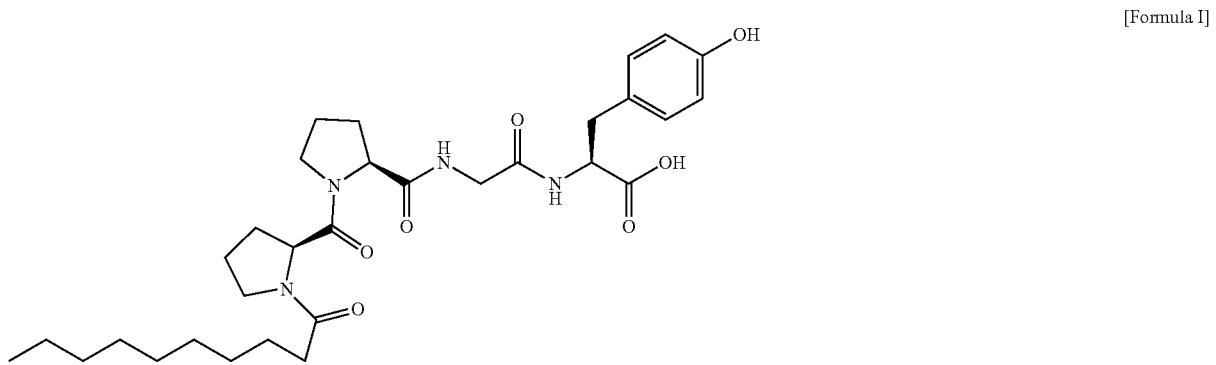

SEQ ID NO: 10
[Formula J]
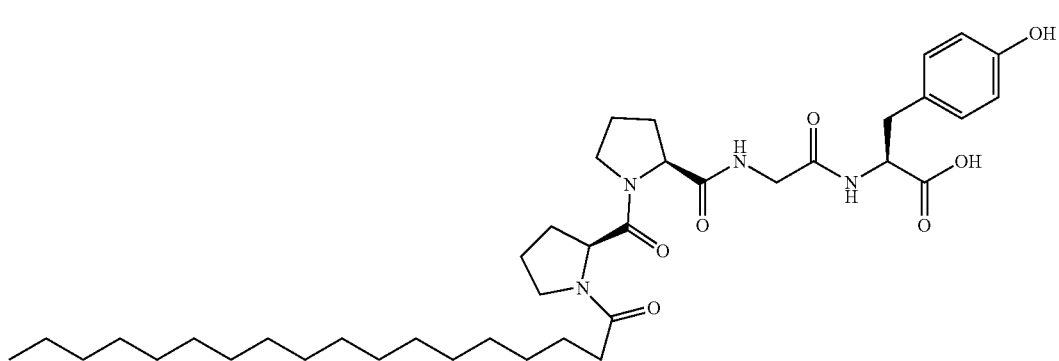
SEQ ID NO: 11
[Formula K]
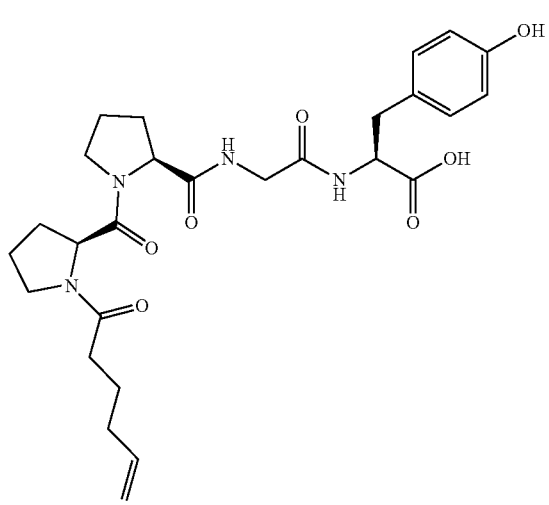
SEQ ID NO: 12
[Formula L]
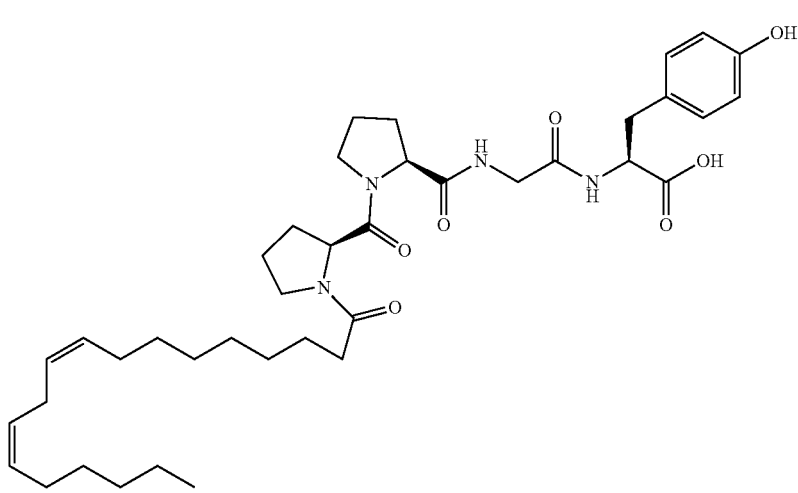

-continued
SEQ ID NO: 13
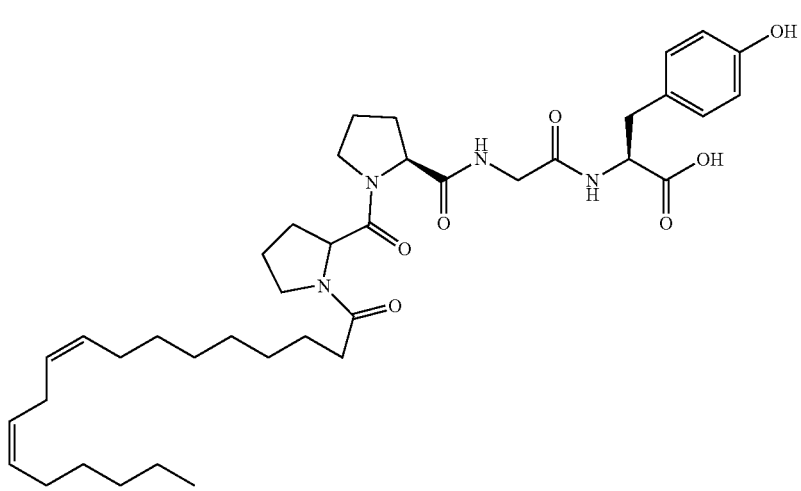
[Formula M]
SEQ ID NO: 14
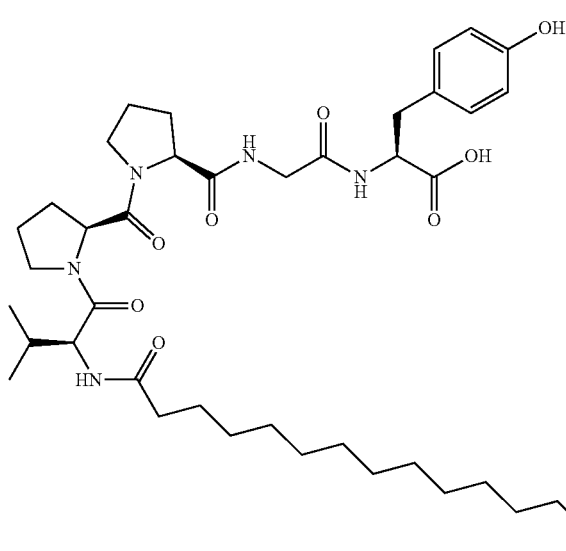
[Formula N]
SEQ ID NO: 15
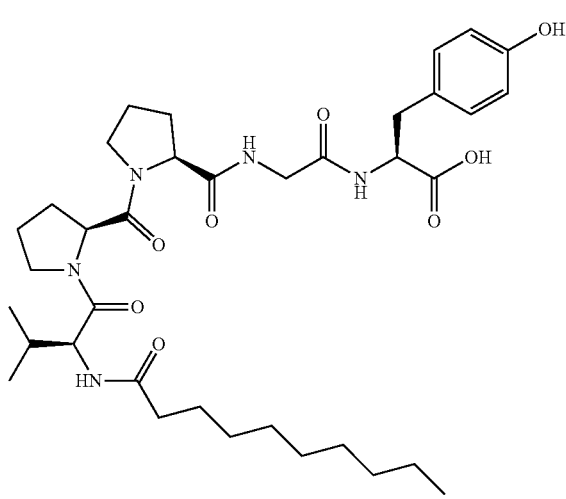
[Formula O]

Compounds according to embodiments of the present invention are effective for preventing or treating various diseases including inflammatory indications, cancers, and ophthalmic indications. More particularly, the compounds are effective for suppressing the expression of cytokines and/or chemokines (e.g., G-CSF, IL-2, SCF, VEGF, CX3CL1, IGFBP5, IGFBP6, IL-1α, IL-1β, IL-6, IL-9, MCP-1, MIP-3α, IL12p40/70, MIG, TNF-α, and VCAM-1). The compounds are also effective for inhibiting decomposition of IκB in inflammation signaling pathway mediated by MyD88 (myddosome complex) and/or RIP 1, thereby preventing NF-κB from being transported into nucleus of a cell. In addition, effective concentration of the compounds in a targeted cell/tissue remains for a sufficient time.

3. Preparation Methods

Another aspect of the present invention provides a method for preparing the compound represented by Formula 1 (SEQ ID NO: 1). The method, as illustrated by the Reaction Scheme 1 shown below, comprises: reacting a compound 2 with a compound 3 to prepare a compound 4 (step 1); hydrolyzing the compound 4 in the presence of a base to prepare a compound 5 (step 2); reacting the compound 5 with a compound 6 to prepare a compound 7 (step 3); hydrolyzing the compound 7 in the presence of a base to prepare a compound 8 (step 4); reacting the compound 8 with a compound 9 to prepare a compound 10 (step 5); hydrolyzing the compound 10 in the presence of a base to prepare the compound of Formula I (SEQ ID NO: 1) (step 6).

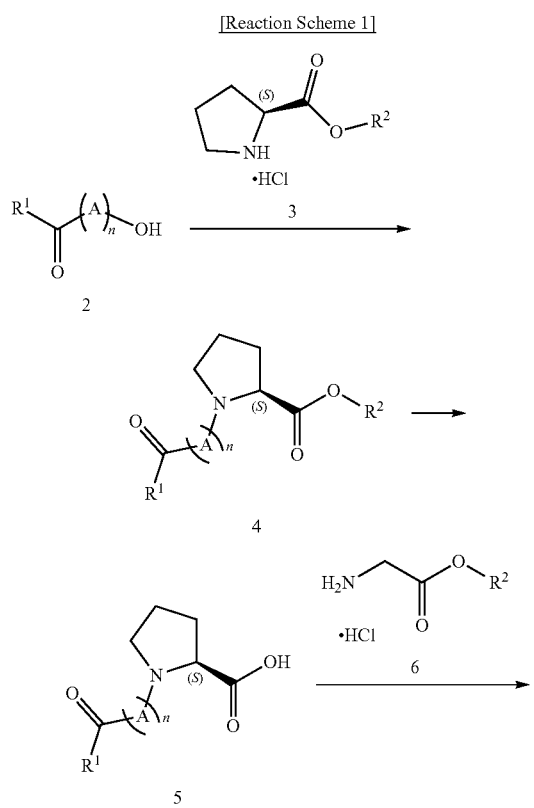

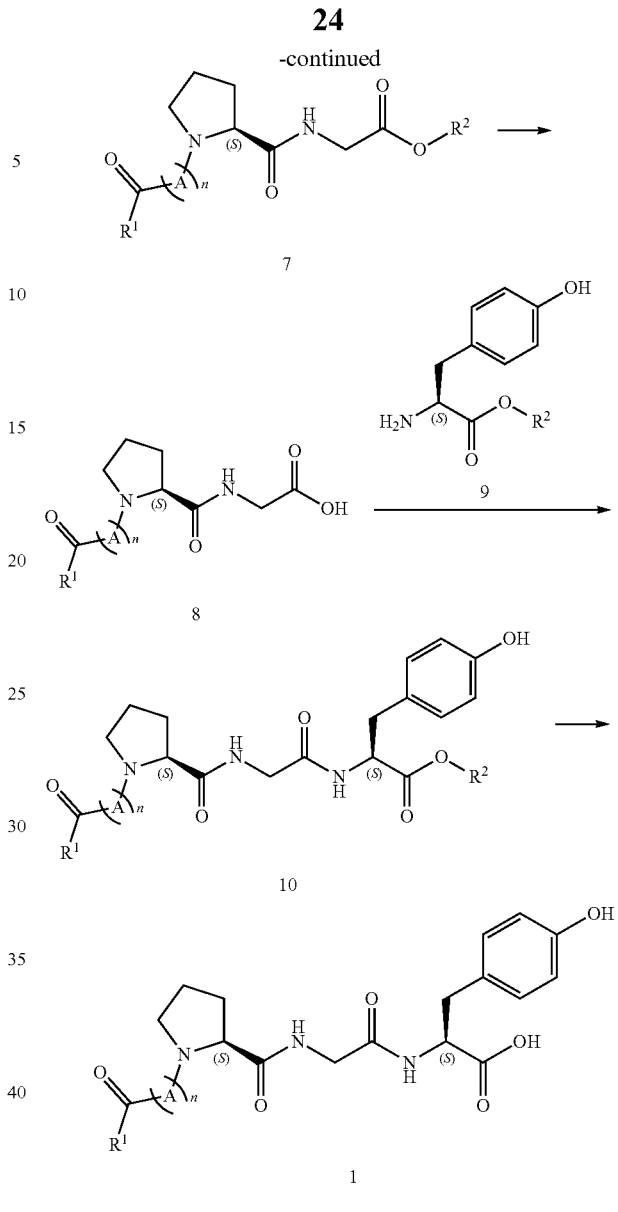

wherein A, $R^1$ and n are the same as defined in claim 1 and $R^2$ is a straight chain or branched chain $C_{1-5}$ alkyl.

In some embodiments, in the step 1, the compound 2 may be coupled with the compound 3 in the presence of 1-ethyl-3-(3-dimethylaminopropyl)carbodiimide (EDCl), hydroxybenzotriazole (HOBt), and a base. The base can be an organic or inorganic base. Non-limiting examples of the organic base include pyridine, triethylamine (TEA), N,N-diisopropylethlyamine (DIPEA), and 1,8-diazabicyclo [5.4.0]unde-7-ene (DBU). Non-limiting examples of the inorganic base include sodium hydroxide, sodium carbonate, potassium carbonate, cesium carbonate, and sodium hydride. These may be used stoichiometric or excess, alone or in combination. Non-limiting examples of the solvent that can be used to react the compound 2 with the compound 3 include an ether (e.g., tetrahydrofuran (THF), dioxane, ethyl ether and 1,2-dimethoxyethane), an alcohol (e.g., methanol, ethanol, propanol, and butanol), dimethylformamide (DMF), dimethylsulfoxide (DMSO), dichloromethane (DCM), dichloroethane, water, acetone, benzenesulfonate, toluensulfonate, chlorobenzenesulfonate, xylenesulfonate, ethylacetate, phenylacetate, phenylpropionate, phenylbutyrate, citrate, lactate, hydroxybutyrate, glycolate, maleate, tartrate, methansulfonate, propanesulfonate, naphthalen-1-sulfonate, naphthalen-2-sulfonate, and mandelate. The solvent can be used alone or in combination.

The base in the step 2 can be an organic or inorganic base. Likewise, non-limiting examples of the organic base that can be used in the step 2 include pyridine, triethylamine, N,N-diisopropylethlyamine (DIPEA), and 1,8-diazabicyclo[5.4.0]unde-7-ene (DBU). Non-limiting examples of the inorganic base include sodium hydroxide, sodium carbonate, potassium carbonate, cesium carbonate, and sodium hydride. These may be used stoichiometric or excess, alone or in combination. Non-limiting examples of the solvent that can be used to react the compound 4 with the compound 5 include an ether (e.g., tetrahydrofuran (THF), dioxane, ethyl ether and 1,2-dimethoxyethane), an alcohol (e.g., methanol, ethanol, propanol, and butanol), dimethylformamide (DMF), dimethylsulfoxide (DMSO), dichloromethane (DCM), dichloroethane, water, acetone, benzenesulfonate, toluensulfonate, chlorobenzenesulfonate, xylenesulfonate, ethylacetate, phenylacetate, phenylpropionate, phenylbutyrate, citrate, lactate, hydroxybutyrate, glycolate, mandelate, tartrate, methansulfonate, propanesulfonate, naphthalen-1-sulfonate, naphthalen-2-sulfonate, and mandelate. The solvent can be used alone or in combination.

The step 3 and the step 5 may be performed in the manner identical or similar to the step 1. The step 4 and the step 6 may be performed in the manner identical or similar to the step 2.

Preparation of Compound 2

Examples of the compound 2 represented by the following Formula 2, which is the starting material of the Reaction Scheme 1, may be prepared by, e.g., the Preparation Method A described below.

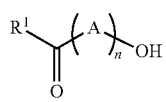

[Formula 2]

wherein n is 0, 1, or 2; A is -a$^1$-, which is an amino acid independently selected from the group consisting of alanine, (Ala, A), arginine (Arg, R), asparagine (Asn, N), aspartic acid (Asp, D), cysteine (Cys, C), glutamic acid (Glu, E), glutamine (Gln, Q), glycine (Gly, G), histidine (His, H), isoleucine (Ile, I), leucine (Leu, L), lysine (Lys, K), methionine (Met, M), phenylalanine (Phe, F), proline (Pro, P), serine (Ser, S), threonine (Thr, T), tryptophan (Trp, W), tyrosine (Tyr, Y), and valine (Val, V), both terminal ends of the amino acid being coupled to a carbonyl group or an amine group by an amide bond; and R$^1$ is a straight chain or branched chain C$_{1-36}$ alkyl, a straight chain or branched chain C$_{2-36}$ alkenyl including at least one double bond, or a straight chain or branched chain C$_{2-36}$ alkynyl including at least one triple bond

[Preparation Method A]

A compound represented by the Formula a shown below is coupled with an amino acid selected from the group consisting of alanine, (Ala, A), arginine (Arg, R), asparagine (Asn, N), aspartic acid (Asp, D), cysteine (Cys, C), glutamic acid (Glu, E), glutamine (Gln, Q), glycine (Gly, G), histidine (His, H), isoleucine (Ile, I), leucine (Leu, L), lysine (Lys, K), methionine (Met, M), phenylalanine (Phe, F), proline (Pro, P), serine (Ser, S), threonine (Thr, T), tryptophan (Trp, W), tyrosine (Tyr, Y), and valine (Val, V) in the presence of 1-ethyl-3-(3-dimethylaminopropyl)carbodiimide, hydroxybenzotriazole, and a base to form an amide bond, thereby preparing the compound 2.

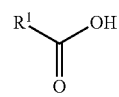

[Formula a]

(R$^1$ is same as defined in Formula 2).

4. Compositions/Formulations

A still another aspect of the present invention provides a composition for preventing, improving, and treating various diseases (e.g., inflammatory indications, cancers, and ophthalmic indications), which composition comprises, as an active component, at least one of the compounds, at least one of the optical isomers, or at least one of the salts.

Compositions in accordance with some embodiments may suppress expression of cytokines and/or chemokines including G-CSF, IL-2, SCF, VEGF, CX3CL1, IGFBP5, IGFBP6, IL-1α, IL-1β, IL-6, IL-9, MCP-1, MIP-3α, IL12p40/70, MIG, TNF-α, and VCAM-1. Compositions in accordance with other embodiments may suppress activity of NF-κB. Compositions in accordance with other embodiments may inhibit formation of an inflammatory signal transduction complex mediated by MyD88. Compositions in accordance with other embodiments may inhibit formation of an inflammatory signal transduction complex mediated by RIP1. Compositions in accordance with other embodiments may inhibit formation of an inflammatory signal transduction complex mediated by Pellino-1.

In some embodiments, the present invention provides a composition for preventing, improving, and treating inflammatory bowel disease (including closely related disorders), which comprises, as an active component, at least one of the compounds, at least one of the optical isomers, or at least one of the salts. The inflammatory bowel disease may include, but are not limited to, ulcerative colitis, Behcet's disease, and Crohn's disease. The composition may further comprise an additive.

In some embodiments, the present invention provides a composition for preventing, improving, or treating multiple sclerosis, psoriasis, sepsis, geographic atrophy, wet age-related macular disease, dry age-related macular disease, diabetic retinopathy, infectious lung diseases, bacterial pneumonia, viral pneumonia, diffuse large B-cell lymphoma, viral infection, autoimmune disease, blood cancer including lymphoma, and tumors in internal organs, which comprises, as an active component, at least one of the compounds, at least one of the optical isomers, or at least one of the salts.

In some embodiments, the present invention provides a composition for preventing, improving, or treating alopecia, which comprises, as an active component, at least one of the compounds, at least one of the optical isomers, or at least one of the salts, wherein the active component inhibits expression of IL-6 in scalp and hair follicles.

The present invention embraces formulations suitable for the administration of the compounds described herein. The compounds described herein can be in formulations (including pharmaceutical compositions) with additives such as excipients (e.g., one or more excipients), antioxidants (e.g., one or more antioxidants), stabilizers (e.g., one or more stabilizers), preservatives (e.g., one or more preservatives), pH adjusting and/or buffering agents (e.g., one or more pH adjusting and/or buffering agents), tonicity adjusting agents (e.g., one or more tonicity adjusting agents), thickening agents (e.g., one or more thickening agents), suspending agents (e.g., one or more suspending agents), binding agents (e.g., one or more binding agents), viscosity-increasing agents (e.g., one or more viscosity-increasing agents), and the like, provided that the additional components are pharmaceutically acceptable for the particular condition to be treated. In some embodiments, the formulation may include combinations of two or more of the additional components as described herein (e.g., 2, 3, 4, 5, 6, 7, 8, or more additional components). In some embodiments, the additives include processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-beta-cyclodextrin, polyvinylpyrrolidinone, low melting waxes, ion exchange resins, and the like, as well as combinations of any two or more thereof. Other suitable pharmaceutically acceptable excipients are described in "Remington's Pharmaceutical Sciences," Mack Pub. Co., New Jersey (1991), and "Remington: The Science and Practice of Pharmacy," Lippincott Williams & Wilkins, Philadelphia, 20th edition (2003) and 21st edition (2005), which are incorporated herein by reference.

Formulations of the pharmaceutical compositions appropriate for administration by any medically acceptable means are included in the invention. The pharmaceutical formulations may comprise a pharmaceutically acceptable carrier appropriate to the means of administration and a pharmaceutically acceptable compound (composition). For example, formulations of the composition described herein may be suitable for oral administration. They can be formed in various forms including solutions, suspensions, semi-liquids, semi-solids, gels, emulsions, ointments, tablets, and creams. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers.

The compositions (formulations) may be administered via many routes including, not limited to, oral, nasal, pulmonary, rectal, buccal, vaginal, ocular, and transdermal routes. The mode, frequency, and effective amount of administration of the compositions (formulations) can be decided according to methods known in the art and/or the methods described herein (e.g., oral administration, 0.1-1,000 mg/day, once a day). For example, they can be administered alone or in combination. For example, they can be concurrently administered, co-administered, and/or intermittently administered.

5. Methods of Using Compounds, Compositions, or Formulations

A further aspect of the present invention provides a method for preventing, improving, or treating various diseases (e.g., inflammatory indications, cancers, and ophthalmic indications), which comprises administering to a subject in need the composition (or compound or formulation described herein).

In an embodiment, the present invention provides a method for preventing, improving, or treating inflammatory bowel disease, which comprises administering the composition (or compound or formulation described herein) to a subject in need a composition containing, as an active component, at least one of the compounds, at least one of the optical isomers, or at least one of the salts.

In another embodiment, the prevent invention provides a method for preventing, improving, or treating disease or syndrome, which method comprises administering to a subject in need a composition containing, as an active component, at least one of the compounds, at least one of the optical isomers, or at least one of the salts. The disease or syndrome may involve formation of a Pellino-1 induced inflammatory signal transduction complex containing MyD88, RIP1, or both. The disease or syndrome may include, but not limited to, multiple sclerosis, psoriasis, sepsis, geographic atrophy, wet age-related macular disease, dry age-related macular disease, diabetic retinopathy, infectious lung diseases, bacterial pneumonia, viral pneumonia, diffuse large B-cell lymphoma, viral infection, autoimmune disease, blood cancer including lymphoma, and tumors in internal organs (e.g., liver, lung, intestine, prostate, pancreas and the like).

In still another embodiment, the prevent invention provides a method for preventing, improving, or treating geographic atrophy, wet age-related macular disease, dry age-related macular disease, or diabetic retinopathy, which method comprises administering to a subject in need a composition containing, as an active component, at least one of the compounds, at least one of the optical isomers, or at least one of the salts. The compound(s), the optical isomer(s), and the salt(s) may have a pharmaceutical effect on retinal pigment epithelium cells. In retinal pigment epithelium cells, they may inhibit expression of at least one protein selected from the group consisting of Nox-4, VEGF, VEGFR1, VEGFR2, Ang2, EPO and EPOR. In retinal pigment epithelium cells, they may increase expression of Ang 1, Tie2, or both.

EXAMPLES

The present invention will be explained in more detail with the following examples. The examples are presented solely for the purpose of illustration of the present invention and the present invention will not be limited to the examples.

Example 1

Preparation of Compounds

Example 1.1

(S)-3-(4-hydroxyphenyl)-2-(2-(2-((S)-1-((S)-1-palmitoylpyrrolidine-2-carbonyl)pyrrolidine-2-carboxamido)acetamido)propanoic acid (Pal-PPGY-OH) (SEQ ID NO: 2)

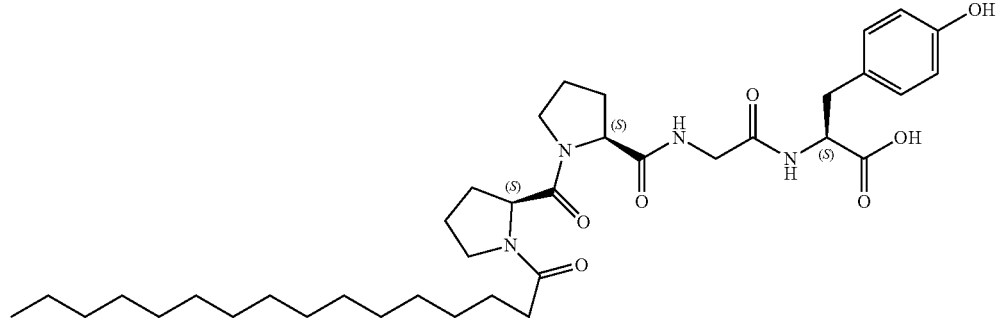

Step 1: Preparation of (S)-methyl 1-((S)-1-palmitoylpyrrolidine-2-carbonyl)pyroliddine-2-carboxylate A mixture solution was made by mixing (S)-1-palmitoylpyrrolidine-2-carboxylic acid (10.0 g, 28.3 mmol) prepared in the step 2 of Example 1.2, EDCl (5.96 g, 31.1 mmol), HOBt (4.20 g, 31.1 mmol), and triethylamine (11.8 mL, 84.9 mmol) in dichloromethane. Proline methyl ester hydrochloride (5.15 g, 31.1 mmol) was added to the mixture solution. The resulting mixture was agitated at room temperature overnight, concentrated under reduced pressure, diluted with sodium bicarbonate aqueous solution, and extracted with ethyl acetate three times. The whole organic layer was washed with saline solution and washed with 1N HCl three times. The resultant was washed with saline solution, dried with anhydrous magnesium sulfate, and concentrated under reduced pressure to obtain (S)-methyl 1-((S)-1-palmitoylpyrrolidine-2-carbonyl)pyrrolidine-2-carboxlate (11.4 g, yield 87%).

$^1$H-NMR (300 MHz, CDCl$_3$) δ 4.69-4.65 (m, 1H), 4.54-4.58 (m, 1H), 3.83-3.93 (m, 1H), 3.58-3.72 (m, 5H), 3.45-3.53 (m, 1H), 1.89-2.31 (m, 10H), 1.60-1.64 (m, 2H), 1.25 (m, 24H), 0.88 (t, J=6.87 Hz, 3H).

MS (ESI), calcd for $C_{27}H_{48}N_2O_4$ 464.4, found m/z465.2 (M+H$^+$).

Step 2: Preparation of (S)-1-((S)-1-palmitoylpyrrolidine-2-carbonyl)pyrrolidine-2-carboxylic Acid (S)-methyl 1-((S)-1-palmitoylpyrrolidine-2-carbonyl)pyrrolidine-2-carboxlate (15.0 g, 32.3 mmol) prepared in the step 1 was mixed with tetrahydrofuran. Sodium hydroxide (2.58 g, 64.6 mmol) aqueous solution was added to the mixture solution. The resulting mixture was agitated at room temperature overnight and concentrated. 1N HCl was added to adjust the pH to 1.0. The aqueous layer thereof was extracted with ethyl acetate three times. The whole organic layer was dried with anhydrous magnesium sulfate and concentrated to obtain (S)-1-((S)-1-palmitoylpyrrolidine-2-carbonyl)pyrrolidine-2-carboxylic acid (13.2 g, yield 91%) as white solid.

MS (ESI), calcd for $C_{26}H_{46}N_2O_4$ 450.3, found m/z451.1 (M+H$^+$).

Step 3: Preparation of ethyl 2-((S)-1-((S)-1-palmitoylpyrrolidine-2-carbonyl)pyrrolidine-2-carboxamido)acetate (S)-1-((S)-1-palmitoylpyrrolidine-2-carbonyl)pyrrolidine-2-carboxylic acid (12 g, 26.6 mmol) prepared in the step 2 was mixed with dichloromethane. Glycine ethyl ester hydrochloride (4.09 g, 29.3 mmol), EDCl (5.62 g, 29.3 mmol), HOBt (3.96 g, 29.3 mmol) and triethyamine (11.1 mL, 79.8 mmol) were added to the mixture solution. The resulting mixture was agitated at room temperature overnight, concentrated under reduced pressure, diluted with sodium carbonate aqueous solution, and extracted with ethyl acetate three times. The whole organic layer was washed with saline solution and washed with 1N HCl three times. The organic layer was washed with saline solution, dried with anhydrous magnesium sulfate, and concentrated to obtain ethyl 2-((S)-1-((S)-1-palmitoylpyrrolidine-2-carbonyl)pyrrolidine-2-carboxyamido)acetate (11.1 g, yield 78%).

MS (ESI), calcd for $C_{30}H_{53}N_3O_5$ 535.4, found m/z536.5 (M+H$^+$).

Step 4: Preparation of 2-((S)-1-((S)-1-palmitoylpyrrolidine-2-carbonyl)pyrrolidine-2-carboxamido)acetic Acid Ethyl 2-((S)-1-((S)-1-palmitoylpyrrolidine-2-carbonyl)pyrrolidine-2-carboxyamido)acetate (12 g, 22.4 mmol) prepared in the step 3 was mixed with tetrahydrofuran. Sodium hydroxide (1.79 g, 44.8 mmol) aqueous solution was added to the mixture solution. The resulting mixture was agitated at room temperature overnight and concentrated. 1N HCl was added to adjust the pH to 1.0. The aqueous layer was extracted with ethyl acetate three times. The whole organic layer was dried with anhydrous magnesium sulfate and concentrated to obtain 2-((S)-1-((S)-1-palmitoylpyrrolidine-2-carbonyl)pyrrolidine-2-carboxamido)acetic acid (9.5 g, yield 84%).

MS (ESI), calcd for $C_{28}H_{49}N_3O_5$ 507.4, found m/z508.2 (M+H$^+$).

Step 5: Preparation of (S)-methyl 3-(4-hydroxyphenyl)-2-(2-((S)-1-((S)-1-palmitoylpyrrolidine-2-carbonyl)pyrrolidine-2-carboxamido)acetamido)propanoate 2-((S)-1-((S)-1-palmitoylpyrrolidine-2-carbonyl)pyrrolidine-2-carboxamido)acetic acid (10 g, 19.7 mmol) prepared in the step 4 was mixed with dichloromethane. Tyrosine methyl ester (4.23 g, 21.7 mmol), EDCl (4.16 g, 21.7 mmol), HOBt (21.7 g, 21.7 mmol), and triethylamine (8.19 mL, 59.1 mmol) were added to the mixture solution. The resulting mixture was agitated at room temperature overnight, concentrated under reduced pressure, diluted with sodium bicarbonate aqueous solution, and extracted with ethyl acetate three times. The whole organic layer was washed with saline solution and washed with 1N HCl three times. The organic layer was washed with saline solution, dried with anhydrous magnesium sulfate, concentrated, and purified with MPLC to obtain (S)-methyl 3-(4-hydroxyphenyl)-2-(2-((S)-1-((S)-1-palmitoylpyrrolidine-2-carbonyl)pyrrolidine-2-carboxamido)acetamido)propanoate (8.4 g, yield 62%).

MS (ESI), calcd for $C_{37}H_{60}N_4O_7$684.4, found m/z685.2 (M+H$^+$).

Step 6: Preparation of (S)-3-(4-hydroxyphenyl)-2-(2-((S)-1-((S)-1-palmitoylpyrrolidine-2-carbonyl)pyrrolidine-2-carboxamido)acetamido)propanoic Acid (S)-methyl 3-(4-hydroxyphenyl)-2-(2-((S)-1-((S)-1-palmitoylpyrrolidine-2-carbonyl)pyrrolidine-2-carboxamido)acetamido)propanoate (4.9 g, 7.16 mmol) prepared in the step 5 was mixed with tetrahydrofuran. Sodium hydroxide (0.86 g, 21.5 mmol) aqueous solution was added to the mixture solution. The resulting mixture was agitated at room temperature overnight and concentrated. 1N HCl was added to adjust the pH to 1.0. The aqueous layer was extracted with ethyl acetate three times. The whole organic layer was dried with anhydrous magnesium sulfate and concentrated to obtain (S)-3-(4-hydroxyphenyl)-2-(2-((S)-1-((S)-1-palmitoylpyrrolidine-2-carbonyl)pyrrolidine-2-carboxamido)acetamido)propanoic acid (SEQ ID NO: 2) (4.5 g, yield 93%).

$^1$H-NMR (300 MHz, MeOD) δ 7.04 (d, J=8.31 Hz, 2H) 6.70 (d, J=8.37 Hz, 2H), 4.38-4.68 (m, 3H), 3.44-4.04 (m, 6H), 2.91-3.13 (m, 2H), 1.81-2.38 (m, 10H), 1.54-1.60 (m, 2H), 1.30 (m, 24H), 0.88 (t, J=6.63 Hz, 3H).

MS (ESI), calcd for $C_{37}H_{58}N_4O_7$670.4, found m/z671.3 (M+H$^+$).

Example 1.2

(S)-3-(4-hydroxyphenyl)-2-(2-((S)-1-palmitoylpyrrolidine-2-carboxamido)acetamido)propanoic acid (Pal-PGY-OH)

Step 1: (S)-methyl 1-palmitoylpyrrolidine-2-carboxylate

Palmitic acid (7 g, 27.3 mmol), EDCl (5.78 g, 30.0 mmol), HOBt (4.05 g, 30.0 mmol), and, triethylamine (11.4 mL, 81.9 mmol) were mixed with dichloromethane. Proline methyl ester hydrochloride (4.97 g, 30.0 mmol) was added to the mixture solution. The resulting mixture was agitated at room temperature overnight, concentrated under reduced pressure, diluted with sodium carbonate aqueous solution, and extracted with ethyl acetate three times. The whole organic layer was washed with saline solution and washed with 1N HCl three times. The organic layer was washed with saline solution, dried with anhydrous magnesium sulfate, and concentrated under reduced pressure to obtain (S)-methyl 1-palmitoylpyrrolidine-2-carboxylate (9.6 g, yield 96%) as viscous liquid.

$^1$H-NMR (300 MHz, CDCl$_3$) δ 4.46-4.50 (m, 1H), 3.47-3.75 (m, 5H), 1.90-2.36 (m, 6H), 1.59-1.69 (m, 2H), 1.25 (m, 24H), 0.88 (t, J=6.84 Hz, 3H)

MS (ESI), calcd for $C_{22}H_{41}NO_3$367.3, found m/z368 (M+H$^+$).

Step 2: Preparation of (S)-1-palmitoylpyrrolidine-2-carboxylic Acid (S)-methyl 1-palmitoylpyrrolidine-2-carboxylate (10.0 g, 27.2 mmol) prepared in the step 1 was mixed with tetrahydrofuran. Sodium hydroxide (3.26 g, 81.6 mmol) aqueous solution was added to the mixture solution. The resulting mixture was agitated at room temperature overnight and concentrated. 1N HCl was added to adjust the pH to 1.0. The aqueous layer was extracted with ethyl acetate three times. The whole organic layer was dried with anhydrous magnesium sulfate and concentrated to obtain (S)-1-palmitoylpyrrolidine-2-carboxylic acid (8.6 g, yield 89%) as white solid.

$^1$H-NMR (300 MHz, CDCl$_3$) δ 4.59-62 (m, 1H), 3.42-3.59 (m, 2H), 2.46-2.53 (m, 1H), 2.33-2.38 (m, 2H), 1.93-2.01 (m, 3H), 1.62-1.69 (m, 2H), 1.25 (m, 24H), 0.88 (t, J=6.90 Hz, 3H)

MS (ESI), calcd for $C_{21}H_{39}NO_3$353.3, found m/z354.2 (M+H$^+$).

Step 3: preparation of (S)-ethyl 2-(1-palmitoylpyrrolidine-2-carboxamido)acetate (S)-1-palmitoylpyrrolidine-2-carboxylic acid (10 g, 28.3 mmol) prepared in the step 2, glycine ethyl ester hydrochloride (4.34 g, 31.1 mmol), EDCl (5.76 g, 31.1 mmol), HOBt (4.20 g, 31.1 mmol), and triethyamine (1, 5.7 mL, 113 mmol) were mixed with dichloromethane. The resulting mixture was agitated at room temperature overnight, concentrated under reduced pressure, diluted with sodium carbonate aqueous solution, and extracted with ethyl acetate three times. The whole organic layer was washed with saline solution and washed with 1N HCl three times. The organic layer was washed with saline solution, dried with anhydrous magnesium sulfate, and concentrated to obtain (S)-ethyl 2-(1-palmitoylpyrrolidine-2-carboxamido)acetate (10.7 g, yield 86%).

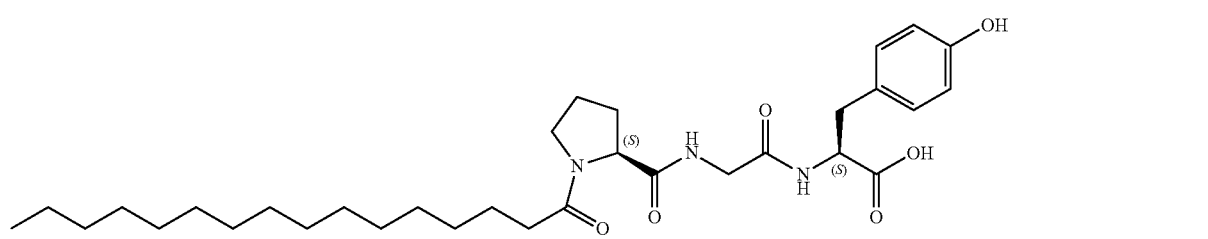

MS (ESI), calcd for $C_{25}H_{46}N_2O_4$ 438.3, found m/z 439.1 (M+H$^+$).

Step 4: Preparation of (S)-2-(1-palmitoylpyrrolidine-2-carboxamido)acetic Acid (S)-ethyl 2-(1-palmitoylpyrrolidine-2-carboxamido)acetate (12 g, 27.4 mmol) prepared in the step 3 was mixed with tetrahydrofuran. Sodium hydroxide (2.20 g, 54.7 mmol) aqueous solution was added to the mixture solution. The resulting mixture was agitated at room temperature overnight and concentrated. 1N HCl was added to adjust the pH to 1.0. The aqueous layer was extracted with ethyl acetate three times. The whole organic layer was dried with anhydrous magnesium sulfate and concentrated to obtain (S)-2-(1-palmitoylpyrrolidine-2-carboxamido)acetic acid (10.2 g, yield 91%) as white solid.

MS (ESI), calcd for $C_{23}H_{42}N_2O_4$ 410.3, found m/z 411.3 (M+H$^+$).

Step 5: Preparation of (S)-methyl 3-(4-hydroxyphenyl)-2-(2-((S)-1-palmitoylpyrrolidine-2-carboxamido)acetamido)propanoate (S)-2-(1-palmitoylpyrrolidine-2-carboxamido)acetic acid (7 g, 27.3 mmol) prepared in the step 4 was mixed with dichloromethane. Tyrosine methyl ester (5.86 g, 30.0 mmol), EDCl (5.78 g, 30.0 mmol), HOBt (4.05 g, 30.0 mmol), and triethylamine (11.4 mL, 81.9 mmol) were added to the mixture solution. The resulting mixture was agitated at room temperature overnight, concentrated under reduced pressure, diluted with sodium bicarbonate aqueous solution, and extracted with ethyl acetate three times. The whole organic layer was washed with saline solution and washed with 1N HCl three times. The organic layer was washed with saline solution, dried with anhydrous magnesium sulfate, concentrated, and purified with MPLC to obtain (S)-methyl 3-(4-hydroxyphenyl)-2-(2-((S)-1-palmitoylpyrrolidine-2-carboxamido)acetamido)propanoate (9.8 g, yield 61%).

$^1$H-NMR (300 MHz, CDCl$_3$) δ 7.25-7.50 (m, 3H), 6.93 (d, J=8.34 Hz, 2H) 6.70 (d, J=8.34 Hz, 2H), 4.70-4.77 (m, 1H), 4.39-4.43 (m, 1H), 3.95-4.21 (m, 1H), 3.41-3.72 (m, 5H), 2.92-3.12 (m, 2H), 1.91-2.35 (m, 7H), 1.57-1.61 (m, 2H), 1.25 (m, 24H), 0.88 (t, J=6.87 Hz, 3H)

MS (ESI), calcd for $C_{33}H_{53}N_3O_6$ 587.4, found m/z 588.1 (M+H$^+$).

Step 6: Preparation of (S)-3-(4-hydroxyphenyl)-2-(2-((S)-1-palmitoylpyrrolidine-2-carboxamido)acetamido)propanoic Acid (S)-methyl 3-(4-hydroxyphenyl)-2-(2-((S)-1-palmitoylpyrrolidine-2-carboxamido)acetamido)propanoate (2.85 g, 4.85 mmol) prepared in the step 5 was mixed with tetrahydrofuran. Sodium hydroxide (0.58 g, 14.6 mmol) aqueous solution was added to the mixture solution. The resulting mixture was agitated at room temperature overnight and concentrated. 1N HCl was added to adjust the pH to 1.0. The aqueous layer was extracted with ethyl acetate three times. The whole organic layer was dried with anhydrous magnesium sulfate and concentrated to obtain (S)-3-(4-hydroxyphenyl)-2-(2-((S)-1-palmitoylpyrrolidine-2-carboxamido)acetamido)propanoic acid (2.2 g, yield 79%) as white solid.

$^1$H-NMR (300 MHz, MeOD) δ 7.03 (d, J=8.40 Hz, 2H) 6.70 (d, J=8.40 Hz, 2H), 4.58-4.61 (m, 1H), 4.33-4.56 (m, 1H), 3.58-4.37 (m, 4H), 2.96-3.15 (m, 2H), 1.92-2.39 (m, 6H), 1.55-1.62 (m, 2H), 1.29 (m, 24H), 0.91 (t, J=6.87 Hz, 3H) MS (ESI), calcd for $C_{32}H_{51}N_3O_6$ 573.4, found m/z 574.2 (M+H$^+$).

Example 1.3

Palmitoyl-L-alanyl-L-prolylglycyl-L-tyrosine (pal-APGY-OH)(SEQ ID NO: 3)

The compound was prepared according to the following Reaction Scheme 2.

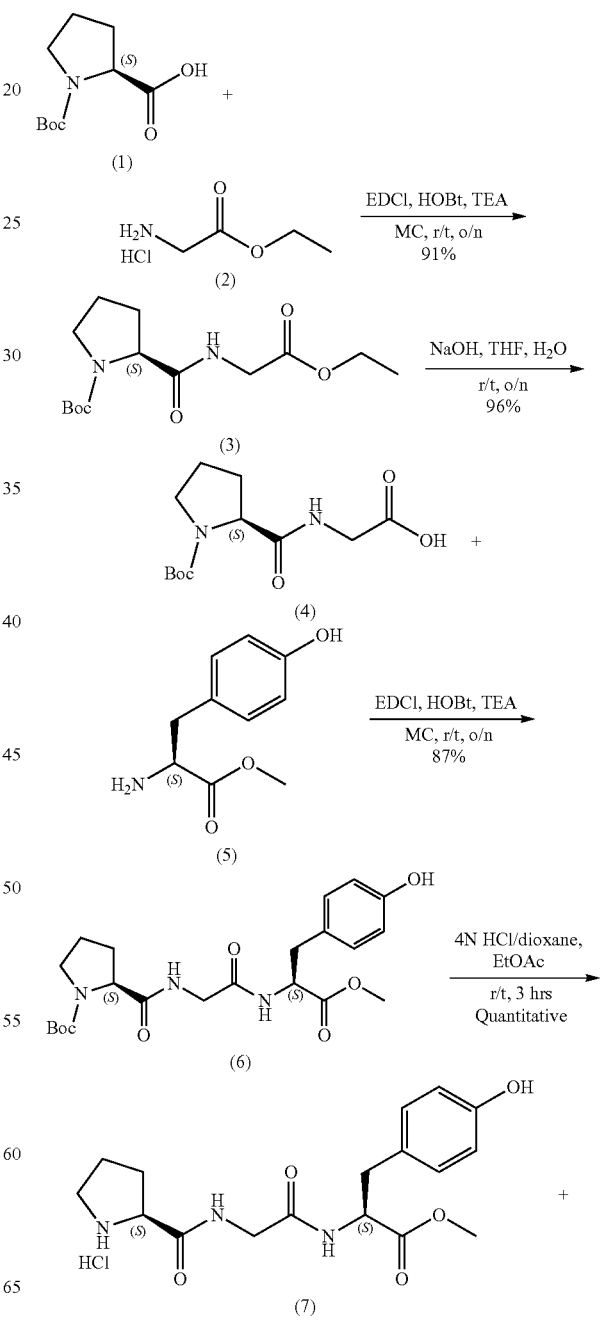

[Reaction Scheme 2]

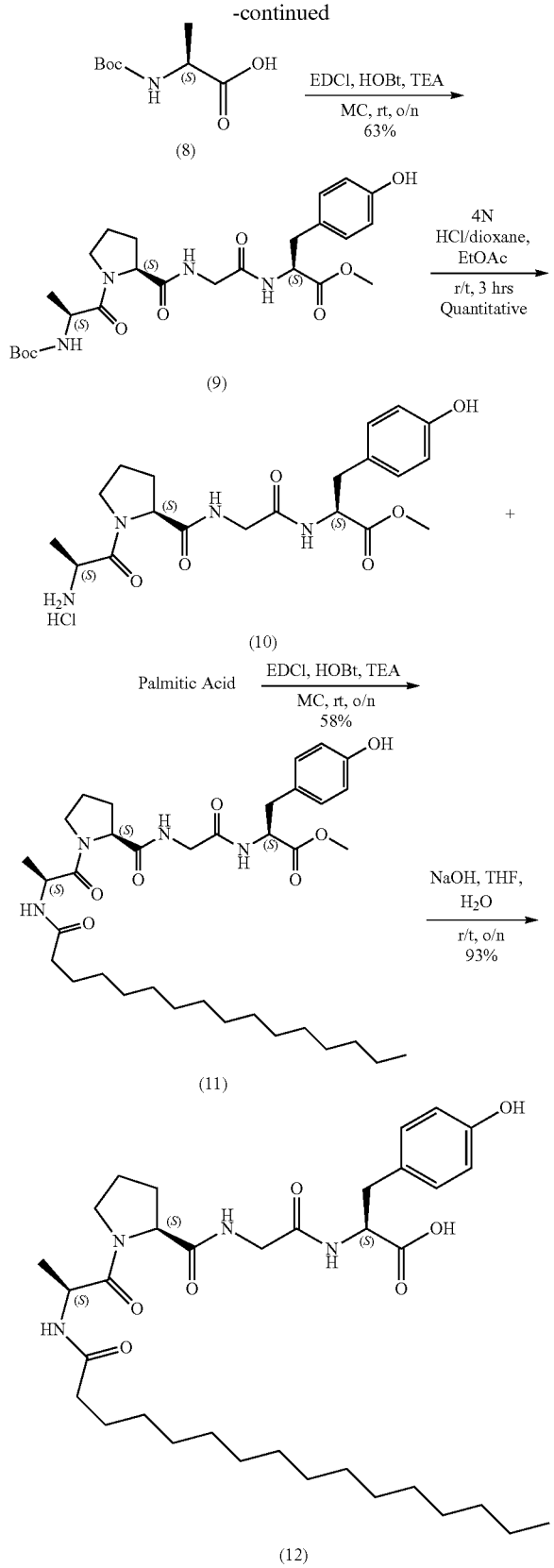

were mixed with dichloromethane. The resulting mixture was agitated at room temperature overnight, concentrated under reduced pressure, diluted with sodium carbonate aqueous solution, and extracted with ethyl acetate three times. The whole organic layer was washed with saline solution and washed with 1N HCl three times. The organic layer was washed with saline solution, dried with anhydrous magnesium sulfate, and concentrated under reduced pressure to obtain the compound (3) (yield 91%) as viscous liquid.

LC-MS (ESI): calcd for $C_{14}H_{24}N_2O_5$ 300.2, found m/z 301.2 (M+H$^+$).

The compound (3) (12 g, 40 mmol) was mixed with tetrahydrofuran. Sodium hydroxide (6.40 g, 160 mmol) aqueous solution was added to the mixture solution. The resulting mixture was agitated at room temperature overnight and concentrated. 1N HCl was added to adjust the pH to 1.0. The aqueous layer was extracted with ethyl acetate three times. The whole organic layer was dried with anhydrous magnesium sulfate and concentrated to obtain the compound (4) (yield 96%) as white solid.

LC-MS (ESI): calcd for $C_{12}H_{20}N_2O_5$ 272.1, found m/z 273.1 (M+H$^+$).

The compound (4) (6.25 g, 23 mmol), the compound (5) (4.85 g, 25.3 mmol), EDCl.HCl (4.85 g, 25.3 mmol), HOBt (43.42 g, 25.3 mmol), and triethylamine (TEA, 12.8 mL, 96 mmol) were mixed with dichloromethane. The resulting mixture was agitated at room temperature overnight, concentrated under reduced pressure, diluted with sodium carbonate aqueous solution, and extracted with ethyl acetate three times. The whole organic layer was washed with sodiumbicarbonate aqueous solution twice, washed with saline solution, and washed with 1N HCl three times. The organic layer was washed with saline solution, dried with anhydrous magnesium sulfate, and concentrated to obtain the compound (6) (yield 87%) as white solid.

LC-MS (ESI): calcd for $C_{22}H_{31}N_3O_7$ 449.2, found m/z 450.2 (M+H$^+$).

The compound (6) (8 g, 17.8 mmol) was dissolved in ethyl acetate. An excess amount of 4 N HCl in dioxane was added at room temperature. The resulting mixture was agitated at room temperature for 4 hours and concentrated under reduced pressure to obtain the compound (7) as white solid.

LC-MS (ESI): calcd for $C_{17}H_{23}N_3O_5$ 349.2, found m/z 350.2 (M+H$^+$).

The compound (7) (0.25 g, 0.65 mmol), the compound (8) (Boc-alanine, 0.12 g, 0.65 mmol), EDCl.HCl (0.25 g, 1.30 mmol), HOBt (0.18 g, 1.30 mmol), and triethylamine (0.36 mL, 2.60 mmol) were mixed with dichlromethane. The resulting mixture was agitated at room temperature overnight, concentrated under reduced pressure, diluted with sodium carbonate aqueous solution, and extracted with ethyl acetate three times. The whole organic layer was washed with sodium bicarbonate aqueous solution twice, washed with saline solution, and washed with 1N HCl three times. The organic layer was washed with saline solution, dried with anhydrous magnesium sulfate, concentrated, and purified by using MPLC (dichloromethane/2-propanol) to obtain the compound (9) (yield 3%).

LC-MS (ESI): calcd for $C_{25}H_{36}N_4O_8$ 520.3, found m/z 520.7 (M+H$^+$).

The compound (9) (0.11 g, 0.21 mmol) was dissolved in ethyl acetate. An excess amount of 4 N HCl in dioxane was added at room temperature and agitated at room temperature for 4 hours. The resulting mixture was concentrated under reduced pressure to obtain the compound (10) as white solid.

LC-MS (ESI): calcd for $C_{20}H_{28}N_4O_6$ 420.2, found m/z 420.6 (M+H$^+$).

The compound (1) (10 g, 46.5 mmol), the compound (2) (7.15 g, 51.2 mmol), EDCl.HCl (9.82 g, 51.2 mmol), HOBt (6.92 g, 51.2 mmol), and triethylamine (19.4 mL, 140 mmol)

To a solution of palmitic acid (0.02 g, 0.08 mmol) in dichloromethane was added compound (10) (0.04 g, 0.09 mmol), EDCl.HCl (0.03 g, 0.16 mmol), HOBt (0.02 g, 0.16 mmol), and triethylamine (0.04 mL, 0.32 mmol). The resultant was was agitated at room temperature overnight, concentrated under reduced pressure, diluted with sodium carbonate aqueous solution, and extracted with ethyl acetate three times. The whole organic layer was washed with saline solution, and washed with 1N HCl three times. The organic layer was washed with saline solution, dried with anhydrous magnesium sulfate, concentrated, and purified by using MPLC (dichloromethane/2-propanol) to obtain the compound (11) (yield 58%).

LC-MS (ESI): calcd for $C_{36}H_{58}N_4O_7$ 658.4, found m/z 659.1 (M+H$^+$)

The compound (11) (0.03 g, 0.05 mmol) was mixed with tetrahydrofuran. Sodium hydroxide (0.008 g, 0.20 mmol) aqueous solution was added. The resulting mixture was agitated at room temperature overnight and concentrated. 1N HCl was added to adjust the pH to 1.0. The aqueous layer was extracted with ethyl acetate three times. The whole organic layer was dried with anhydrous magnesium sulfate and concentrated to obtain the compound (12) (yield 93%) as white solid.

$^1$H NMR (500 MHz, CD$_3$OD) δ 7.05 (d, J=8.50 Hz, 2H), 6.70 (d, J=8.50 Hz, 2H), 4.59-4.65 (m, 2H), 4.39-4.41 (m, 1H), 3.96-3.99 (m, 1H), 3.84-3.89 (m, 1H), 3.65-3.76 (m, 2H), 3.10-3.14 (m, 1H), 2.97-3.01 (m, 1H), 2.20-2.24 (m, 3H), 2.09-2.14 (m, 1H), 1.96-2.03 (m, 2H), 1.58-1.60 (m, 3H), 1.31-1.36 (m, 30H), 0.92 (t, J=7.15 Hz, 3 H). LC-MS (ESI): calcd for $C_{35}H_{56}N_4O_7$ 644.4, found m/z 644.6 (M+H$^+$).

Compounds of Examples 1.4 through 1.15 were prepared in the same manner as described in Example 1.3, using the compound (7) as the starting material. NMR data of those compounds are shown below.

Example 1.4

Palmitoylglycyl-L-prolylglycyl-L-tyrosine
(pal-GPGY-OH)(SEQ ID NO: 4)

$^1$H NMR (500 MHz, CD$_3$OD) δ 7.03 (d, J=8.50 Hz, 2H), 6.70 (d, J=8.50 Hz, 2H), 4.58-4.63 (m, 1H), 4.39-4.42 (m, 1H), 3.90-4.08 (m, 4H), 3.59-3.74 (m, 3H), 3.09-3.12 (m, 1H), 2.96-3.00 (m, 1H), 1.99-2.31 (m, 7H), 1.56-1.66 (m, 3H), 1.24-1.35 (m, 26H), 0.92 (t, J=7.05 Hz, 3H). LC-MS (ESI): calcd for $C_{34}H_{54}N_4O_7$ 630.4, found m/z 630.8 (M+H$^+$).

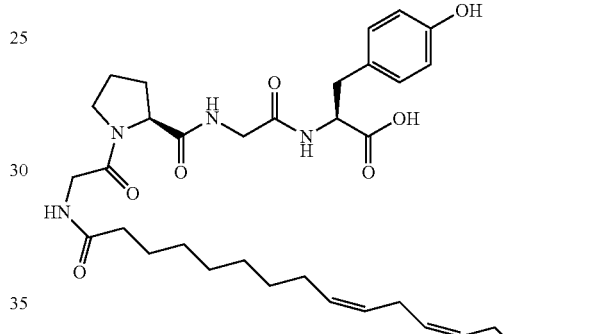

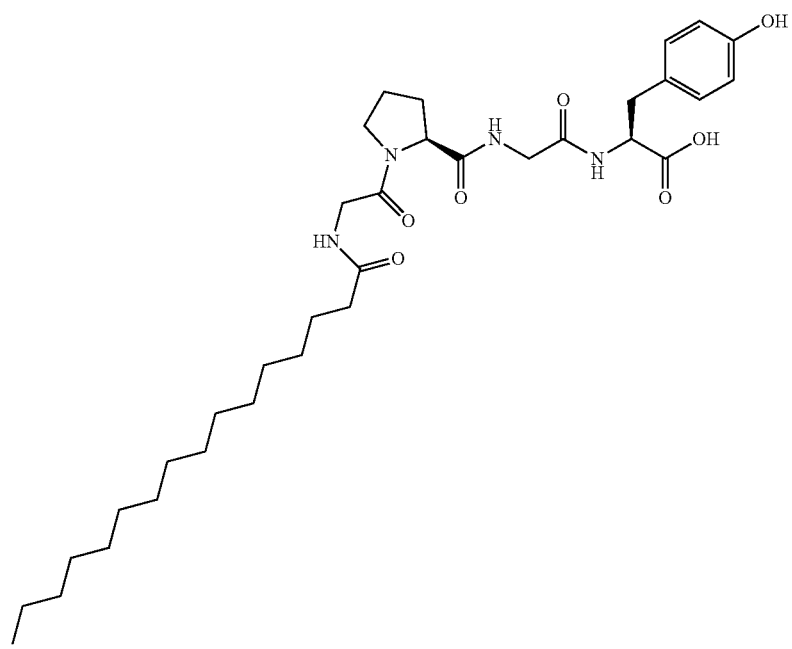 [SMILES: CCCCCCCCCCCCCCCC(=O)NCC(=O)N1CCC[C@H]1C(=O)NCC(=O)N[C@@H](Cc1ccc(O)cc1)C(=O)O]

Example 1.5

((9Z,12Z)-octadeca-9,12-dienoyl)glycyl-L-pro-
lylglycyl-L-tyrosine (linoleyl-GPGY-OH)(SEQ ID
NO: 5)

$^1$H NMR (500 MHz, CD$_3$OD) δ 7.03 (d, J=8.50 Hz, 2H), 6.71 (d, J=8.50 Hz, 2H), 5.31-5.41 (m, 4H), 4.58-4.62 (m, 1H), 4.39-4.42 (m, 1H), 3.99-4.08 (m, 2H), 3.70-3.73 (m, 1H), 3.59-3.67 (m, 1H), 3.09-3.12 (m, 1H), 2.96-3.00 (m, 1H), 2.78-2.79 (m, 3H), 2.25-2.31 (m, 1H), 2.18-2.22 (m, 2H), 1.99-2.13 (m, 7H), 1.56-1.64 (m, 3H), 1.31-1.42 (m, 18H), 0.93 (t, J=7.10 Hz, 3H). LC-MS (ESI): calcd for C$_{36}$H$_5$N$_4$O$_7$ 654.4, found m/z 655 (M+H$^+$).

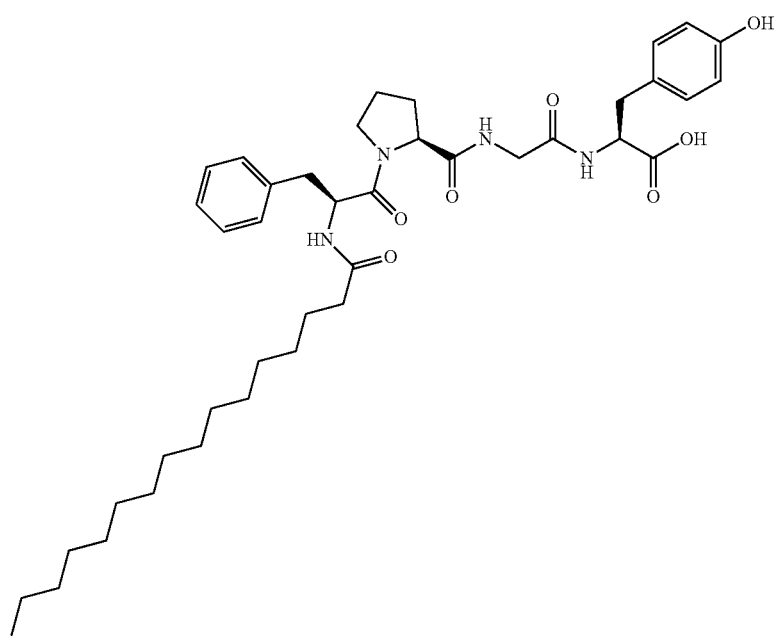 [SMILES: CCCCCCCCCCCCCCCC(=O)N[C@@H](Cc1ccccc1)C(=O)N1CCC[C@H]1C(=O)NCC(=O)N[C@@H](Cc1ccc(O)cc1)C(=O)O]

Example 1.6

Palmitoyl-L-phenylalanyl-L-prolylglycyl-L-tyrosine
(pal-FPGY-OH)(SEQ ID NO: 6)

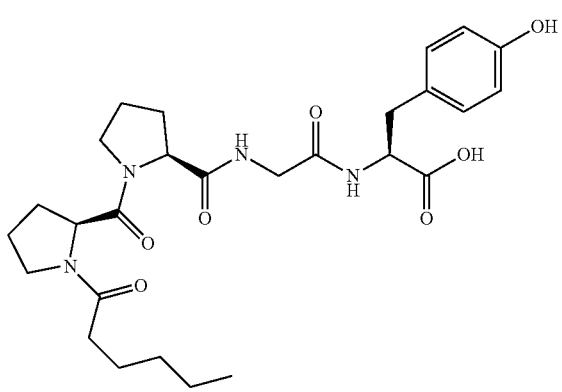 [SMILES: CCCCCC(=O)N1CCC[C@H]1C(=O)N1CCC[C@H]1C(=O)NCC(=O)N[C@@H](Cc1ccc(O)cc1)C(=O)O]

$^1$H NMR (500 MHz, CD$_3$OD) δ 7.27-7.28 (m, 5H), 7.07 (d, J=8.45 Hz, 2H), 6.71 (d, J=8.30 Hz, 2H), 4.59-4.63 (m, 1H), 4.40-4.42 (m, 1H), 3.99-4.02 (m, 1H), 3.85-3.89 (m, 1H), 3.73-3.78 (m, 1H), 3.52-3.55 (m, 1H), 3.09-3.16 (m, 2H), 2.86-3.02 (m, 3H), 1.95-2.22 (m, 8H), 1.44-1.62 (m, 4H), 1.31 (m, 25H), 0.92 (t, J=7.10 Hz, 3H). LC-MS (ESI): calcd for C$_{41}$H$_{60}$N$_4$O$_7$ 720.4, found m/z 721.1 (M+Hf).

Example 1.7

Hexanoyl-L-prolyl-L-prolylglycyl-L-tyrosine (hexanoyl-PPGY-OH)(SEQ ID NO: 7)

$^1$H NMR (500 MHz, CD$_3$OD) δ 7.05 (d, J=8.50 Hz, 2H), 6.70 (d, J=8.50 Hz, 2H), 4.66-4.68 (m, 1H), 4.54-4.57 (m, 1H), 4.40-4.44 (m, 1H), 3.96-4.00 (m, 1H), 3.85-3.89 (m, 1H), 3.73-3.76 (m, 1H), 3.51-3.68 (m, 3H), 3.08-3.12 (m, 1H), 2.97-3.02 (m, 1H), 2.31-2.41 (m, 2H), 2.20-2.29 (m, 2H), 1.92-2.12 (m, 5H), (m, 8H), 1.57-1.66 (m, 3H), 1.31-1.38 (m, 5H), 0.93 (t, J=7.00 Hz, 3H). LC-MS (ESI): calcd for C$_{27}$H$_{38}$N$_4$O$_7$ 530.3, found m/z 530.7 (M+H$^+$).

Example 1.9

Decanoyl-L-prolyl-L-prolylglycyl-L-tyrosine (decanoyl-PPGY-OH)(SEQ ID NO: 9)

$^1$H NMR (500 MHz, CD$_3$OD) δ 7.03 (d, J=8.55 Hz, 2H), 6.71 (d, J=8.40 Hz, 2H), 4.66-4.68 (m, 1H), 4.54-4.57 (m, 1H), 4.40-4.42 (m, 1H), 3.96-4.00 (m, 1H), 3.85-3.89 (m, 1H), 3.73-3.77 (m, 1H), 3.51-3.68 (m, 3H), 3.08-3.12 (m, 1H), 2.97-3.02 (m, 1H), 2.18-2.39 (m, 5H), 1.92-2.14 (m, 6H), 1.57-1.61 (m, 2H), 1.32-1.36 (m, 14H), 0.92 (t, J=7.15 Hz, 3H). LC-MS (ESI): calcd for C$_{31}$H$_{46}$N$_4$O$_7$ 586.3, found m/z 586.8 (M+H$^+$).

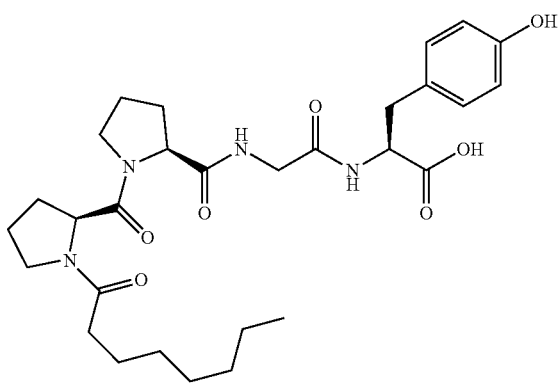 [SMILES: CCCCCCCC(=O)N1CCC[C@H]1C(=O)N1CCC[C@H]1C(=O)NCC(=O)N[C@@H](Cc1ccc(O)cc1)C(=O)O]

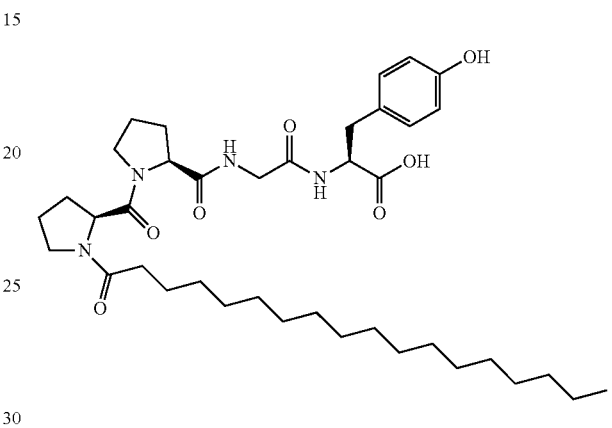

Example 1.8

Octanoyl-L-prolyl-L-prolylglycyl-L-tyrosine (octanoyl-PPGY-OH)(SEQ ID NO: 8)

$^1$H NMR (500 MHz, CD$_3$OD) δ 7.05 (d, J=8.50 Hz, 2H), 6.71 (d, J=8.50 Hz, 2H), 4.66-4.68 (m, 1H), 4.54-4.57 (m, 1H), 4.40-4.42 (m, 1H), 3.96-4.00 (m, 1H), 3.85-3.89 (m, 1H), 3.73-3.77 (m, 1H), 3.51-3.68 (m, 3H), 3.08-3.12 (m, 1H), 2.97-3.02 (m, 1H), 2.18-2.34 (m, 4H), 1.92-2.12 (m, 5H), 1.57-1.61 (m, 2H), 1.32-1.35 (m, 10H), 0.92 (t, J=7.00 Hz, 3H). LC-MS (ESI): calcd for C$_{29}$H$_{42}$N$_4$O$_7$ 558.3, found m/z 558.5 (M+H$^+$).

Example 1.10

Stearoyl-L-prolyl-L-prolylglycyl-L-tyrosine (stearoyl-PPGY-OH)(SEQ ID NO: 10)

$^1$H NMR (500 MHz, CD$_3$OD) δ 7.03 (d, J=8.55 Hz, 2H), 6.71 (d, J=8.25 Hz, 2H), 4.66-4.68 (m, 1H), 4.55-4.57 (m, 1H), 4.40-4.44 (m, 1H), 3.96-4.02 (m, 1H), 3.84-3.89 (m, 1H), 3.71-3.76 (m, 1H), 3.48-3.68 (m, 4H), 3.08-3.12 (m, 1H), 2.97-3.02 (m, 1H), 2.14-2.42 (m, 5H), 1.90-2.14 (m, 6H), 1.57-1.61 (m, 2H), 1.32-1.35 (m, 30H), 0.92 (t, J=7.15 Hz, 3H). LC-MS (ESI): calcd for C$_{39}$H$_{62}$N$_4$O$_7$ 698.5, found m/z 698.5 (M+H$^+$).

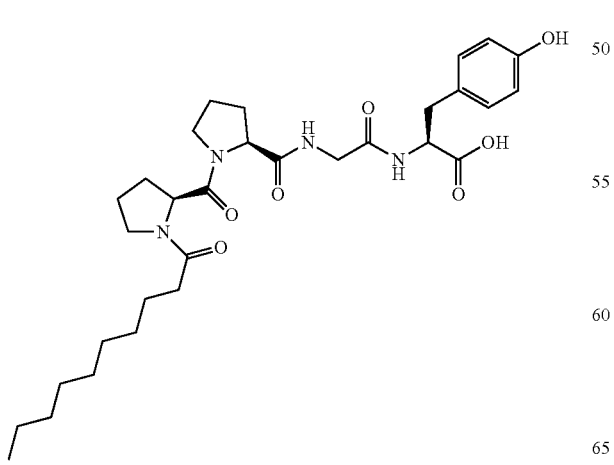

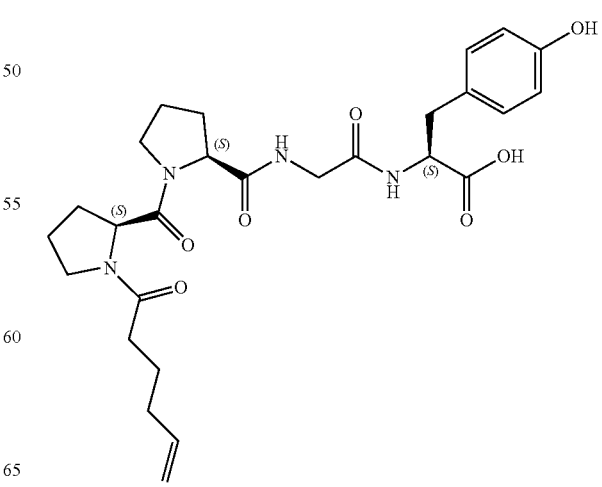

Example 1.11

Hex-5-enoyl-L-prolyl-L-prolylglycyl-L-tyrosine (5-hexenoyl-PPGY-OH)(SEQ ID NO: 11)

¹H NMR (500 MHz, CD₃OD) δ 7.05 (d, J=8.55 Hz, 2H), 6.70 (d, J=8.25 Hz, 2H), 5.78-5.89 (m, 1H), 4.98-5.08 (m, 3H), 4.66-4.69 (m, 1H), 4.54-4.57 (m, 1H), 4.40-4.44 (m, 1H), 3.97-4.01 (m, 1H), 3.84-3.90 (m, 1H), 3.73-3.76 (m, 1H), 3.47-3.68 (m, 4H), 3.08-3.12 (m, 1H), 2.97-3.01 (m, 1H), 2.33-2.42 (m, 2H), 2.20-2.30 (m, 2H), 2.06-2.15 (m, 4H), 1.92-2.04 (m, 4H), 1.67-1.76 (m, 3H). LC-MS (ESI): calcd for $C_{27}H_{36}N_4O_7$ 528.3, found m/z 529 (M+H⁺).

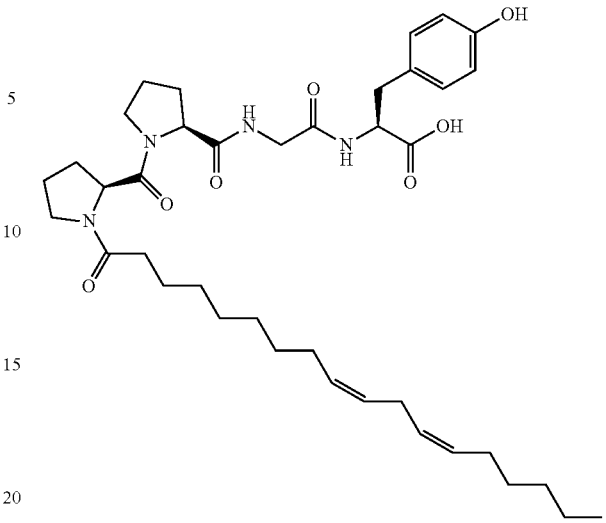

Example 1.12

Oleoyl-L-prolyl-L-prolylglycyl-L-tyrosine (oleyl-PPGY-OH)(SEQ ID NO: 12)

¹H NMR (500 MHz, CD₃OD) δ 7.03 (d, J=8.50 Hz, 2H), 6.71 (d, J=8.50 Hz, 2H), 5.34-5.38 (m, 2H), 4.66-4.68 (m, 1H), 4.55-4.57 (m, 1H), 4.40-4.42 (m, 1H), 3.96-4.01 (m, 1H), 3.84-3.90 (m, 1H), 3.73-3.77 (m, 1H), 3.53-3.69 (m, 4H), 3.08-3.12 (m, 1H), 2.97-3.01 (m, 1H), 2.18-2.39 (m, 5H), 2.06-2.12 (m, 2H), 1.92-2.05 (m, 3H), 1.58-1.61 (m, 3H), 1.31-1.35 (m, 25H), 0.92 (t, J=7.0 Hz, 3H). LC-MS (ESI): calcd for $C_{39}H_{60}N_4O_7$ 696.4, found m/z 697.3 (M+H⁺).

Example 1.13

((9Z,12Z)-octadeca-9,12-dienoyl)-L-prolyl-L-prolylglycyl-L-tyrosine (linoleyl-PPGY-OH)(SEQ ID NO: 13)

¹H NMR (500 MHz, CD₃OD) δ 7.05 (d, J=8.45 Hz, 2H), 6.71 (d, J=8.45 Hz, 2H), 5.32-5.41 (m, 4H), 4.66-4.68 (m, 1H), 4.55-4.57 (m, 1H), 4.40-4.43 (m, 1H), 3.96-4.01 (m, 1H), 3.84-3.89 (m, 1H), 3.73-3.77 (m, 1H), 3.53-3.68 (m, 4H), 3.08-3.12 (m, 1H), 2.97-3.01 (m, 1H), 2.80 (t, J=6.40 Hz, 2H), 2.19-2.39 (m, 5H), 1.93-2.13 (m, 10H), 1.59-1.61 (m, 3H), 1.31-1.40 (m, 15H), 0.92 (t, J=6.59 Hz, 3H). LC-MS (ESI): calcd for $C_{39}H_{58}N_4O_7$ 694.4, found m/z 695.2 (M+H⁺).

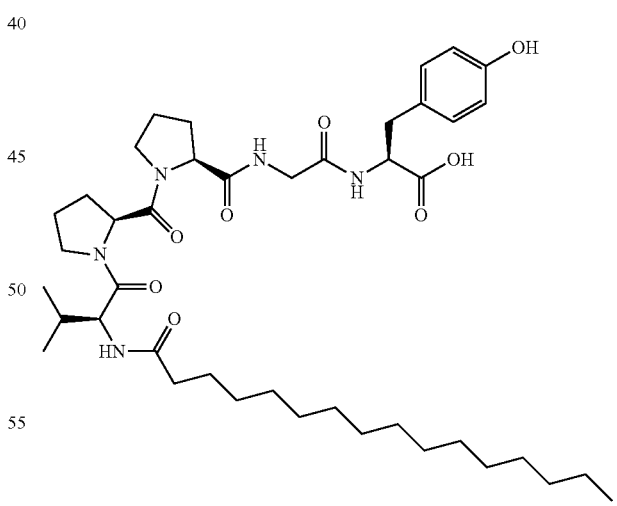

Example 1.14: Palmitoyl-L-valyl-L-prolyl-L-prolylglycyl-L-tyrosine (Pal-VPPGY-OH)(SEQ ID NO: 14)

¹H NMR (500 MHz, CD₃OD) δ 7.04 (d, J=8.35 Hz, 2H), 6.71 (d, J=8.35 Hz, 2H), 4.67-4.70 (m, 1H), 4.52-4.58 (m, 1H), 4.39-4.43 (m, 1H), 3.77-4.05 (m, 4H), 3.64-3.73 (m,

2H), 3.49-3.60 (m, 1H), 3.01-3.11 (m, 2H), 1.87-2.31 (m, 15H), 1.61-1.63 (m, 3H), 1.31 (m, 24H), 1.01 (d, J=6.58 Hz, 3H), 0.98 (d, J=6.58 Hz, 3H), 0.92 (t, J=6.96 Hz, 3H). LC-MS (ESI), calcd for $C_{42}H_{67}N_5O_8$ 769.5, found m/z 770.7 (M+H$^+$).

Example 1.15: Decanoyl-L-valyl-L-prolyl-L-prolylglycyl-L-tyrosine (decanoyl-VPPGY-OH)(SEQ ID NO: 15)

$^1$H NMR (500 MHz, CD$_3$OD) δ 7.05 (d, J=8.45 Hz, 2H), 6.71 (d, J=8.45 Hz, 2H), 4.67-4.70 (m, 1H), 4.50-4.57 (m, 1H), 4.39-4.43 (m, 1H), 3.95-4.05 (m, 2H), 3.80-3.91 (m, 1H), 3.65-3.70 (m, 2H), 3.64-3.73 (m, 2H), 3.53-3.57 (m, 1H), 3.01-3.10 (m, 2H), 1.89-2.31 (m, 12H), 1.61-1.63 (m, 3H), 1.31 (m, 24H), 1.01 (d, J=6.68 Hz, 3H), 0.97 (d, J=6.55 Hz, 3H), 0.92 (t, J=7.05 Hz, 3H). LC-MS (ESI), calcd for $C_{36}H_{55}N_5O_8$ 685.4, found m/z 686.6 (M+H$^+$).

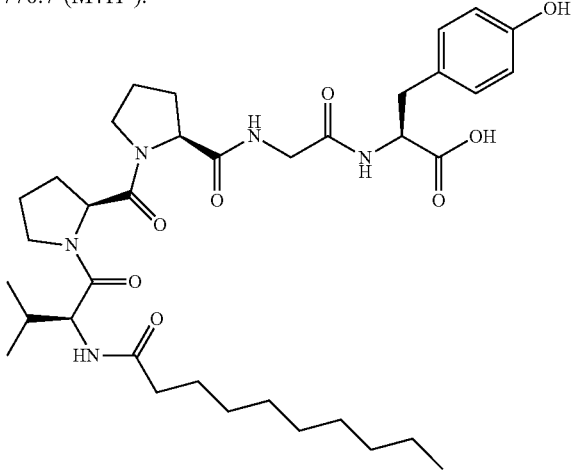 [SMILES: CCCCCCCCCC(=O)N[C@H](C(=O)N1CCC[C@H]1C(=O)N1CCC[C@H]1C(=O)NCC(=O)N[C@@H](Cc1ccc(O)cc1)C(=O)O)C(C)C]

Table 1 depicts the compounds according to Examples 1.1 through 1.15.

TABLE 1

Compounds according to Examples 1.1 through 1.15

| Example No. (Compound No.) | Chemical Formula |
|---|---|
| 1.1 SEQ ID NO: 2 | Pal-PPGY-OH |
| 1.2 | Pal-PGY-OH |

TABLE 1-continued
Compounds according to Examples 1.1 through 1.15
| Example No. (Compound No.) | Chemical Formula |
|---|---|
| 1.3 SEQ ID NO: 3 | 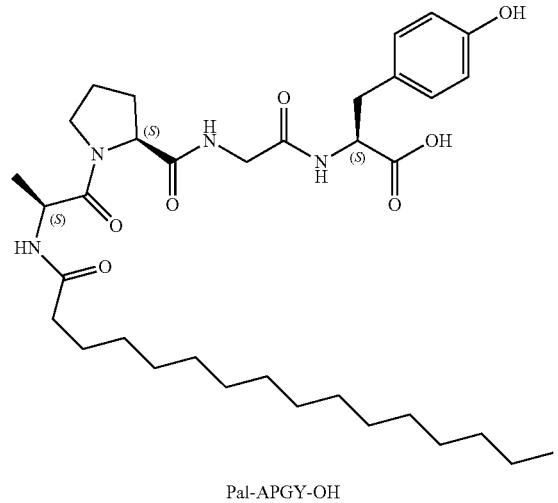<br>Pal-APGY-OH |
| 1.4 SEQ ID NO: 4 | 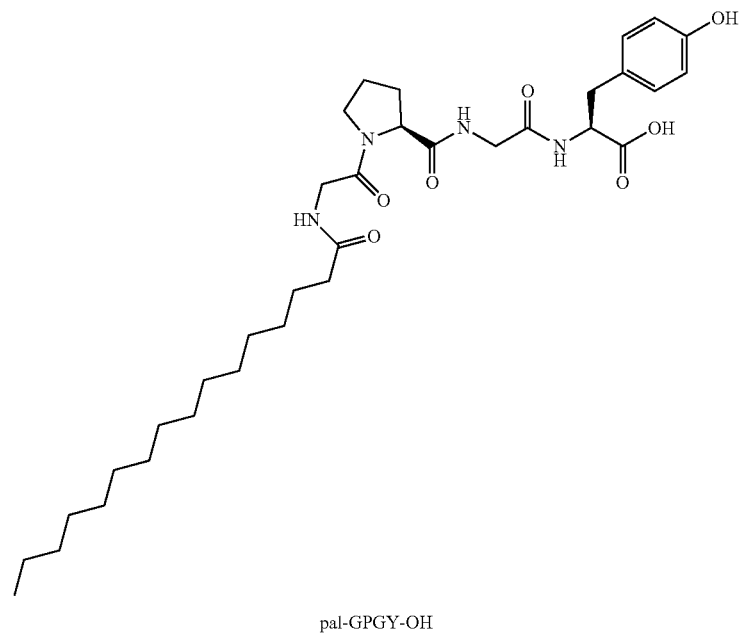 [SMILES: CCCCCCCCCCCCCCCC(=O)NCC(=O)N1CCC[C@H]1C(=O)NCC(=O)N[C@@H](Cc1ccc(O)cc1)C(=O)O]<br>pal-GPGY-OH |

TABLE 1-continued
Compounds according to Examples 1.1 through 1.15
| Example No. (Compound No.) | Chemical Formula |
|---|---|
| 1.5 SEQ ID NO: 5 | 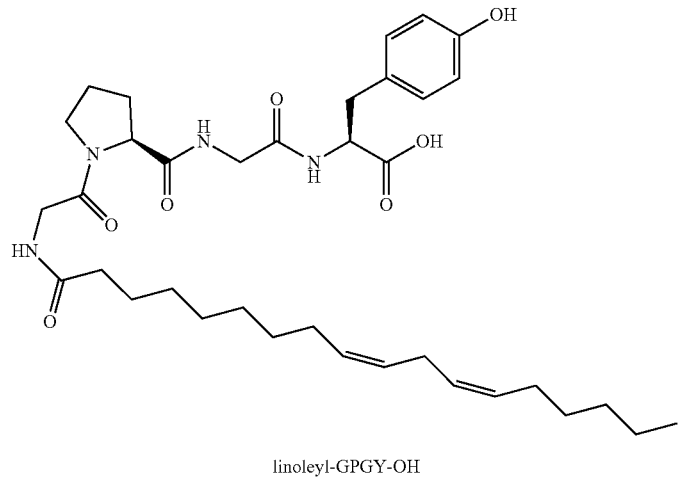 [SMILES: CCCCC/C=C\C/C=C\CCCCCCCC(=O)NCC(=O)N1CCC[C@H]1C(=O)NCC(=O)N[C@@H](Cc1ccc(O)cc1)C(=O)O]<br>linoleyl-GPGY-OH |
| 1.6 SEQ ID NO: 6 | 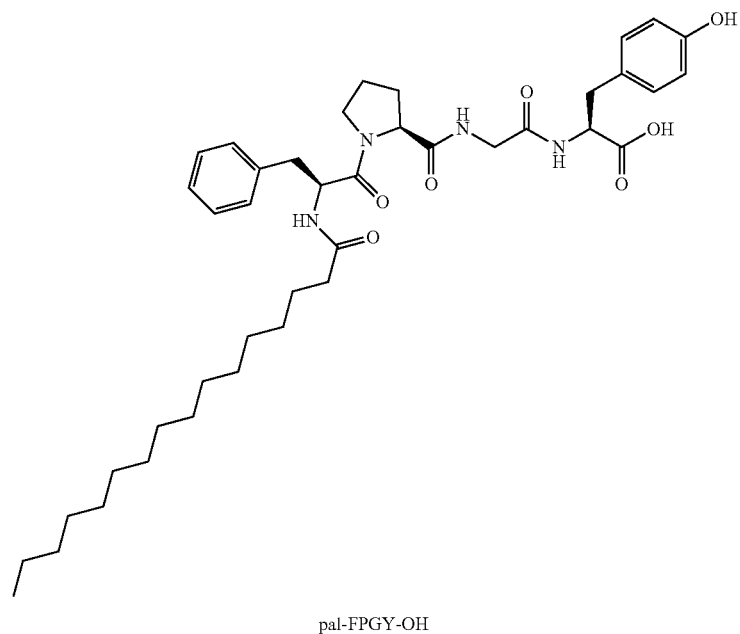 [SMILES: CCCCCCCCCCCCCCCC(=O)N[C@@H](Cc1ccccc1)C(=O)N1CCC[C@H]1C(=O)NCC(=O)N[C@@H](Cc1ccc(O)cc1)C(=O)O]<br>pal-FPGY-OH |
| 1.7 SEQ ID NO: 7 | 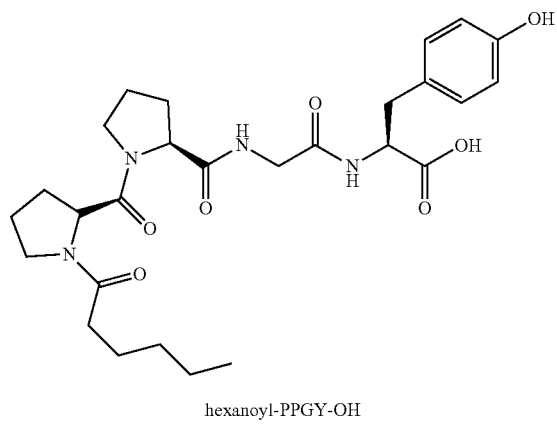<br>hexanoyl-PPGY-OH |

TABLE 1-continued
Compounds according to Examples 1.1 through 1.15
| Example No. (Compound No.) | Chemical Formula |
|---|---|
| 1.8 SEQ ID NO: 8 | 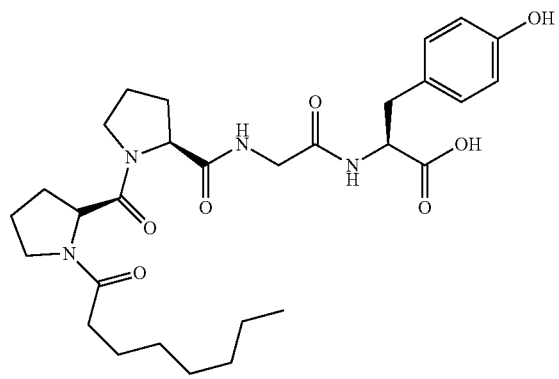 octanoyl-PPGY-OH |
| 1.9 SEQ ID NO: 9 | 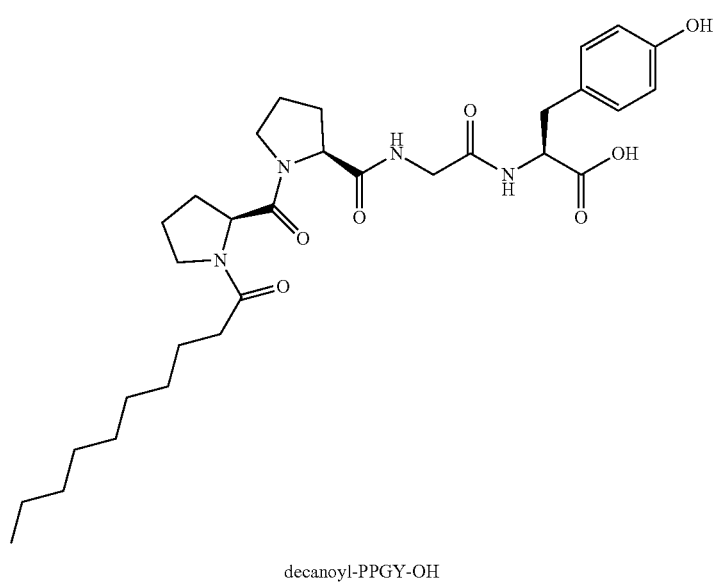 [SMILES: CCCCCCCCCC(=O)N1CCC[C@H]1C(=O)N1CCC[C@H]1C(=O)NCC(=O)N[C@@H](Cc1ccc(O)cc1)C(=O)O] decanoyl-PPGY-OH |
| 1.10 SEQ ID NO: 10 | 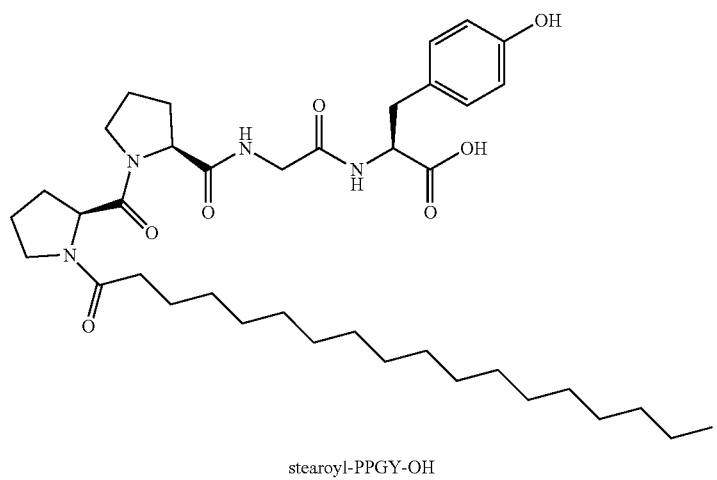 [SMILES: CCCCCCCCCCCCCCCCCC(=O)N1CCC[C@H]1C(=O)N1CCC[C@H]1C(=O)NCC(=O)N[C@@H](Cc1ccc(O)cc1)C(=O)O] stearoyl-PPGY-OH |

TABLE 1-continued
Compounds according to Examples 1.1 through 1.15
| Example No. (Compound No.) | Chemical Formula |
|---|---|
| 1.11 SEQ ID NO: 11 | 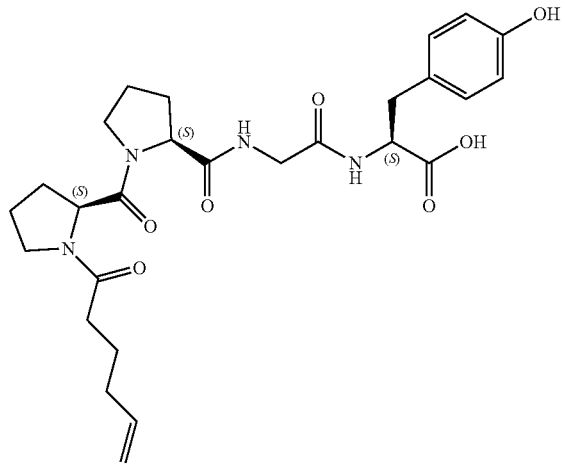<br>5-hexenoyl-PPGY-OH |
| 1.12 SEQ ID NO: 12 | 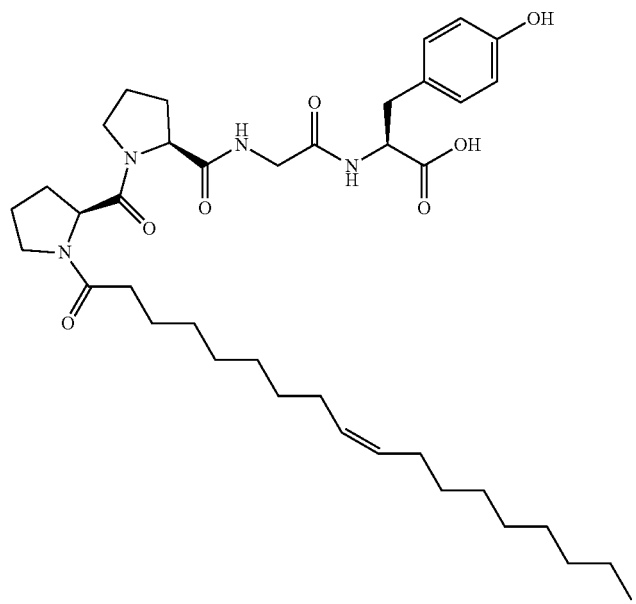<br>oleyl-PPGY-OH |

TABLE 1-continued
Compounds according to Examples 1.1 through 1.15
| Example No. (Compound No.) | Chemical Formula |
|---|---|
| 1.13 SEQ ID NO: 13 | 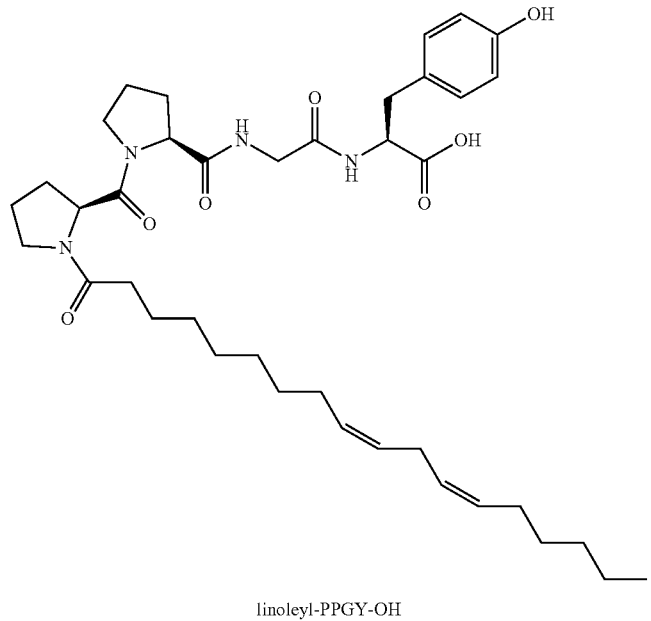 [SMILES: CCCCC/C=C\C/C=C\CCCCCCCC(=O)N1CCC[C@H]1C(=O)N1CCC[C@H]1C(=O)NCC(=O)N[C@@H](Cc1ccc(O)cc1)C(=O)O]<br>linoleyl-PPGY-OH |
| 1.14 SEQ ID NO: 14 | 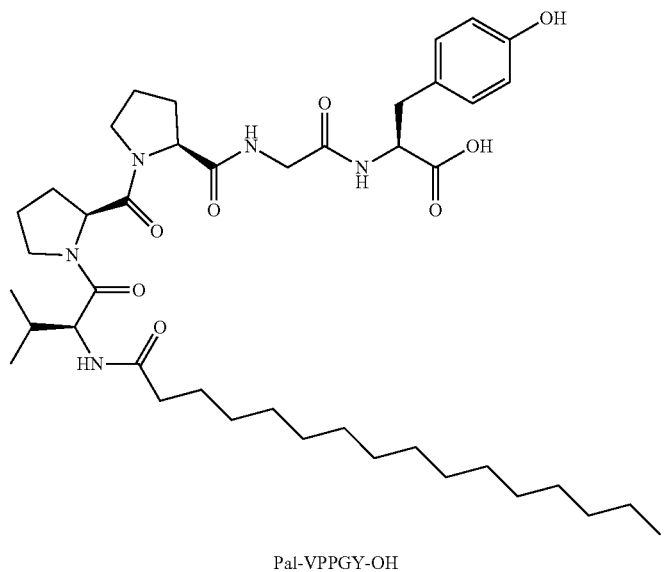 [SMILES: CCCCCCCCCCCCCCCC(=O)N[C@H](C(=O)N1CCC[C@H]1C(=O)N1CCC[C@H]1C(=O)NCC(=O)N[C@@H](Cc1ccc(O)cc1)C(=O)O)C(C)C]<br>Pal-VPPGY-OH |

TABLE 1-continued

Compounds according to Examples 1.1 through 1.15

Example No.
(Compound No.) — Chemical Formula 1.15
SEQ ID NO: 15 decanoyl-VPPGY-OH

Example 2

Assays

Example 2.1

Suppression of Expression of IL-6

To evaluate suppression of expression of IL-6 by the compounds of the present invention, the following experiment was performed.

First, RAW 264.7 macrophage cells were purchased from American Type Culture Collection (ATCC; Manassas, Va.), and were culture at a temperature of 37° C., under 5% $CO_2$ atmosphere, using 10% Fetal Bovine Serum (FBS) and Dulbecco's Modified Eagle's Medium (DMEM) containing 1% penicillin/streptomycin.

The cultured RAW 264.7 macrophage cells were divided into a 6-well cell culture plate. After 24 hours, the cells were pretreated with compound 1.1 (SEQ ID NO: 2), compound 1.2, and smaducin-6, respectively, in a concentration of 100 nM for 30 min, and further treated with lipopolysaccharides (LPS) for two hours. These cells were collected using TRIzol® and the RNA was extracted. From 2 μg of the extracted RNA, cDNAs (complementary deoxyribonucleic acids) were synthesized and reverse transcription polymerase chain reactions (RT-PCR) and real-time polymerase chain reactions (Real-Time PCR) were performed. Samples from the RT-PCR were confirmed by electrophoresis on agarose gels and quantified using densitometer. A glyceraldehyde 3-phosphate dehydrogenase (GAPDH) gene was used as a loading control for the interleukin-6 gene.

Figure 1B:
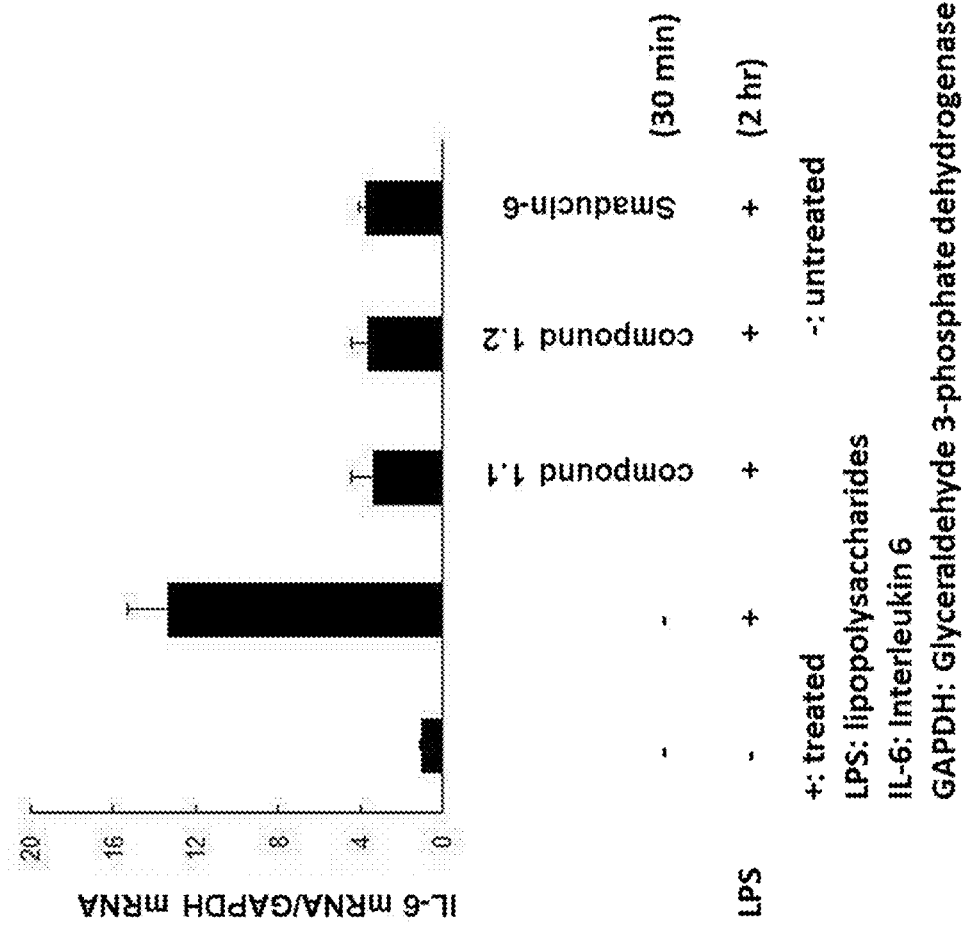
FIG. 1B is a graph showing that compounds according to embodiments of the present invention suppress the expression of IL-6. (Compound 1.1 (SEQ ID NO: 2)).

FIG. 1A shows images depicting suppression of expression of interleukin-6 by compound 1.1 (SEQ ID NO: 2) and compound 1.2, and FIG. 1B is a graph showing the quantified suppression of expression of interleukin-6 by the compound 1.1 (SEQ ID NO: 2) and compound 1.2. As compared to the untreated sample, when the cells treated with the compound according to the present invention, the expression of interleukin-6, which was induced by LPS treatment, was suppressed.

In addition, RAW 264.7 macrophage cells cultured as described above were also divided into a 6-well plate, after 24 hours, were pretreated with 100 nM of compound 1.1 (SEQ ID NO: 2) for 30 minutes, and further treated with LPS for two hours. The above cell culture was collected and, using a cytokine array (Mouse cytokine array C3, RayBiotech), changes in amounts of cytokine and chemokine were quantified by a densitometer. The cytokines and chemokines detected by the compound of the present invention included G-CSF, IL-2, SCF, VEGF, CX3CL1, IGFBP5, IGFBP6, IL-1α, IL-1β, IL-6, IL-9, MCP-1, MIP-3α, IL12p40/70, MIG, TNF-α, and VCAM-1. As compared to the untreated samples, when the cells were treated with the compounds of the present invention, the expression of the above cytokines and chemokines, which were induced by LPS treatment, were suppressed as statistically meaningful (FIGS. 2A-2D).

Figure 3:
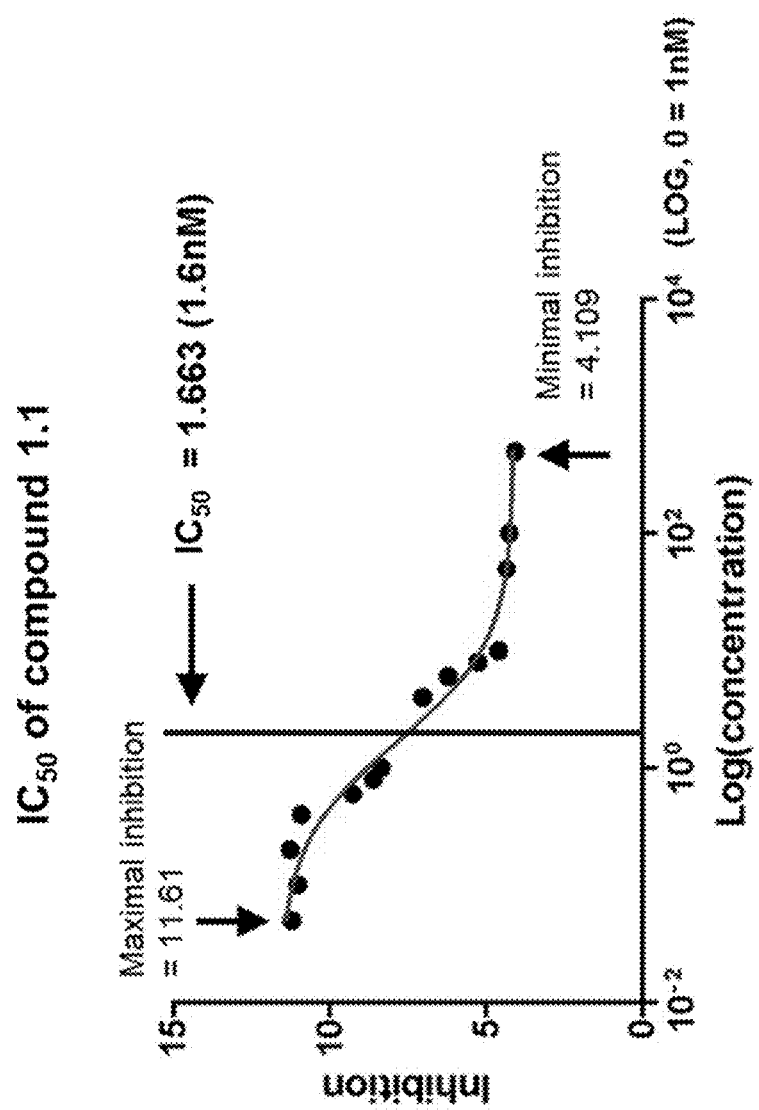
FIG. 3 shows that compounds according to embodiments of the present invention suppress the expression of IL-6 in a host in a cell line RAW 264.7. (Compound 1.1 (SEQ ID NO: 2)).

RAW 264.7 macrophage cells were treated with varying concentrations of compound 1.1 (SEQ ID NO: 2) from 50 pM to 500 nM for 30 minutes, and treated with 100 ng/mL of LPS for two hours. The induced expression of interleukin-6 was quantified as described above and the results were presented in FIG. 3. In the RAW 264.7 macrophage cells, the concentration of compound 1.1 (SEQ ID NO: 2) where the expression of interleukin-6 was suppressed to 50% or below (i.e. $IC_{50}$) was about 1.6 nM.

Example 2.2

Suppression of Activity of NF-κ13

To evaluate whether NF-κB signal induced by LPS was specifically suppressed by the compounds of the present invention, the following experiments were performed.

Specifically, 5×NF-κB-Luc reporter plasmid was transfected into RAW 264.7 cells using Effectene (Qiagen, USA).

Figure 4:
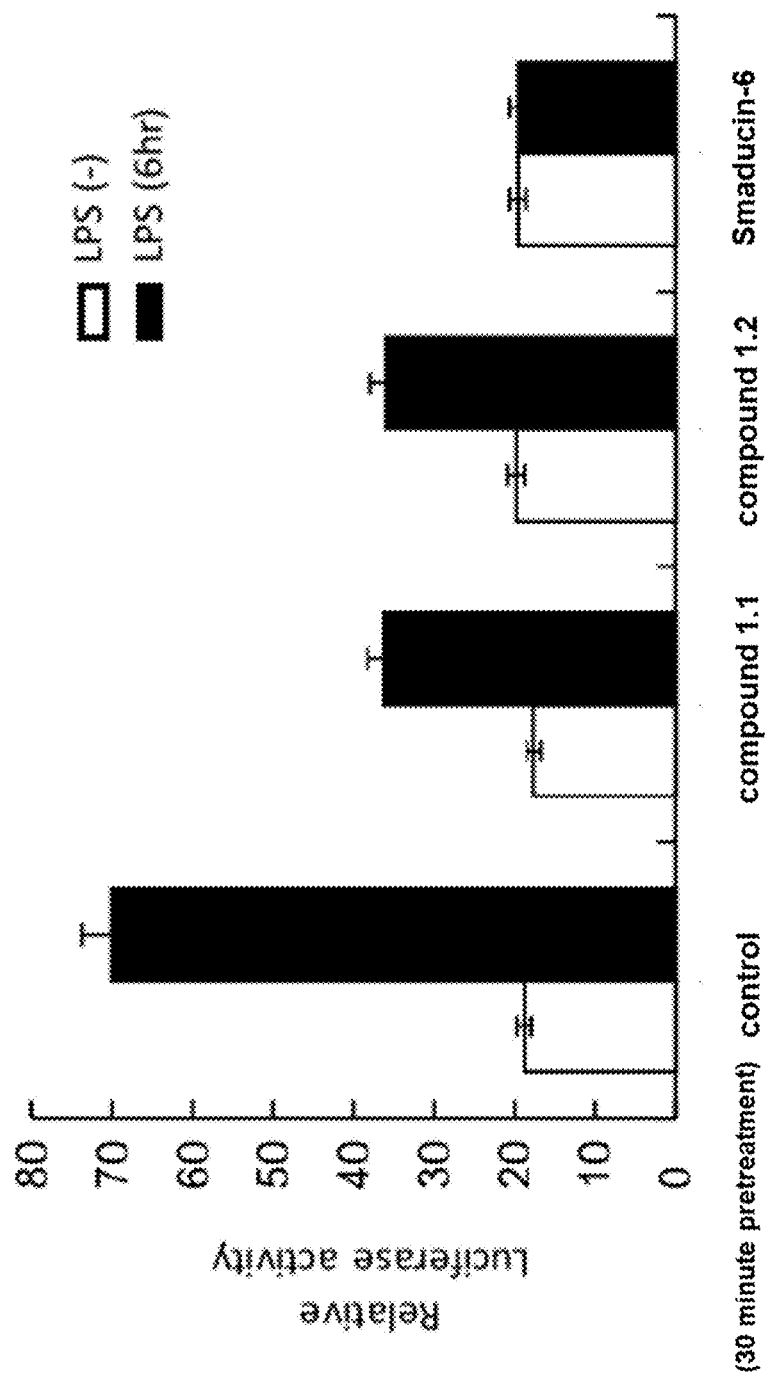
FIG. 4 shows that compounds according to embodiments of the present invention inhibit the activity of NF-κB. (Compound 1.1 (SEQ ID NO: 2)).

The transfected cells were pretreated with 100 nM of compound 1.1 (SEQ ID NO: 2) for 30 minutes, and further treated with LPS (100 ng/ml) for two hours, and luciferase activity in the cells was measured (FIG. 4 depicts a graph showing relative inhibition activities of compound 1.1 (SEQ ID NO: 2) and compound 1.2 to NF-κB activation). When the cells were treated with compound 1.1 (SEQ ID NO: 2) and compound 1.2 according to the present invention, activation of NF-κB, which was induced by LPS, was inhibited (FIG. 4).

In addition, 5×NF-κB-Luc reporter plasmid was transfected into RAW 264.7 macrophage cells and treated with compounds of the present invention, as described above. After 24 hours of the transfection, the cells were pretreated with DMSO (control), compound 1.1 (SEQ ID NO: 2), reference compound 1 (SEQ ID NO: 16) (compound where palmitic acid is removed from compound 1.1 (SEQ ID NO: 2)), and smaducin-6 were treated at various concentrations of 100 pM, 1 nM, and 100 nM for 30 minutes, and then the cells were treated with 100 ng/ml of LPS for two hours. Luciferase activity in the cells was measured and the results are presented in FIG. 5.

Figure 5:
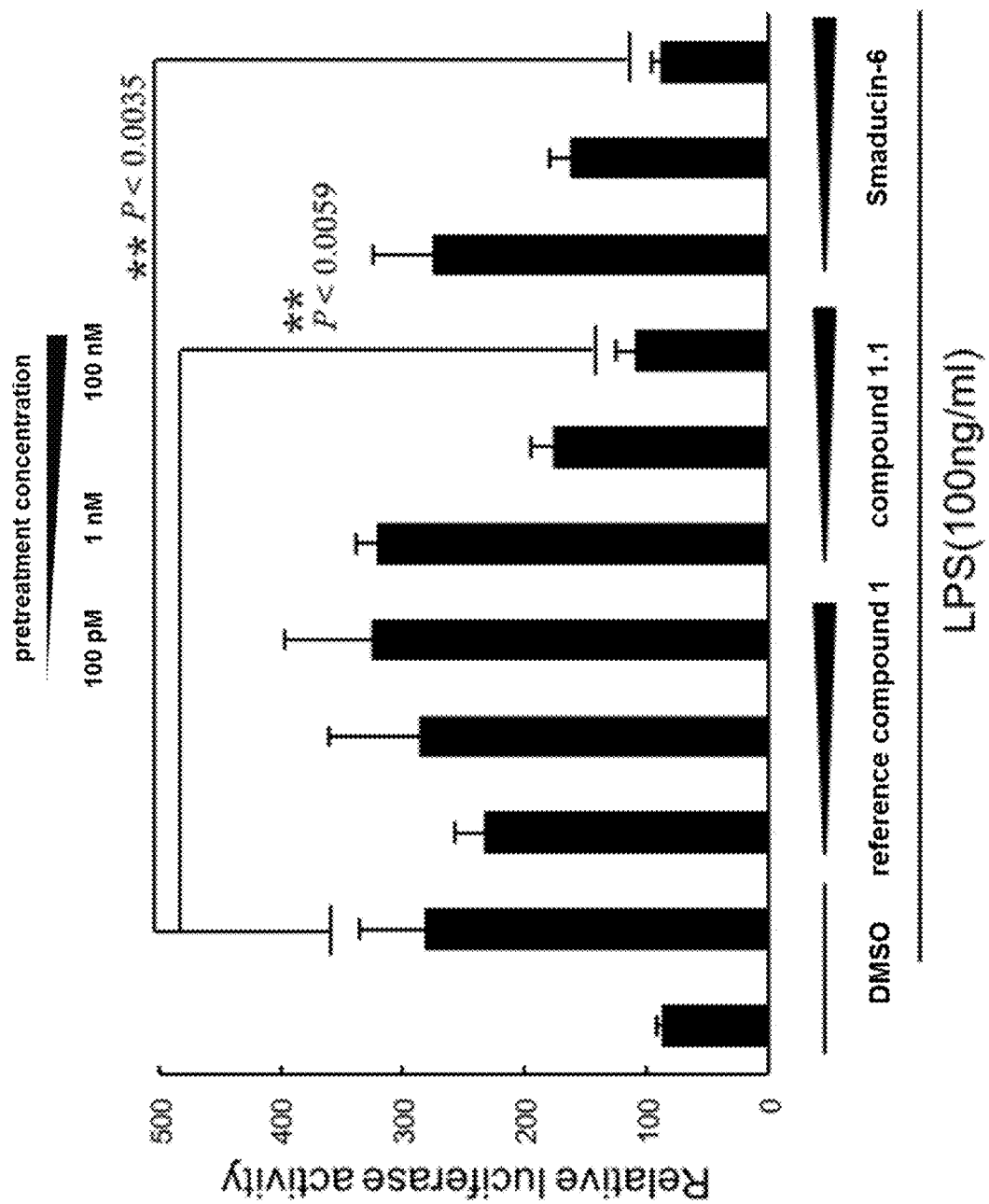
FIG. 5 shows that the compounds according to embodiments of the present invention suppress NF-κB. (Compound 1.1 (SEQ ID NO: 2), Reference compound 1 (SEQ ID NO: 16)).

As shown in FIG. 5, when the cells were pretreated with compound 1.1 (SEQ ID NO: 2) (similar to the cells pretreated with smaducin-6), inhibition of the activity of NF-κB, which was induced by LPS treatment, was increased as dose of compound 1.1 (SEQ ID NO: 2) increased. In contrast, when the cells were pre-treated with DMSO or reference compound 1 (SEQ ID NO: 16), the activity of the NF-κB was not inhibited in dose dependent manner.

Example 2.3

Signaling Pathway Selectivity

To evaluate signaling pathway selectivity of compound 1.1 (SEQ ID NO: 2) according to the present invention, the following experiments were performed. The following experiments were performed to test whether compound 1.1 (SEQ ID NO: 2) specifically suppressed a signaling pathway induced by an individual inducer.

Specifically, 5×NF-κB-Luc reporter plasmid, SBE-Luc reporter plasmid, and BRE-Luc reporter plasmid were individually transfected into Raw 264.7 macrophage cells. After 24 hours, the cells transfected with the NF-κB-Luc reporter plasmid were treated with 100 ng/mL of LPS, the cells transfected with the SBE-Luc reporter plasmid were treated with 5 ng/mL of TFG-β1, and the cells transfected with the BRE-Luc reporter plasmid were treated with 100 ng/mL of BMP6 for two hours.

Figures 6A, 6B, 6C:
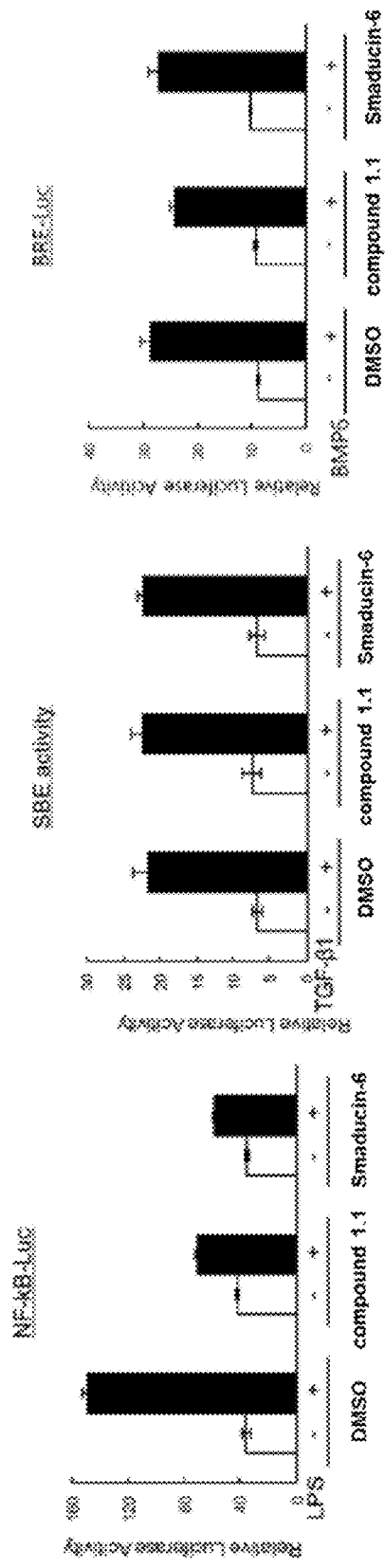
FIGS. 6A-6C are bar graphs that show that the compounds according to embodiments of the present invention inhibit the activity of NF-κB (FIG. 6A) while not affecting signal transmission of TGF-β (FIG. 6B) and BMP (FIG. 6C). (Compound 1.1 (SEQ ID NO: 2)).

FIGS. 6A-6C is a graph showing the relative suppression activities of compound 1.1 (SEQ ID NO: 2) to different signaling pathways. As shown in FIGS. 6A-6C, when the cells were treated with compound 1.1 (SEQ ID NO: 2) according to the present invention, activation of NF-κB, which was induced by LPS treatment, was inhibited. However, activation of BRE, which was induced by the BMP6 treatment, or activation of SBE, which was induced by the TFG-β1 treatment, was not inhibited by compound 1.1 (SEQ ID NO: 2). Accordingly, compound 1.1 (SEQ ID NO: 2) selectively inhibited activation of NF-κB signaling pathway.

Particularly, recent studies have reported that, for treating an inflammatory bowel disease, TFG-β and BMP signaling pathways may specifically relate to mucosal wound healing and the like (*Nature* 449 (2007), 361-365, *Am J Path,* 162(2), (2003), *Nature Immunol.* 6, (2005), 507-514, *J Cell Physiol.* 196(2): (2003); 258-64), and *Nature Protocols,* 8(3), (2013) 627-637, which are incorporated herein by reference), and TFG-β could be a very important factor in control of the inflammatory condition (dendritic cell conditioning) in intestines (*J. Clin. Invest.,* 111 (2003), 1297-1308, *Immunity,* 10 (1999), 39-49, *Eur. J. Immunol,* 36 (2006), 864-874, *Immunity,* 25 (2006), 319-329, *Cell* 118 (2004), 229-241, and *J. Immunol.* 179 (2007), 2690-2694, which are incorporated herein by reference). Accordingly, the compounds of the present invention do not suppress activation of TFG-β and BMP signaling pathways which indicated that those compounds are markedly effective for the treatment of inflammatory bowel disease.

Example 2.4

Disruption of Formation of Signaling Complex and Degradation of Inhibitor κB (IκB)

In order to test whether the compound of the present invention can disrupt formation of inflammation signaling pathway protein complex mediated by MyD88 and/or RIP1, e.g. Toll-like receptors (TLRs) signaling pathway protein complex, immunoprecipitation experiments were performed. At a same time, the following experiments were performed to measure IκB degradation by the compound of the present invention as measuring changes of concentration of IκB.

Specifically, using antibodies corresponding to proteins which relate to the formation of Toll-like receptors (TLRs) signaling pathway protein complex (for example, IRAK1, TRAF6, MyD88, RIP1 and Pellino-1), disruption of the formation of inflammatory signaling pathway protein complexes was affirmed by immunoprecipitation. As reference control, a relative amount of expression of β-actin from the total cell lysate was compared and presented using Western blot.

RAW264.7 macrophage cells were individually retreated with compound 1.1 (SEQ ID NO: 2) and compound 1.2, and smaducin-6, and further treated with LPS. These RAW264.7 macrophage cells were collected, lysed in a lysis butter (PBS containing 0.5% Triton X-100, 20 mM HEPES (pH 7.4), 150 mM NaCl, 12.5 mM β-glycerol phosphate, 1.5 mM $MgCl_2$, 10 mM NaF, 2 mM DTT, 1 mM Na3O4V, 2 mM EGTA, and 1 mM Protease Inhibitor (PMSF)), and centrifuged at 13000 rpm for 10 minutes. For immunoprecipitation assays, the supernatant was incubated at 4° C. for 12 hours, with protein-A agarose beads and the antibodies corresponding to the above proteins, and the beads were subsequently washed three times with the lysis buffer. The immunoprecipitated substances were dissociated from the beads with addition of 2× sample buffer, and were boiled. The prepared samples were loaded on SDS-polyacrylamide gel (FIG. 7).

To measure changes in concentration of IκB, RAW264.7 macrophage cells were individually pre-treated with compound 1.1 (SEQ ID NO: 2), compound 1.2, and smaducin-6 at a concentration of 100 nM, and then treated with LPS. The extracted cell lysate was used for immunoblotting with IκBα antibody, and β-actin was used as reference (FIG. 7).

Figure 7:
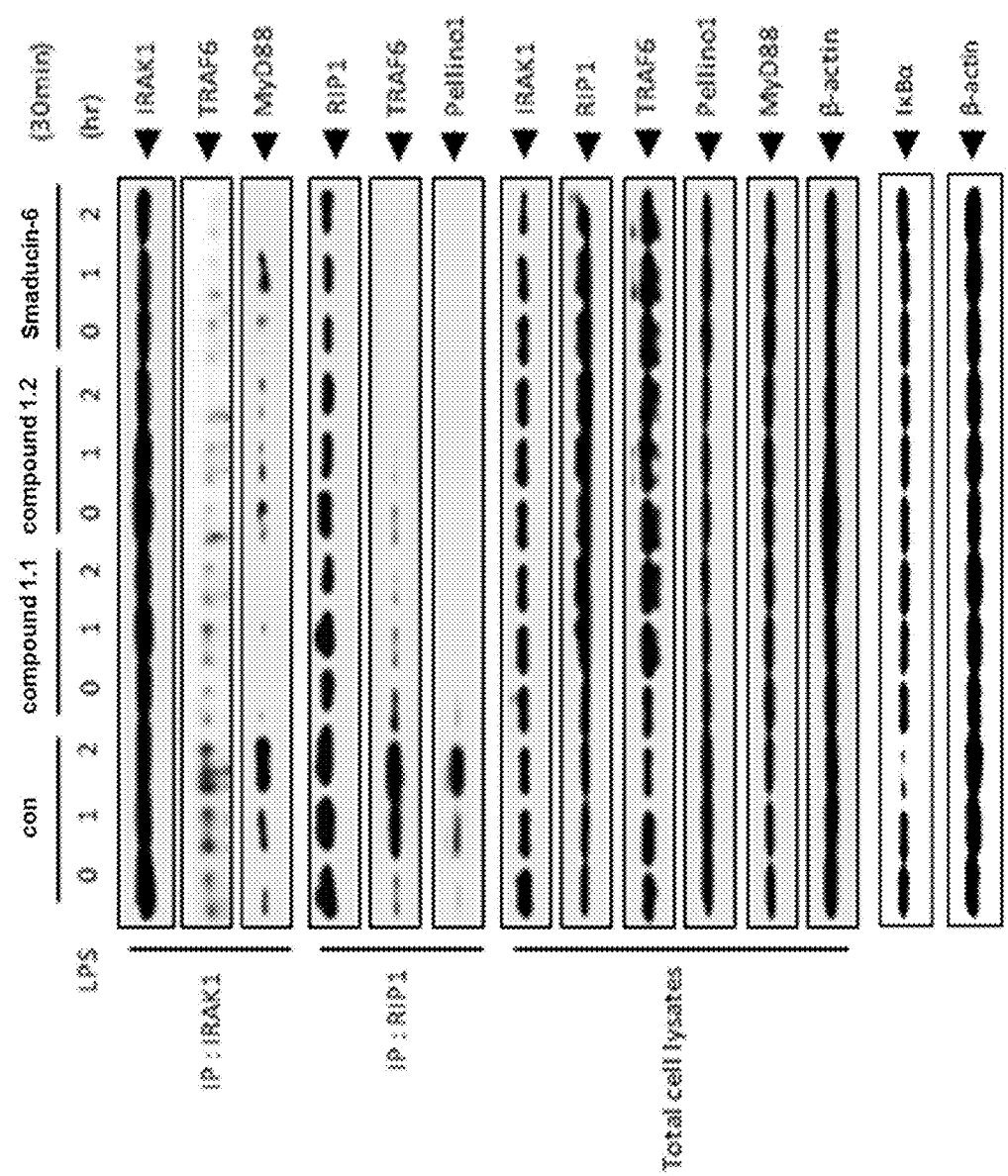
FIG. 7 is an immunoprecipitation result showing that the compounds according to embodiments of the present invention inhibit formation of inflammation signaling pathway protein complex mediated by IRAK-1, MyD88, and/or RIP1 and showing that the compounds according to embodiments of the present invention change the concentration of IκB. (Compound 1.1 (SEQ ID NO: 2)).

FIG. 7 shows immunoprecipitation images indicating that compound 1.1 (SEQ ID NO: 2) and compound 1.2 disrupted the inflammatory signaling pathway protein complexes, which are mediated by MyD88 or RIP1 and additionally indicating changes in the concentration of IκB by these compounds. When the cells were treated with the compounds according to the present invention, as compared to the control of total cell lysate, the formation of inflammatory signaling pathway protein complex (which is mediated by MyD88 or RIP1) was disrupted (FIG. 7). Cells treated with the compound of the present invention were stabilized by dephosphorylating IκB as compared to expression of the reference of β-actin.

When the cells were treated with the compounds according to the present invention, as compared to the control of total cell lysate, formation of the MyD88 protein complex and the RIP1 protein complex, and activities thereof were substantially disrupted and inhibited (FIG. 7). These results indicated that the compounds in the present invention may be used for the treatment of diseases related to Pellino-1. Furthermore, in addition to above described inflammatory bowel diseases, the compounds of the present invention may be effective for preventing or treating geographic atrophy, wet-age-related macular disease (wet-AMD), dry-age-related macular disease (dry-AMD), diabetic retinopathy, multiple sclerosis (MS), lung inflammation, bacterial pneumonia, viral pneumonia, Diffuse large B-cell lymphoma (DLBCL, GCB type or ABC type), and alopecia (*Journal of Clinical Investigation*, 124(11), (2014), 4976-4988, *J Virology*, 86(12), (2012), 6595-6604, *Nature Medicine*, 19(5), (2013), 595-602, *J. Immunol.*, 187 (2011), 1-14, *J. Inv. Derm.*, 132 (2012), 43-49, *Med. Inflamm.*, (2010), Article ID 928030, *Hair The Transplant*, 4 (2014), 4:1, *Exp. Derm.*, 17 (2007), 12-19, and *DDT Dis. Mech.* 5 (2009), e163-171), which are incorporated herein by reference).

Bone-marrow-derived macrophage (BMDM) cells were individually pretreated with compound 1.1 (SEQ ID NO: 2), reference compound 1 (SEQ ID NO: 16), and smaducin-6 at various concentrations of 100 pM, 1 nM, and 100 nM, and then further treated with 100 ng/mL of LPS. The extracted cell lysates were used for immunoblot as described above, and the results were shown in FIG. 8.

Figure 8:
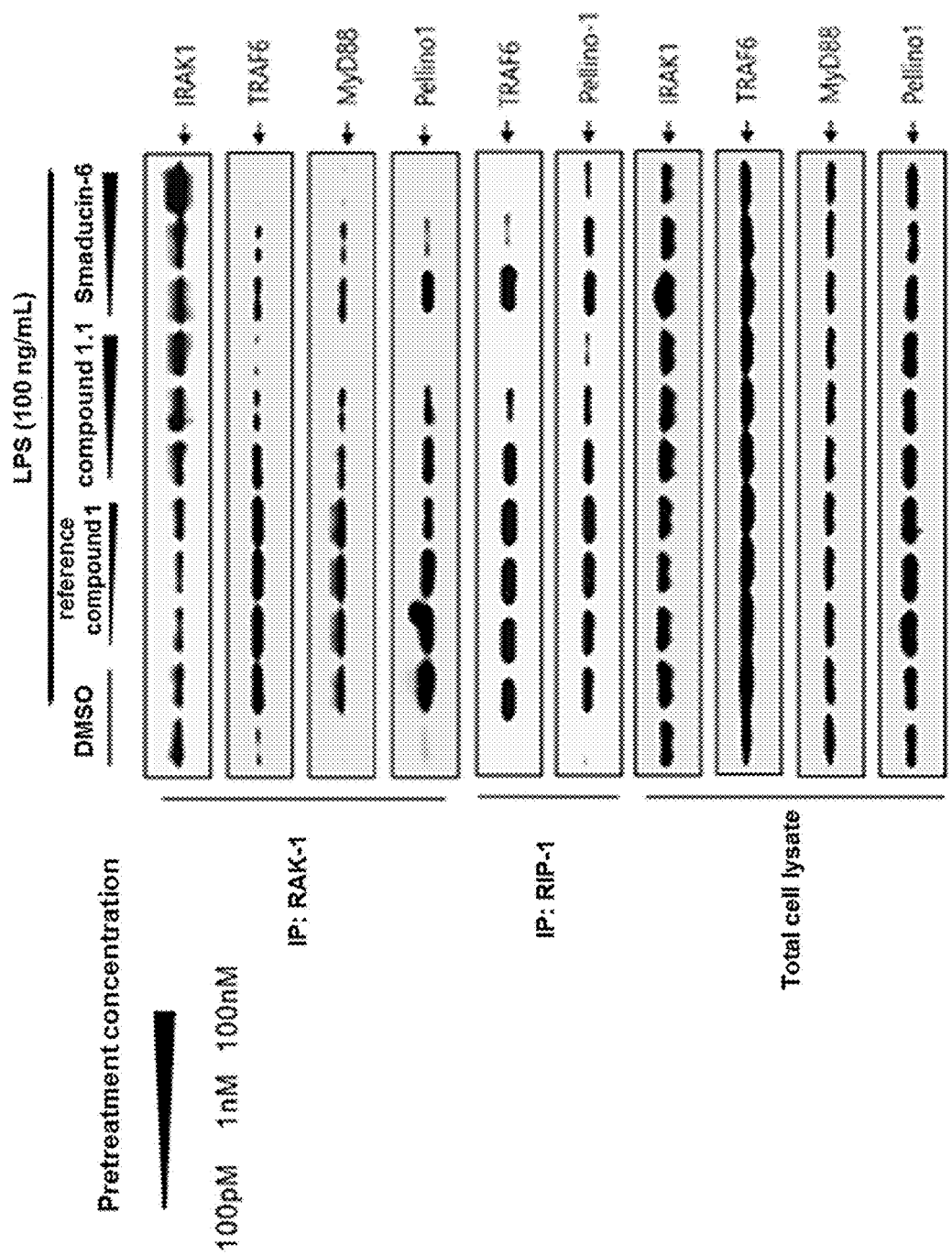
FIG. 8 is an immunoprecipitation result showing that the compounds according to embodiments of the present invention can disrupt formation of inflammation signaling pathway protein complex mediated by IRAK-1, MyD88, and/or RIP1. (Compound 1.1 (SEQ ID NO: 2), Reference compound 1 (SEQ ID NO: 16)).

In case of cells pre-treated with compound 1.1 (SEQ ID NO: 2) as compared to cells pretreated with smaducin-6, formation of the inflammatory signaling pathway complex (for example, Toll-like receptors (TLR)), which was mediated by MyD88 and RIP1, was further disrupted in an increasing dose dependent manner of compound 1.1 (SEQ ID NO: 2) (FIG. 8). Meanwhile, cells pretreated with DMSO or reference compound 1 (SEQ ID NO: 16) formed the inflammatory signaling pathway complex, which is mediated by MyD88 and RIP1 in a non-dose dependent manner.

Likewise, as compared to the control of total cell lysate, when the cells were pre-treated with compound 1.1 (SEQ ID NO: 2) of the present invention, formation of the inflammatory signaling pathway complex, which is mediated by MyD88 and RIP1, was substantially disrupted. The experiments using BMDM cells with the compound of the present invention indicated that the compound of the present invention is effective for preventing and treating multi diseases relating to MyD88, preventing and treating diseases relating to expression of Pellino-1 such as viral infection (respiratory viral infection, viral pneumonia), bacterial pneumonia, autoimmune disease, blood cancer including lymphoma, tumors in various internal organs (e.g., liver, lung, intestine, prostate, pancreas and the like), and preventing and treating multiple sclerosis (MS).

Figure 9A:
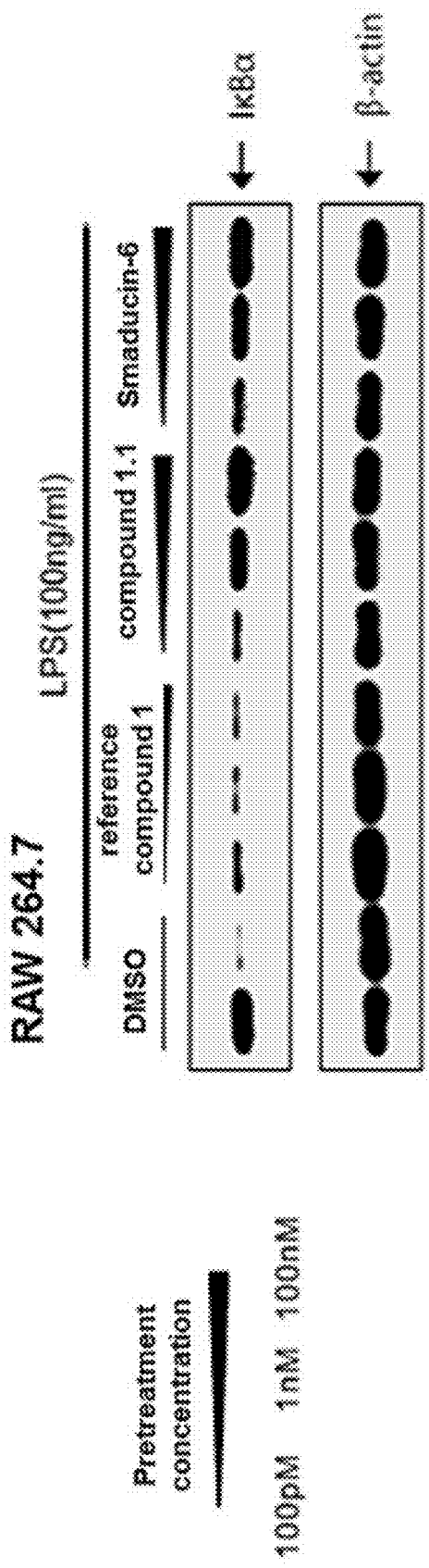
FIGS. 9A and 9B show that change in pretreatment concentration of the compounds according to embodiments of the present invention change concentration of IκB in RAW 264.7 macrophage cells (FIG. 9A) and BMDM cells (FIG. 9B). (Compound 1.1 (SEQ ID NO: 2), Reference compound 1 (SEQ ID NO: 16)).
Figure 9B:
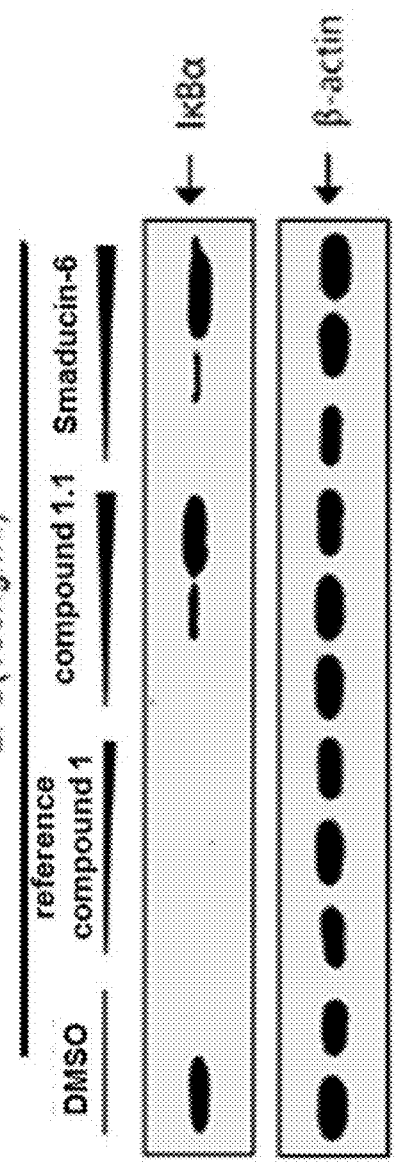

As depicted in FIGS. 9A and 9B, RAW 264.7 macrophage cells (top FIG. 9A) and BMDM cells (FIG. 9B) were individually pretreated with compound 1.1 (SEQ ID NO: 2), reference compound 1 (SEQ ID NO: 16), and smaducine-6 at various concentrations of 100 pM, 1 nM, and 100 nM and then further treated with 100 ng/ml of LPS. The results were compared with expression of reference of β-actin. The expression of IκB was increased in the cells as the dose of pretreated compound 1.1 (SEQ ID NO: 2) and smaducin-6 increased. Meanwhile, IκB was degraded in cells pretreated with DMSO or reference compound 1 (SEQ ID NO: 16) because it was shown to be phosphorylated. Accordingly, compound 1.1 (SEQ ID NO: 2) of the present invention inhibited the degradation of IκB.

Example 2.5

Evaluating Correlation Between Dose and Disease Activity Index

To evaluate the disease activity index of the compounds of the present invention in an animal model with chronic colitis induced by dextran sulfate sodium (DSS), the following experiments were performed.

Mice (7-8 weeks, female, C57BL/6) were fed 2% DSS polymer (MW of about 50000 Da) in drinking water for 5-7 days, and colitis was induced every 2 to 15 days. Compound 1.1 (SEQ ID NO: 2) was then administered orally to the mice, which had induced chronic colitis by DSS, in an amount of 50 mg/kg, 100 mg/kg, 200 mg/kg and 400 mg/kg, respectively, from the third day after feeding DDS, daily, for 11 days. Body weights, diarrhea and hemafecia of the mice were checked daily and the disease activity indexes were measured (FIG. 10).

Figure 10:
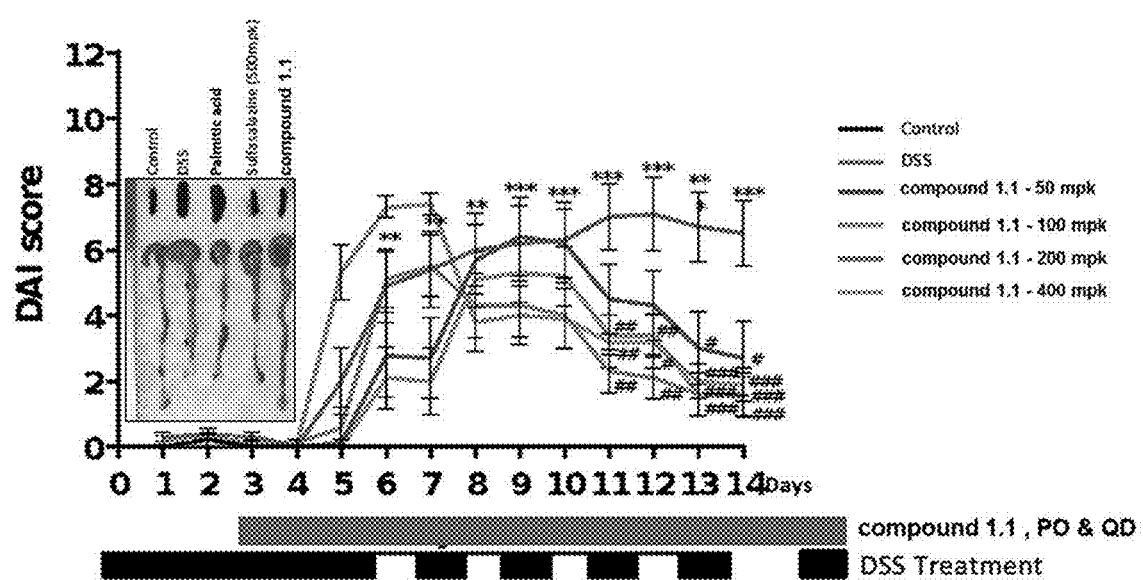
FIG. 10 is a graph indicating disease activity index scores in an animal model with DSS-induced chronic colitis according to the dose of compounds according to embodiments of the present invention in case of oral administration thereof. (Compound 1.1 (SEQ ID NO: 2)).

FIG. 10 is a graph indicating disease activity index scores in the animal model with DSS-induced chronic colitis according to the dose of orally administered compound 1.1 (SEQ ID NO: 2) and compound 1.2. As shown in FIG. 10, when compound 1.1 (SEQ ID NO: 2) of the present invention was administered at different doses from 50 mg/kg to 400 mg/kg, the disease activity thereof was decreased as the dose increased, and the decrease in disease activity was saturated at a dose of 200 mg/kg. Accordingly, the compound of the present invention proportionally-increased activity in a dose dependent manner.

Example 2.6

Suppression of Activity of Bowel Disease

To evaluate the supersession activity of the compounds of the present invention in an animal model with induced acute colitis (which is induced by DSS), the following experiments were performed.

Mice (7-8 weeks, female, C57BL/6) were fed 2% DSS polymer (MW of about 50000 Da) in drinking water for 7-8 days, and colitis was induced. Then, each mouse having acute colitis was administered sulfasalazine in an amount of 500 mg/kg and compound 1.1 (SEQ ID NO: 2) in an amount of 100 mg/kg daily for 14 days. Body weights, diarrhea and hemafecia of the mice were checked daily and disease activity indexes (DAI) were measured (FIG. 11A).

The DAI was measured as follows:
1) weight loss (0 point: no weight loss; 1 point: reduced weight by 1-5%, 2 points: reduced weight by 6-10%, 3 points: reduced weight by 11-20%; 4 points: reduced weight by 20% or greater);
2) diarrhea (0 point: normal bowel movement; 2 points: loose bowel movement; 4 points: diarrhea); and
3) hemafecia (0 point: normal stool; 2 points: mild blood in stool; 4 points: heavy blood in stool).

Figure 11A:
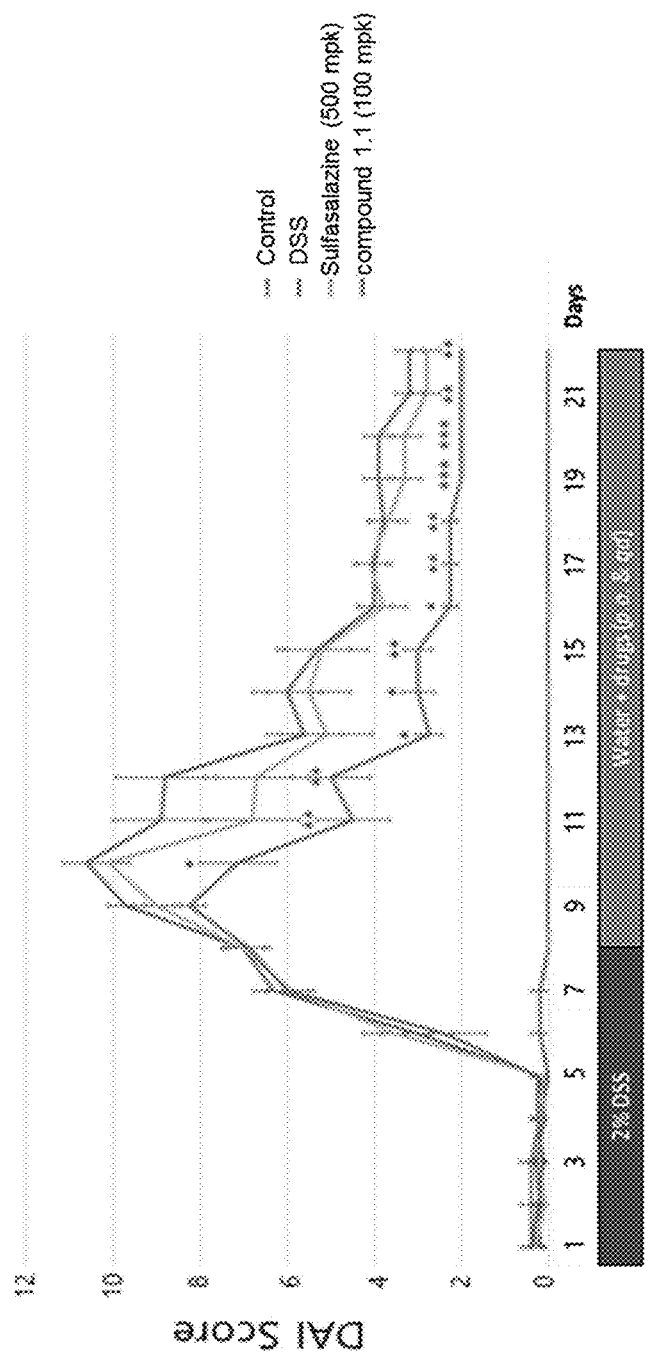
FIG. 11A shows disease activity index scores representing the ability of compounds according to embodiments of the present invention to suppress acute colitis in an animal model with DSS-induced acute colitis. (Compound 1.1 (SEQ ID NO: 2)).

FIG. 11A is a graph indicating disease activity index scores presenting suppression activities of the administered compounds in the animal model with DSS-induced acute colitis. As compared to anti-inflammatory sulfasalazine, the compound of the present invention had sufficient disease activity index score at reduced dose, and thus, the compound of the present invention is more effective for treating colitis (FIG. 11A).

Meanwhile, as shown in FIGS. 11B-11D, mice suffering from chronic colitis induced by DSS were orally administered sulfasalazine in an amount of 500 mg/kg and compound 1.1 (SEQ ID NO: 2) in an amount of 100 mg/kg daily for 10 days. After 10 days of administration, large intestine tissues were obtained from the mice, and expression of chemokines (CCL20, CCL2 and CX3CL1) in the tissues was measured using real-time polymerase chain reaction (Real-Time PCR) as described above. Compound 1.1 (SEQ ID NO: 2) was an effective chemokine blockers by inhibiting chemotaxis of pathogenic immune cells into the inflamed tissues.

Example 2.7

Histological Analyses of Colon Villi

To confirm treatment effect of DDS-induced chronic colitis by compound 1.1 (SEQ ID NO: 2) of the present invention, large intestinal villi from a non-treated group, a DDS-induced chronic colitis model group and a group treated with compound 1.1 (SEQ ID NO: 2) were photographed (FIGS. 12-16).

Figure 12:
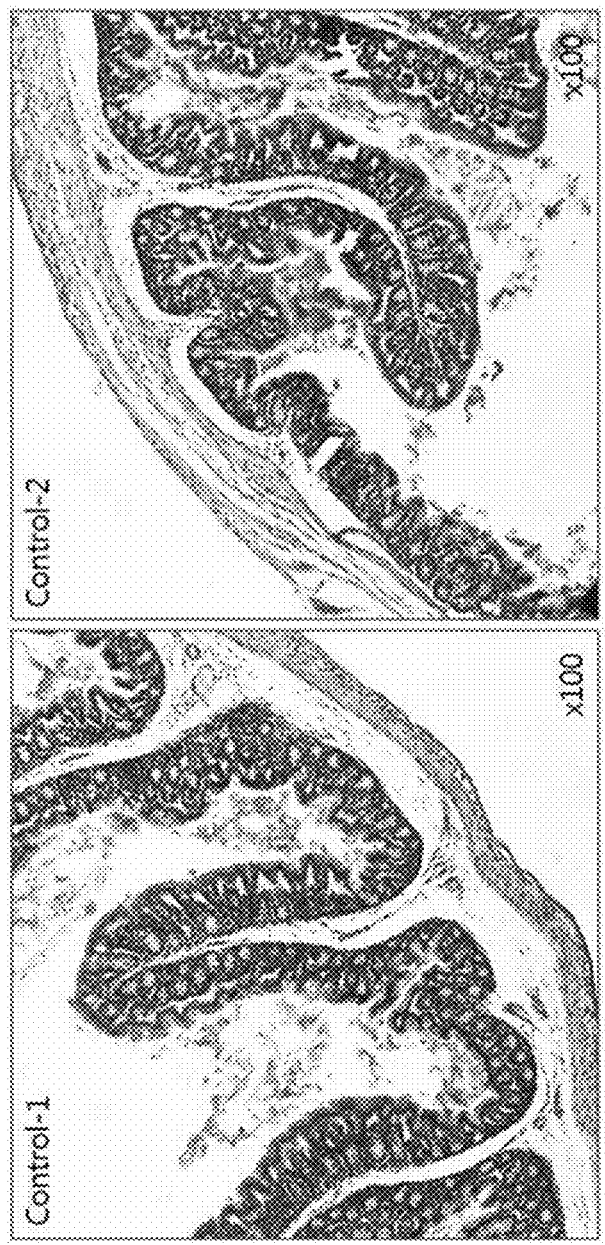
FIG. 12 are images showing shapes of large intestinal villi from a non-treated group.
Figure 13:
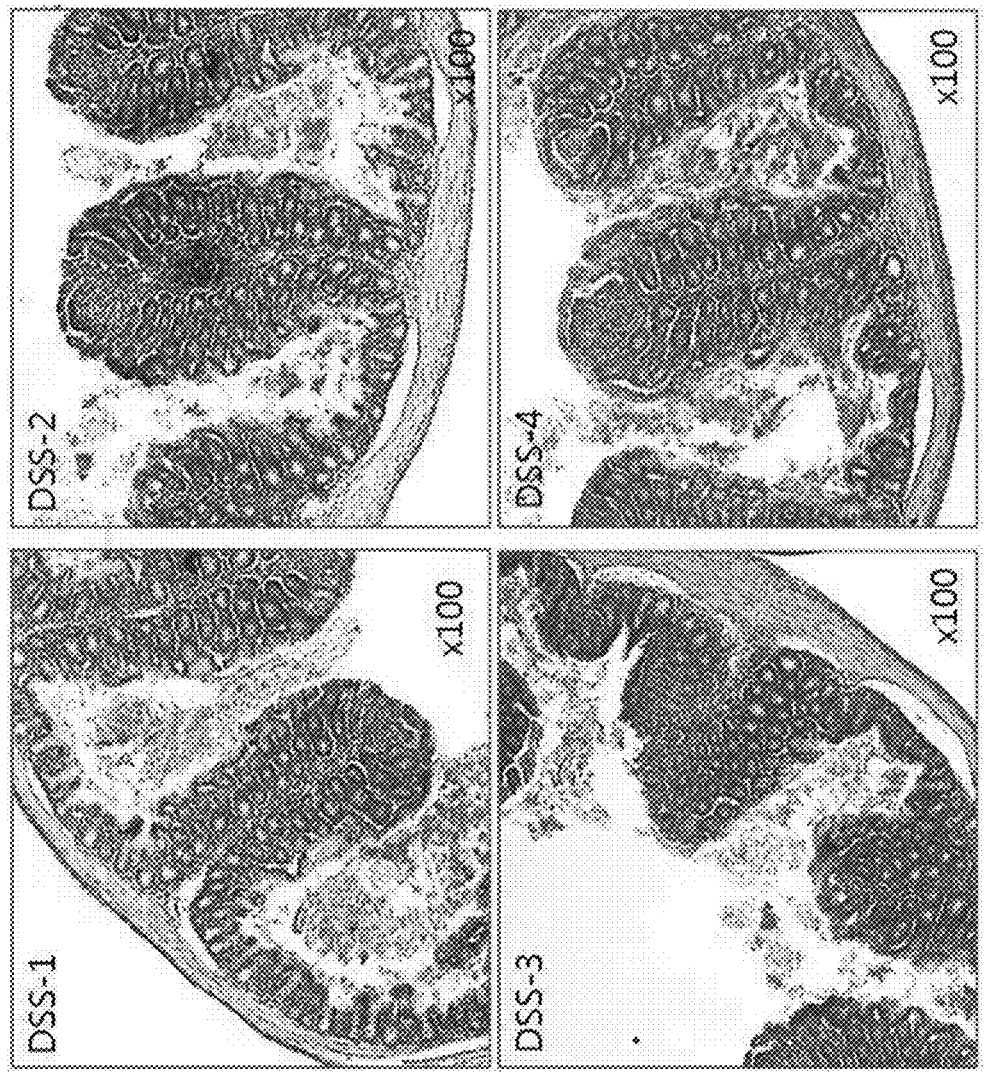
FIG. 13 are images showing shapes of large intestinal villi from a DDS-induced chronic colitis model group.
Figure 14:
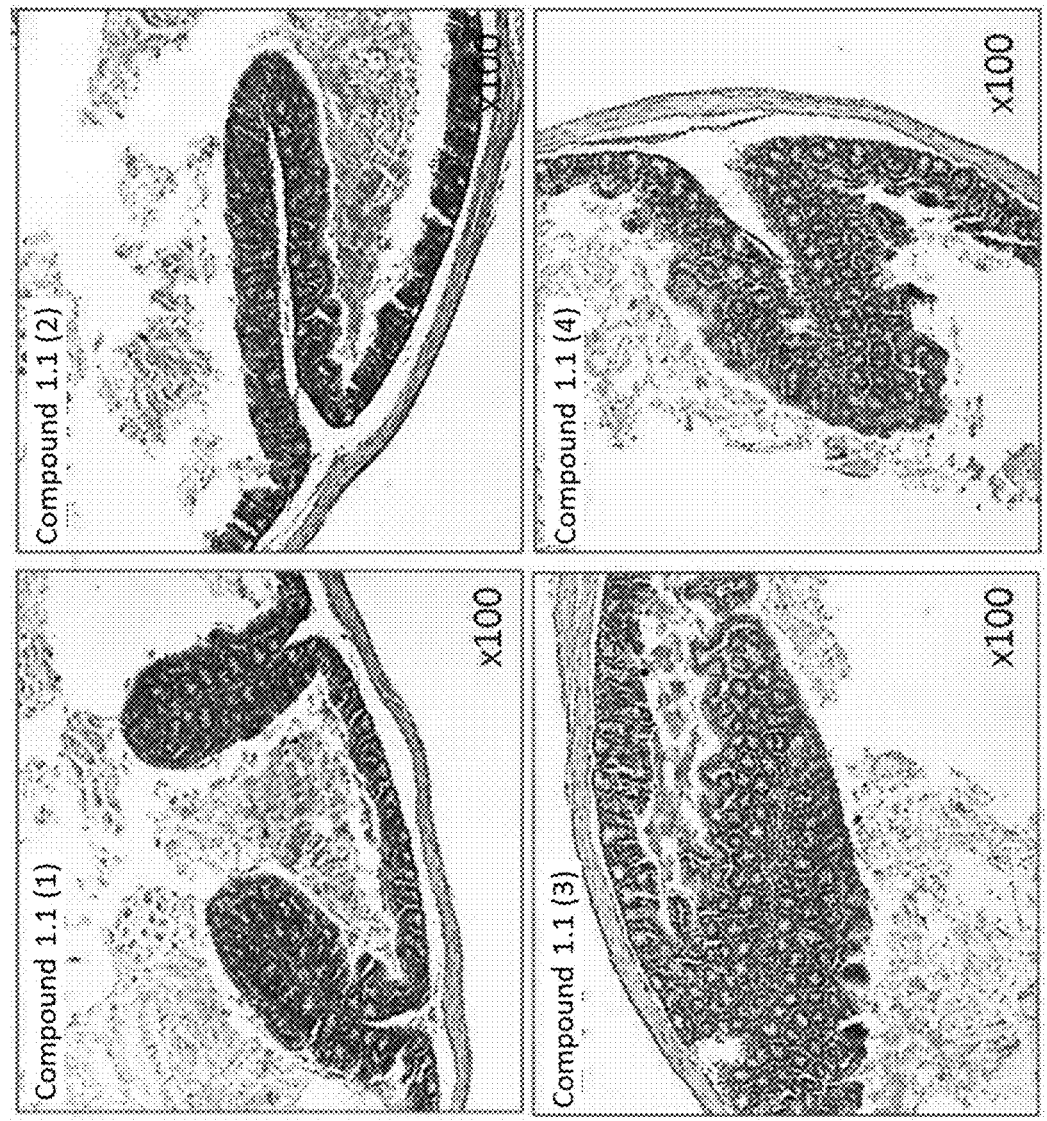
FIG. 14 are images showing shapes of large intestine villi from a group treated with a compound according to embodiments of the present invention. (Compound 1.1 (SEQ ID NO: 2))

FIGS. 12-14 are images showing shapes of the large intestinal villi from the non-treated group, the DDS-induced chronic colitis model group and the group treated with compound 1.1 (SEQ ID NO: 2). As shown in FIGS. 12-14, in comparison to the large intestinal villi from the DSS-induced chronic colitis model, the villi from the group treated with compound 1.1 (SEQ ID NO: 2) were similar to the villi of the non-treated group.

Figure 15:
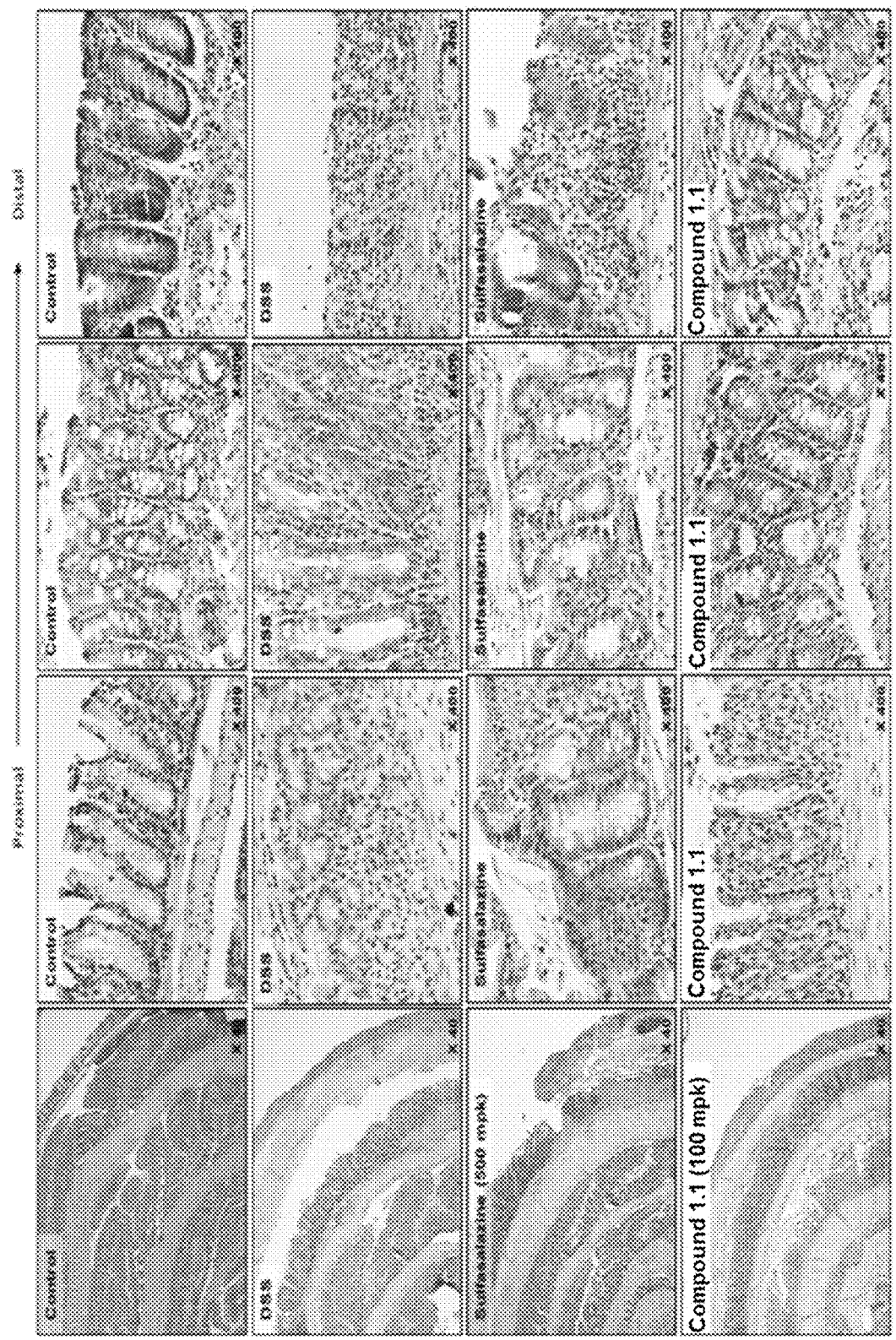
FIG. 15 are images of large intestinal tissues obtained from non-treated group, the DDS-induced chronic colitis model group, the group treated with compound 1.1 (SEQ ID NO: 2) (mpk) and the group treated with sulfasalazine (500 mpk) as an anti-inflammatory drug for colitis treatment.
Figure 16:
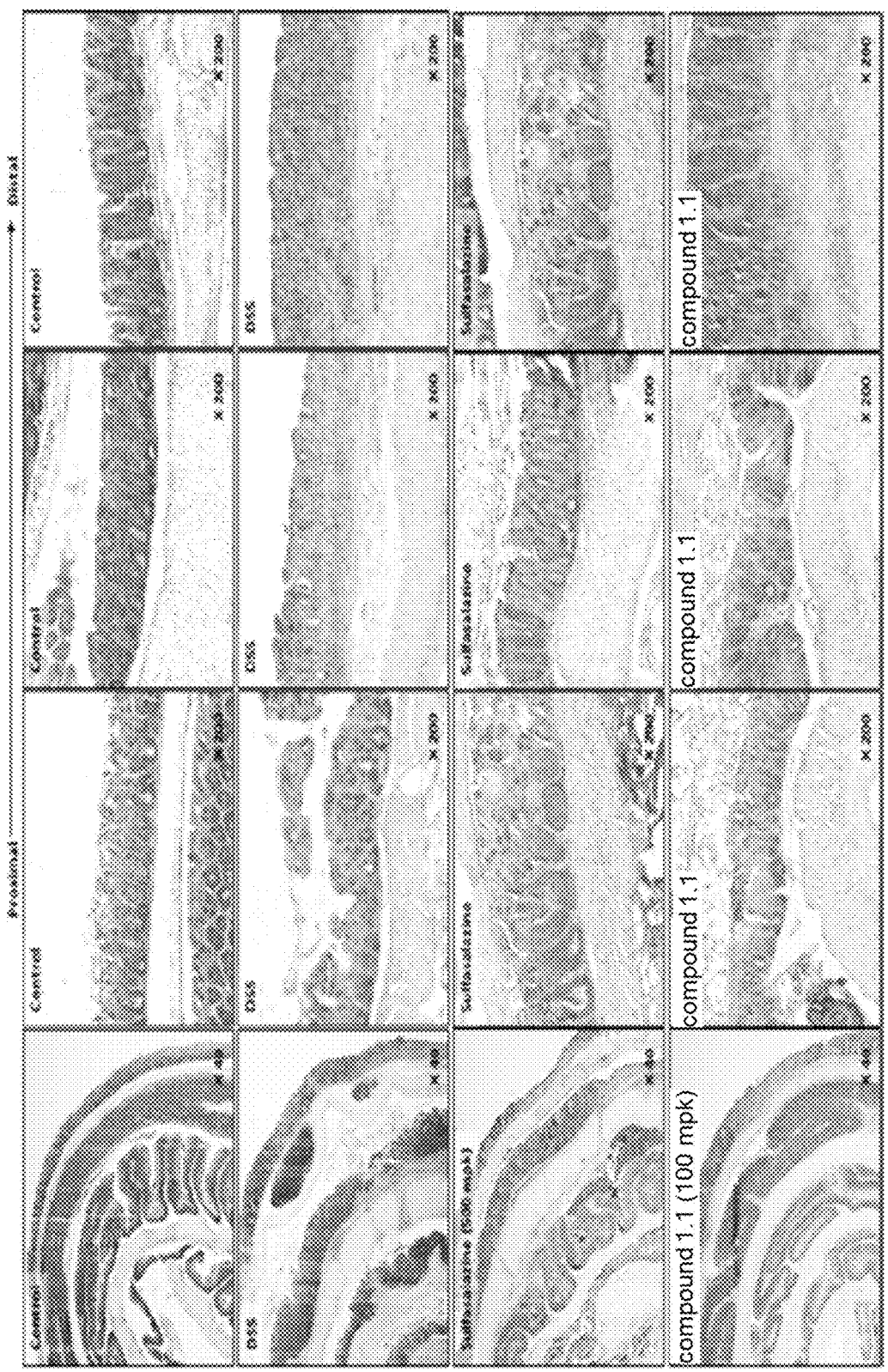
FIG. 16 are images showing the morphology of large intestinal mucous membranes obtained from the non-treated group, the DDS-induced chronic colitis model group, the treated group with compound 1.1 (SEQ ID NO: 2) (100 mpk) and the group treated with sulfasalazine (500 mpk) as an anti-inflammatory drug for colitis treatment.

FIG. 15 shows photographic images of large intestinal tissues obtained from non-treated group, the DDS-induced chronic colitis model group, the group treated with compound 1.1 (SEQ ID NO: 2) (100 mpk) and the group treated with sulfasalazine (500 mpk) as an anti-inflammatory drug for colitis treatment. FIG. 16 shows photographic images of morphology of large intestinal mucous membranes obtained from the non-treated group, the DDS-induced chronic colitis model group, the treated group with compound 1.1 (SEQ ID NO: 2) (100 mpk) and the treated group with sulfasalazine (500 mpk) as an anti-inflammatory drug for colitis treatment, and the mucous membranes were stained with Alcian blue. As shown in FIGS. 15-16, when the DSS-induced chronic colitis model was treated with compound 1.1 (SEQ ID NO: 2), histological damages, which can be found in inflamed tissues, were alleviated. In addition, in comparison to the non-treated group and the group treated with sulfasalazine, the group treated with compound 1.1 (SEQ ID NO: 2) had greater recovery of the mucous membranes by blocking inflamed cells into the tissue.

Figure 17:
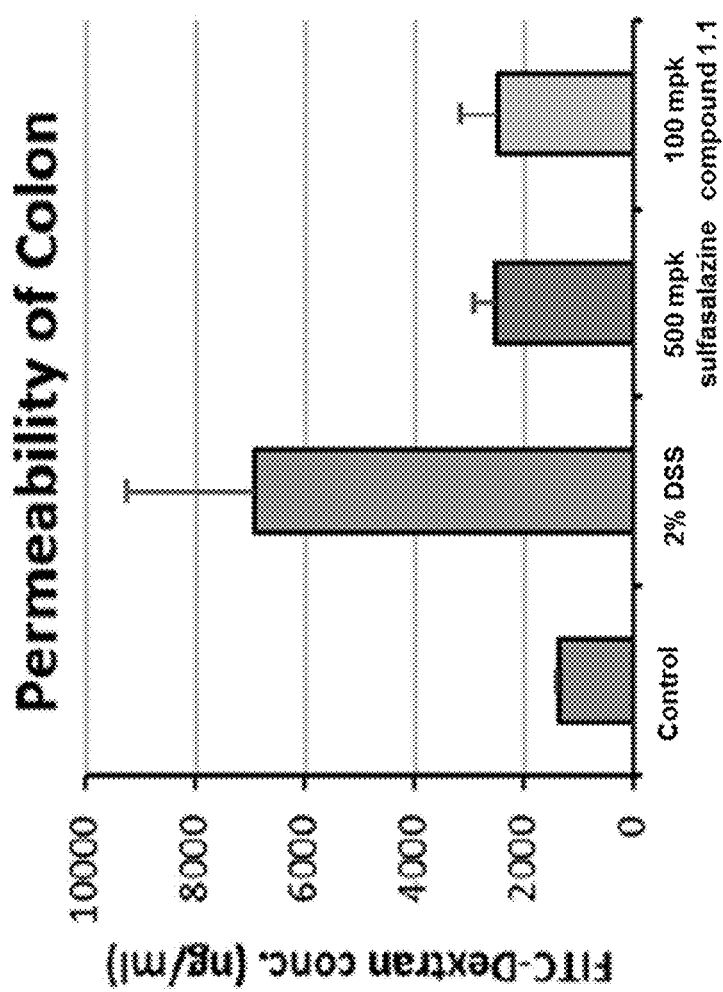
FIG. 17 is a graph showing recovery level of large intestinal wall in a non-treated group, a DDS-induced chronic colitis model group, a group treated with compounds according to embodiments of the present invention (Compound 1.1 (SEQ ID NO: 2)), and a group treated with sulfasalazine.

FIG. 17 is a graph showing recovery level of large intestinal wall in the non-treated group, the DDS-induced chronic colitis model group, the treated group with compound 1.1 (SEQ ID NO: 2) (100 mpk) and the treated group with sulfasalazine (500 mpk).

Specifically, as described in *Nature Protocols*, 8(3), (2013) 627-637, on the 8th day 8 of treatment in DDS-induced chronic colitis models, FITC-Dextran was orally administered at dose of 44 mg per 100 g body weight. After four hours of administration, blood in an amount of 300-400 µL was collected from heart of the mice. The FITC-Dextran released in blood stream was measured using a spectrophotofluorometer.

FIG. 17 quantitatively shows that, by analyzing the FITC-Dextran released in blood stream, tight junction in large intestinal epithelial tissue caused by embolization of large intestinal mucous membrane, or function at the large intestinal wall were recovered as much as the current sulfasalazine treatment. Accordingly, the compound of the present invention had a significant effect on recovering the intestinal epithelial barrier and tight junction functions in chronic colitis tissues.

Example 2.8

Plasma Concentration

To evaluate changes of the blood (blood stream) concentration of intravenous and oral administration of compound 1.1 (SEQ ID NO: 2) of the present invention, the following experiments were performed.

Figure 18:
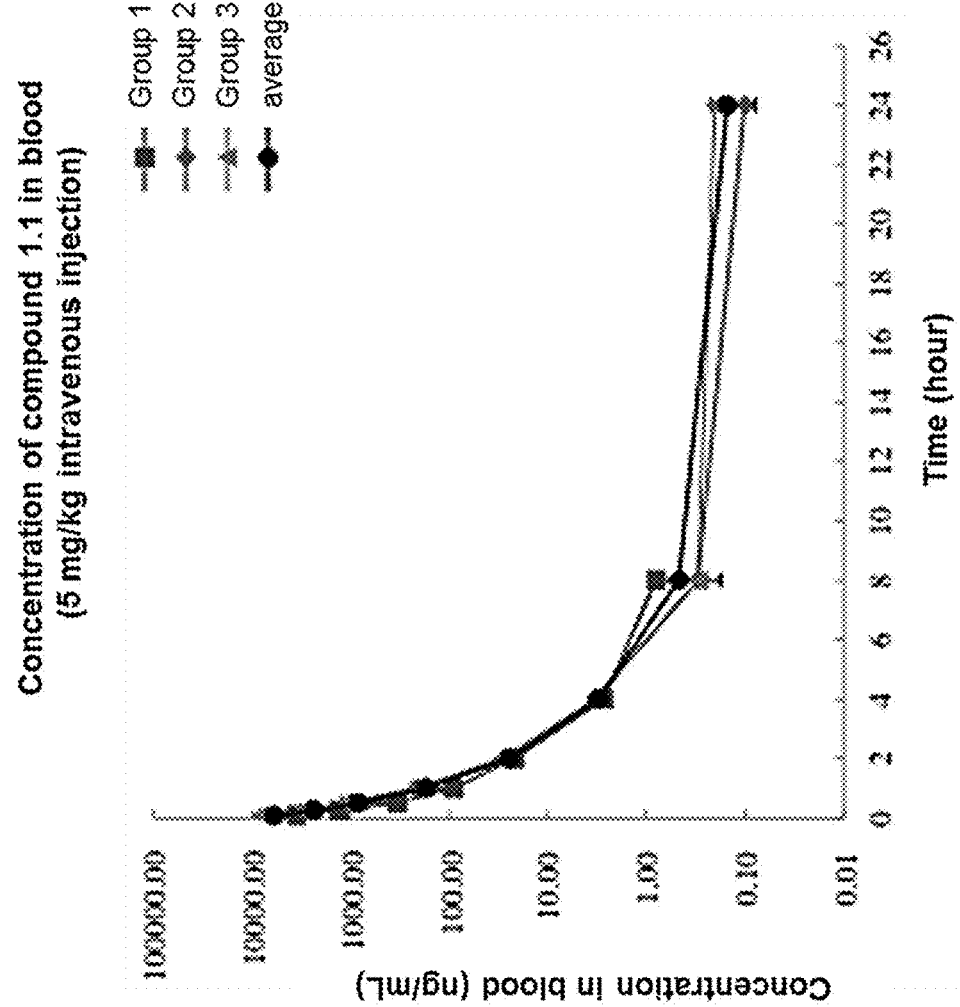
FIG. 18 is a graph showing changes in blood concentration over time of compounds according to embodiments of the present invention (Compound 1.1 (SEQ ID NO: 2)) via intravenous administration.
Figure 19:
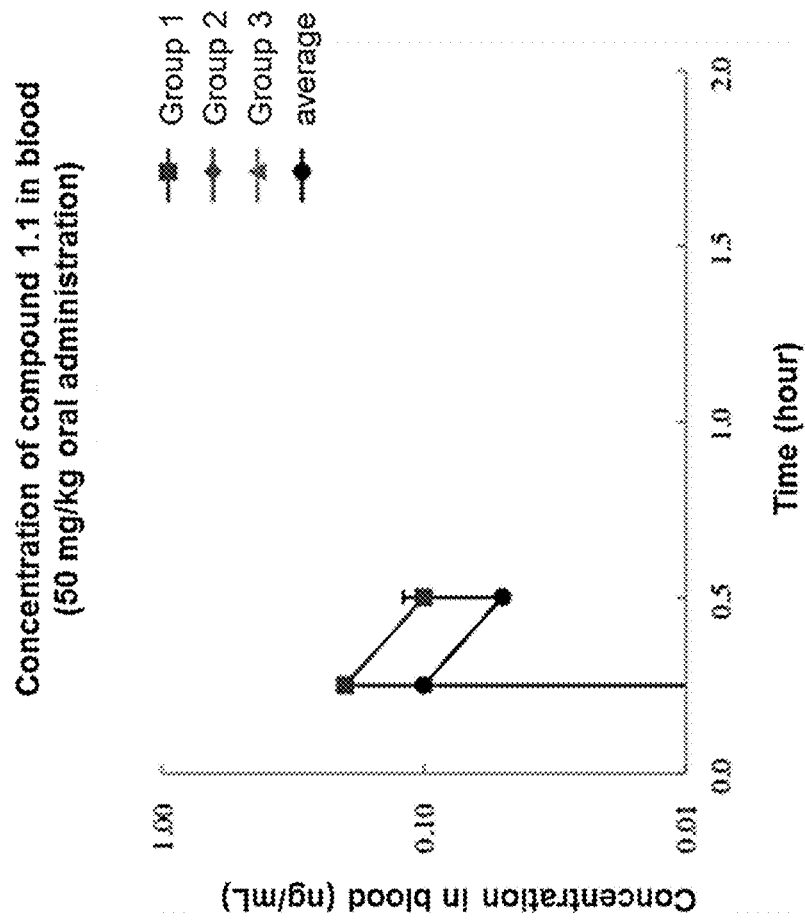
FIG. 19 is a graph showing changes in blood concentration over time of compounds according to embodiments of the present invention (Compound 1.1 (SEQ ID NO: 2)) via oral administration.

Compound 1.1 (SEQ ID NO: 2) was administered to a rat intravenously (I.V., 5 mg/kg) or orally (50 mg/kg), and 24 hours after administration, the concentration of compound 1.1 (SEQ ID NO: 2) in plasma was measured (FIG. 18 and FIG. 19).

Changes in the concentration of the compound 1.1 (SEQ ID NO: 2) when intravenously administered at various time intervals were measured (FIG. 18). The concentration was decreased to 1/100 of the initial concentration thereof within 1-2 hours and within 8 hours from the administration. Compound 1.1 (SEQ ID NO: 2) was detected in blood at very low concentration.

Changes in the blood concentration of compound 1.1 (SEQ ID NO: 2) at various time courses when orally administered were measured (FIG. 19). After 30 minutes from the oral administration, compound 1.1 (SEQ ID NO: 2) was not detected in blood.

Table 2 shows pharmacokinetic parameters of compound 1.1 (SEQ ID NO: 2).

TABLE 2

Pharmacokinetic parameters of compound 1.1 (SEQ ID NO: 2)

| | Profile | 5 mg/kg (i.v.) | 50 mg/kg (p.o.) |
|---|---|---|---|
| In vivo PK (Rat, single dose) | Animal | Male SD rat | Male SD rat |
| | Cmax (ng/mL) | 6,017.3 ± 2,302.4 | 0 |
| | Tmax (hr) | 0.08 | 0 |
| | AUClast (ng · hr/mL) | 2,135.6 ± 848.1 | 0 |
| | T½ (hr) | — | 0 |
| | Vss (L/kg) | 5.4 ± 1.0 | — |
| | CL (L/hr/kg) | 2.7 ± 1.3 | — |

Example 2.9

Tissue Distribution

To evaluate tissue distribution of compound 1.1 (SEQ ID NO: 2) according to the present invention, the following experiments were performed.

Compound 1.1 (SEQ ID NO: 2) was orally administered to a rat at dose of 10 mg/kg, and after 2 hours and 8 hours, concentrations of compound 1.1 (SEQ ID NO: 2) were measured in the small intestinal tissue, large intestinal tissue, appendix tissue, retrimentum in small intestine and retrimentum in large intestine. The results are shown in the following Table 3.

TABLE 3

Concentration of compound 1.1 (SEQ ID NO: 2) after oral administration

| Species | Concentration (ng/mL) | |
|---|---|---|
| | 2 hours | 8 hours |
| small intestinal tissue | 75 ± 70.2 | 78.1 ± 59.9 |
| large intestinal tissue | 30 ± 10 | 33.2 ± 28.8 |
| appendix tissue | 22.7 ± 2.56 | 48.2 ± 46 |
| retrimentum in small intestine | 1118 ± 217 | 876 ± 900 |
| retrimentum in large intestine | ND | 1278 ± 52.7 |

ND: Not Determined

Quantitation range: intestine 8-2000 ng/kg, retrimentum 30-1000 ng/mL

As shown in Table 3, compound 1.1 (SEQ ID NO: 2) was distributed in intestinal tissues such as small intestinal, large intestinal and appendix tissues at 2 hours and 8 hours from administration in a quantitative range, and further compound 1.1 (SEQ ID NO: 2) was distributed in internal tissues 8 hours after administration.

Accordingly, when orally administered, an effective concentration of the compound of the present invention is continuously maintained in intestinal tissues, even after 8 hours. Because the compound of the present invention is a small molecule drug, the compound can be readily taken up into the intestines such that effective concentration thereof may be readily reached. Accordingly, by oral administration, the compound described herein may be used for efficiently treating inflammatory bowel diseases.

Example 2.10

Inhibition of Activity of MAPK Signaling Pathway

Figure 20A:
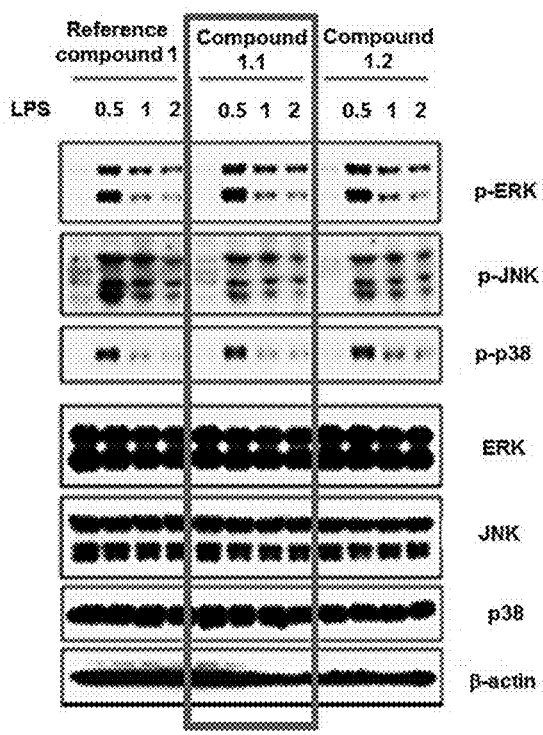
FIG. 20A is a Western blot image confirming whether compounds according to embodiments of the present invention (Compound 1.1 (SEQ ID NO: 2)) inhibit MAPK/ERK signaling pathway.
Figure 20B:
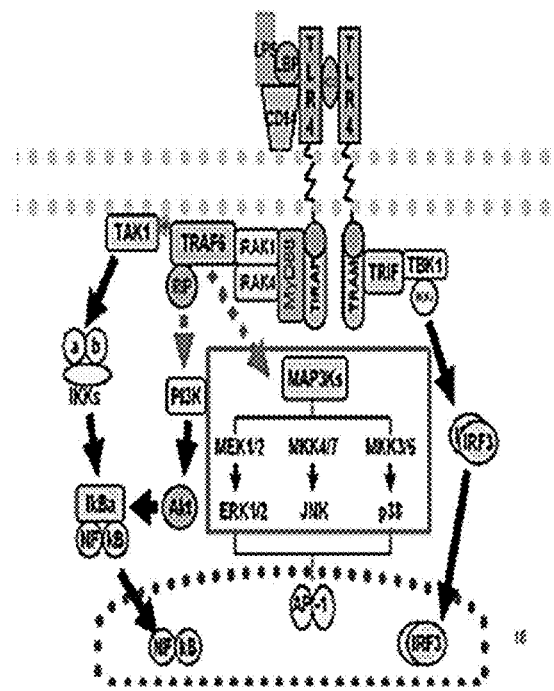
FIG. 20B is a diagram depicting signaling pathway of toll-like receptors.

To test whether compound 1.1 (SEQ ID NO: 2) and compound 1.2 of the present invention suppress MAPK/ERK signaling pathway, Western blot analysis was performed (FIG. 20A).

RAW 246.7 macrophage cells were pretreated with compound 1.1 (SEQ ID NO: 2), compound 1.2 and reference compound 1 (SEQ ID NO: 16) at a concentration of 100 nM for 30 minutes and then further treated with LPS for 0 hour, 0.5 hour, 1 hour and 2 hours. Phosphorylation of MAPK signaling pathway proteins (ERK1/2, JNK, p38) from the cell treated with compound 1.1 (SEQ ID NO: 2), and compound 1.2 were activated at 0.5 hour with the same pattern as the case of reference compound 1 (SEQ ID NO: 16), and after 1 hour or 2 hours of treatment, phosphorylation of those proteins were gradually decreased with the same pattern as the case with reference compound 1 (SEQ ID NO: 16). β-actin was used as reference control. Changes of the concentration upon phosphorylation of each protein were measured by immunoblotting using anti-phosphorylation antibodies. Reference compound 1 (SEQ ID NO: 16), compound 1.1 (SEQ ID NO: 2) and compound 1.2 did not inhibit phosphorylation of the MAPK signaling pathway proteins.

Figure 21:
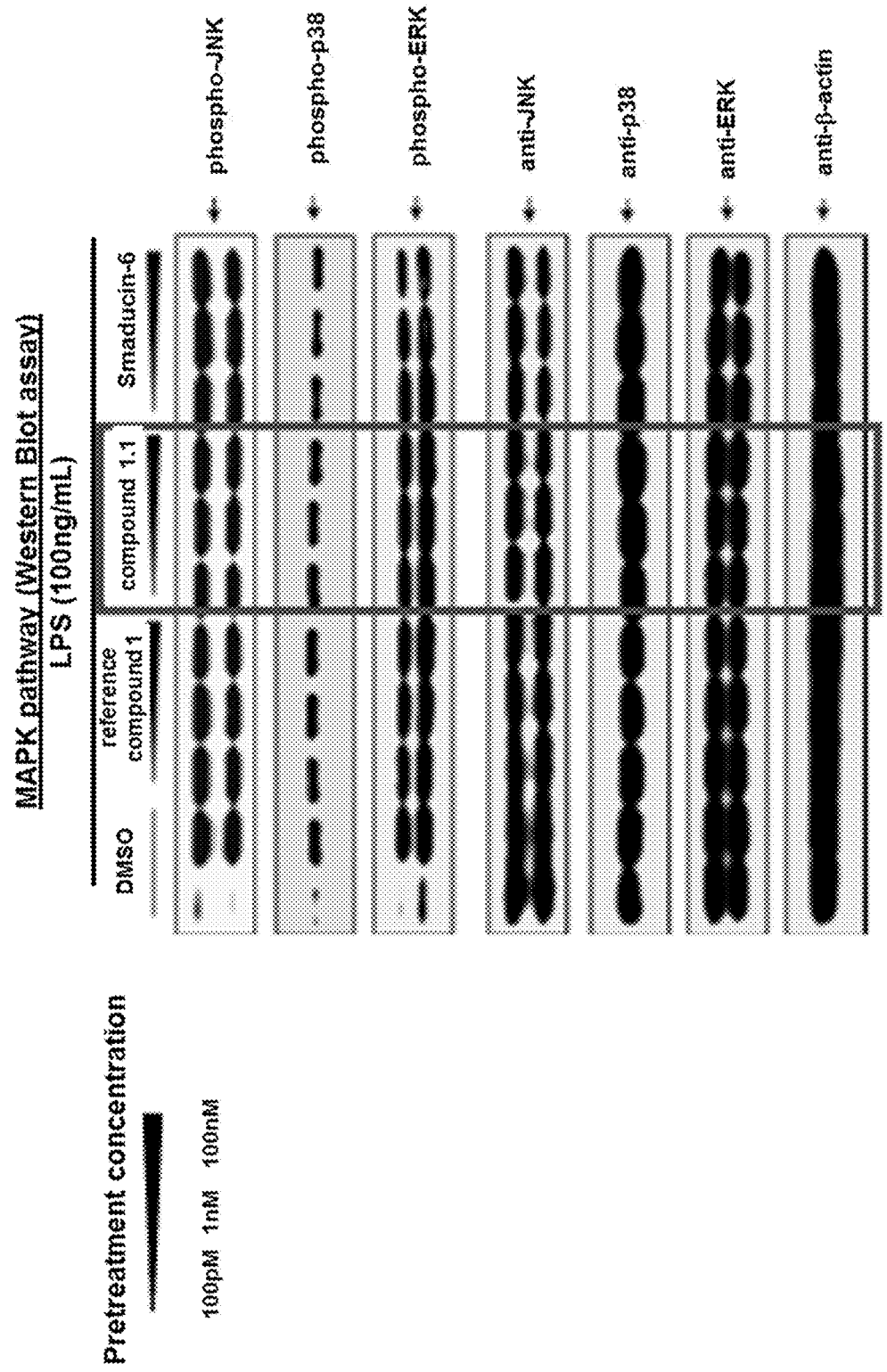
FIG. 21 is a Western blot image confirming whether compounds according to embodiments of the present invention inhibit MAPK/ERK signaling pathway. (Compound 1.1 (SEQ ID NO: 2), Reference compound 1 (SEQ ID NO: 16)).

FIG. 21 shows images determining the inhibition of phosphorylation of MAPK signaling pathway proteins (ERK1/2, JNK, p38). BMDM cells were pretreated with DMSO, reference compound 1 (SEQ ID NO: 16), compound 1.1 (SEQ ID NO: 2) and smaducin-6 at various concentrations of 100 pM, 1 nM and 100 nM and then further treated with LPS 2 hours. Thereafter, Western blot analysis was performed. Compound 1.1 (SEQ ID NO: 2) according to the present invention was not related to suppressing phosphorylation of MAPK/ERK signaling pathway proteins despite increase of dose, which was similar to DMSO and reference compound 1 (SEQ ID NO: 16).

Example 2.11

Comparison with IRAK1/4-Inhibitor

As described in Example 2.3, 5×NF-κB-Luc reporter plasmid was transfected into RAW 246.7 macrophage cells. After 24 hours, the cells transfected with NF-κB-Luc reporter plasmid were pretreated with compound 1.1 (SEQ ID NO: 2) (100 nM), interleukin-1-receptor-associated-kinase-1/4 inhibitor (IRAK1/4) inhibitor (25 μM, CAS 509093-47-4), and smaducin-6 (100 nM) for 30 minutes, and then further treated with LPS (100 ng/ml) for 2 hours. Subsequently, luciferase activities in the cells were measured.

Figures 22A, 22B:
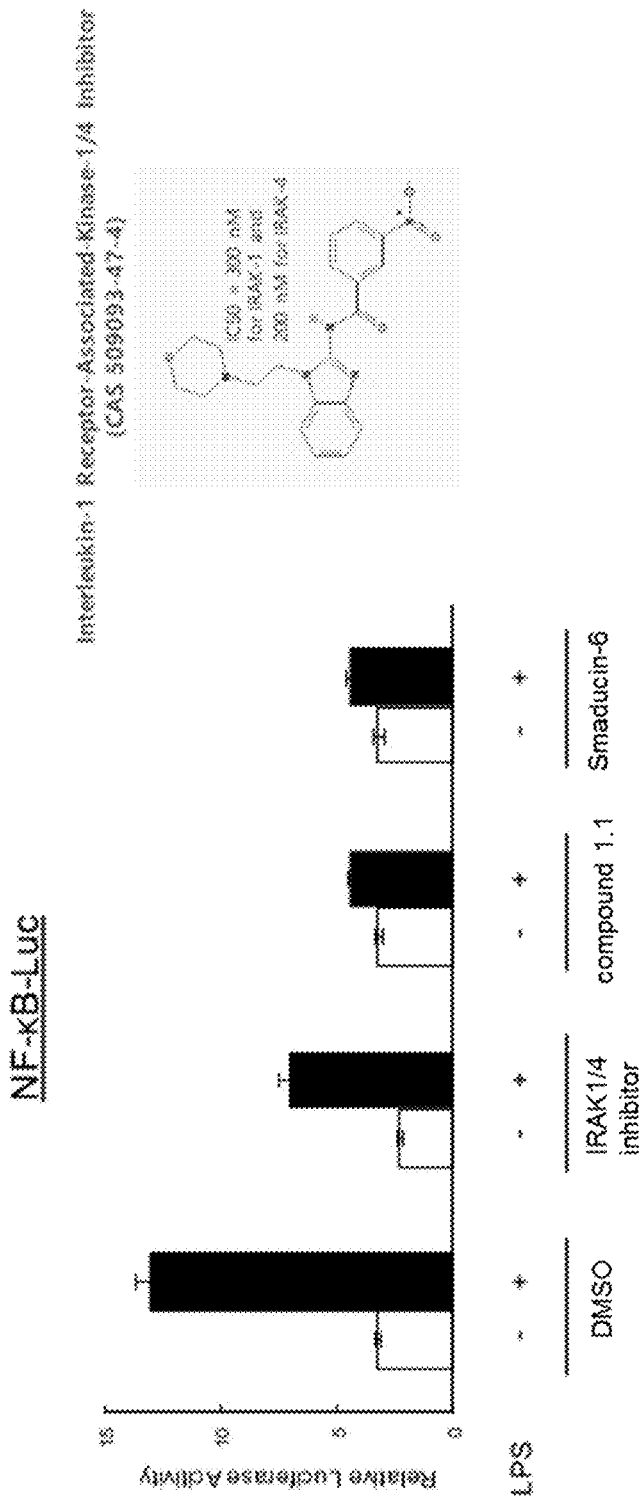
FIG. 22A and FIG. 22B show the inhibition level of NF-κB activation by compounds according to embodiments of the present invention (FIG. 22A) (Compound 1.1 (SEQ ID NO: 2)) and an IRAK1/4 inhibitor (FIG. 22B), respectively.

FIGS. 22A and 22B show inhibition of NF-κB activation by compound 1.1 (SEQ ID NO: 2) (FIG. 22A) and IRAK1/4 inhibitor (FIG. 22B) relatively. At a high IRAK1/4 inhibitor concentration (e.g. 25 μM), NF-κB activation was inhibited, which was similar to compound 1.1 (SEQ ID NO: 2).

Figure 23A:
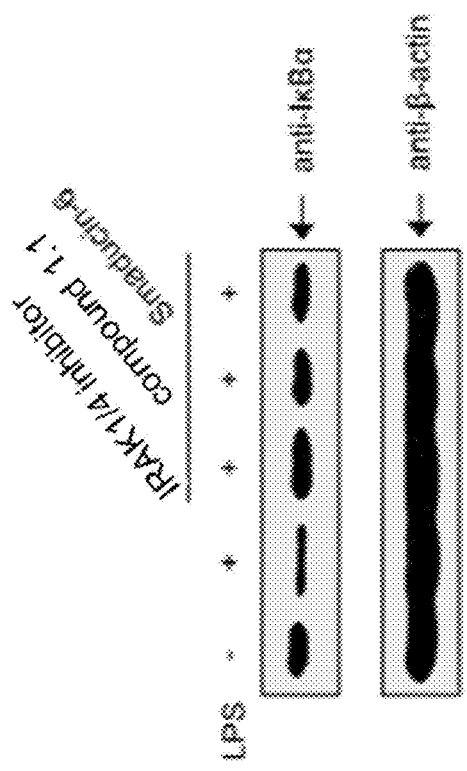
FIGS. 23A and 23B are immunoblot images confirming whether compounds according to embodiments of the present invention and an IRK1/4 inhibitor change the concentration of IκB.
Figure 23B:
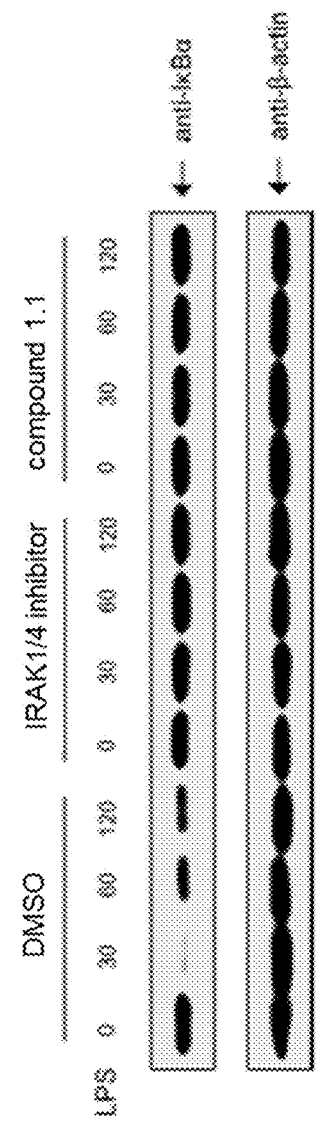

Changes in IκB concentration in the cell lysate of RAW 246.7 macrophage cells, which were pretreated with compound 1.1 (SEQ ID NO: 2) (100 nM), IRAK1/4 inhibitor (25 μM) and smaducin-6 (100 nM) and then further treated with LPS (100 ng/ml), were measured (FIG. 23A). RAK1/4 inhibitor also suppressed degradation of IκB similar to compound 1.1 (SEQ ID NO: 2) (FIG. 23B).

Figures 24A, 24B:
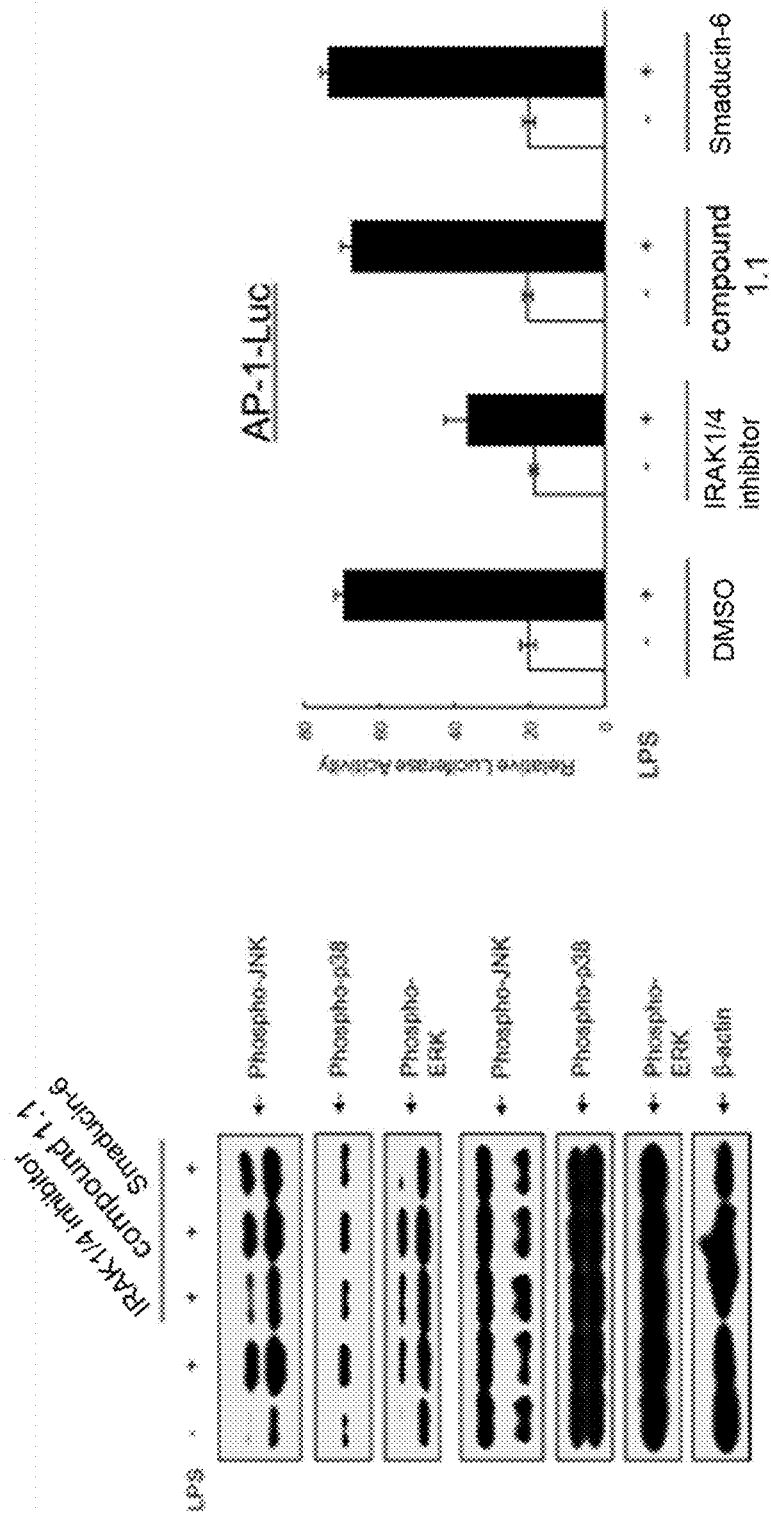
FIG. 24A and FIG. 24B are an image and a graph, respectively, comparing the ability of compounds according to embodiments of the present invention to inhibit MAPK/ERK signaling pathway and the ability of an IRAK1/4 inhibitor to inhibit MAPK/ERK signaling pathway. (Compound 1.1 (SEQ ID NO: 2))

FIGS. 24A and 24B shows a graph and images comparing suppression of MAPK/ERK signaling pathway by compound 1.1 (SEQ ID NO: 2) and IRAK1/4 inhibitor. Specifically, RAW 246.7 macrophage cells were pretreated with DMSO, compound 1.1 (SEQ ID NO: 2) (100 nM), IRAK1/4 inhibitor (25 μM), and smaducin-6 (100 nM) for 30 minutes, and then further treated with LPS (100 ng/ml) for two hours. FIG. 24A specifically shows immunoblotting results to evaluate whether phosphorylation of MAPK signaling pathway proteins such as ERK, JNK, and p38 were inhibited by the above treatment. β-actin was used as reference. Compound 1.1 (SEQ ID NO: 2) and smaducin-6 neither suppressed MAPK signaling pathway nor inhibited phosphorylation of the proteins. In contrast, IRAK1/4 inhibitor suppressed at least one or more of MAPK signaling pathways.

In addition, to check for an unexpected side effect (e.g., from the fact that IRAK1/4 inhibitor suppresses AP-1 transcription signal in MAPK pathway induced with LPS, which is in contrary to compound 1.1 (SEQ ID NO: 2)), the following experiments were performed.

RAW 246.7 macrophage cells were transfected with AP-1-Luc reporter plasmid as described in Example 2.3. After 24 hours, the transfected cells with AP-1-Luc reporter plasmid were pretreated with compound 1.1 (SEQ ID NO: 2) (100 nM), IRAK1/4 inhibitor (25 μM), and smaducin-6 (100 nM) for 30 minutes, and then further treated with LPS (100 ng/ml) for 2 hours. Luciferase activity in the cells was measured and results are presented in FIG. 24B. Compound 1.1 (SEQ ID NO: 2) of the present invention selectively inhibited activity of NF-κB signaling pathway, but did not suppress MAPK signaling pathways which is important to biological activity of cells. However, IRAK1/4 inhibitor inhibited MAPK signaling pathway, which may result in inhibiting AP-1 transcriptional factors, such that, when applied in biological subject, unexpected side effects may occur.

The results in Examples 2.1 to 2.11 above indicated that the compounds of the present invention can (1) inhibit expression of interleukin-6 and activity of NF-κB, which are induced with LPS treatment; (2) disrupt inflammatory signaling pathways mediated by MyD88 and RIP1; and (3) provide similar disease activity index at less dose than the dose of sulfasalazine that is current anti-inflammatory drug for colitis. In addition, when the compounds in the present invention are orally administrated, concentration in blood stream is low, whereas the effective concentration is maintained in cells and/or tissues. In particular, in intestinal tissues, the effective concentration thereof can be maintained even after 8 hours of administration. Accordingly, the compounds of the present invention are used for treating inflammatory disease in intestinal tissues, and particularly, are effectively used for preventing, alleviating and treating inflammatory bowel disease such ulcerative colitis, Behcet's Disease, Crohn's disease and the like.

Example 2.12

Effect on Retinal Pigment Epithelium Cells

Compound 1.1 (SEQ ID NO: 2) influenced angiogenesis related factors or suppression factors.

ARPE-19 cells were treated with 5.5 mM of glucose as reference control. For experiment group, the ARPE-19 cells were treated with 30 mM of glucose for 48 hours to induce high blood glucose condition, and simultaneously treated with DMSO, compound 1.1 (SEQ ID NO: 2) (10 nM), and compound 1.1 (SEQ ID NO: 2) (50 nM). Changes in expression of Nox-4, VEGF, VEGFR1, VEGFR2, Ang1, Ang2, Tie-2, EPO, and EPOR proteins were measured by Western blot analysis.

Figure 25B:
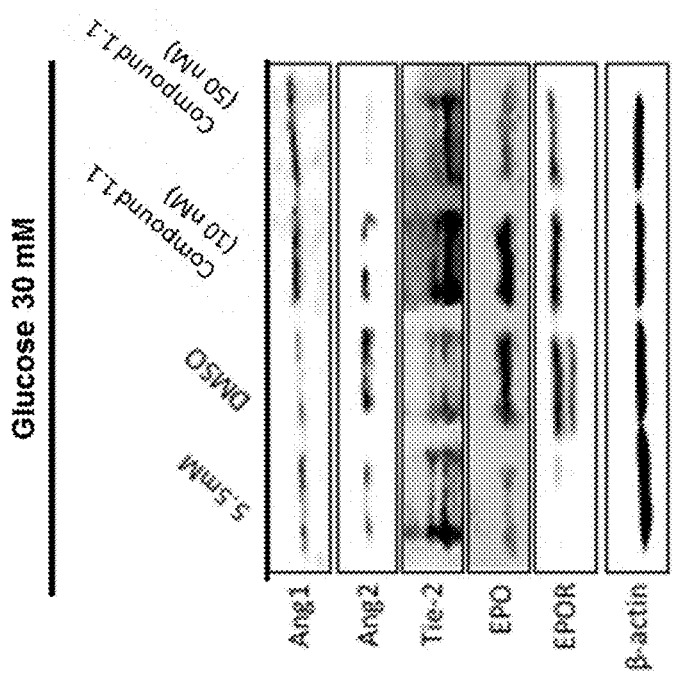
FIGS. 25A and 25B are Western blot images confirming whether compounds according to embodiments of the present invention suppress, in ARPE-19, expression of Nox-4, VEGF, VEGFR1, VEGFR2, Ang-2, EPO, and EPOR and can increase the expression of Ang-1 and Tie2.
Figure 25A:
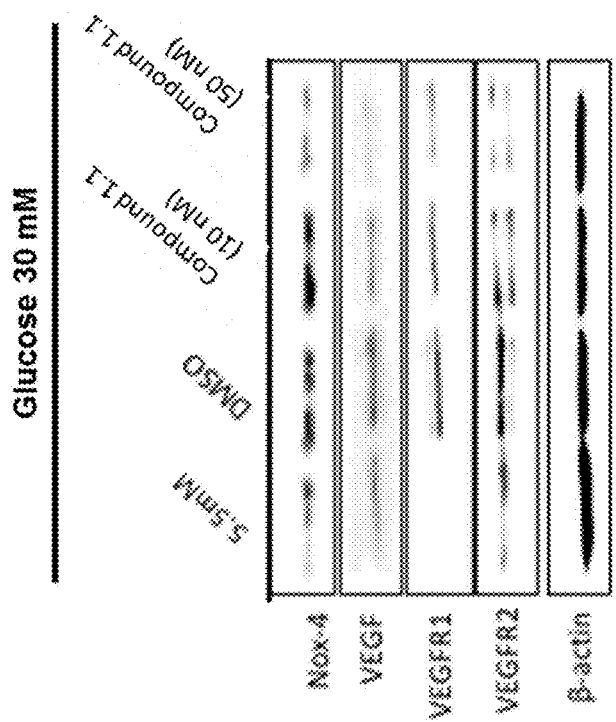

Ang1 and Tie-2, which are factors controlling hemorrhage by reinforcing blood vessel, were increased according to increased concentration of compound 1.1 (SEQ ID NO: 2) (FIGS. 25A and 25B). However, expression of Nox4 of producing factor of ROS (reactive oxygen species), VEGF of inducing factor of new blood vessel, VEGFR1,2, Ang2 of antagonizing factor for Ang1, and EPO and EPOR of factors for diabetic retinopathy was reduced by treating with compound 1.1 (SEQ ID NO: 2).

Figure 25C:
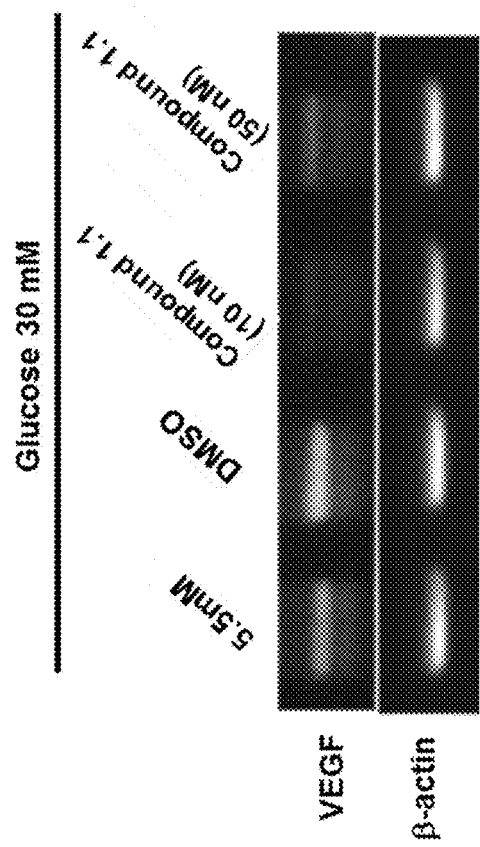
FIG. 25C is a qRT-PCR image confirming whether compounds according to embodiments of the present invention (Compound 1.1 (SEQ ID NO: 2)) suppress the expression of VEGF in HRMEC.

In addition, HRMEC cells were treated with 5.5 mM of glucose for reference group. For experiment group, the HRMEC cells were treated with 30 mM of glucose for 48 hours to induce high blood glucose condition, and simultaneously treated with DMSO, compound 1.1 (SEQ ID NO: 2) (10 nM), and compound 1.1 (SEQ ID NO: 2) (50 nM). Changes in expression of Nox-4, VEGF, VEGFR1, VEGFR2, Ang1, Ang2, Tie-2, EPO, and EPOR proteins were quantitatively measured by qRT-PCR (quantitative RT-PCR). Expression of VEGF precursor as stimulating factor of new blood vessel was reduced by treatment with compound 1.1 (SEQ ID NO: 2) (FIG. 25C).

To evaluate the effect of compound 1.1 (SEQ ID NO: 2) on tube formation during angiogenesis, HRMEC cells (8×3) were cultured on Matrigel coated micro slides and treated with 20 ng/ml of VEGF for 4 hours to induce the tube formation. Simultaneously, for reference group, the cells were treated with DMSO, and for experimental group, the cells were treated with 50 nM of compound 1.1 (SEQ ID NO: 2) and 1 uM of calcein-AM. The cells were observed using fluorescence microscope.

Figure 26:
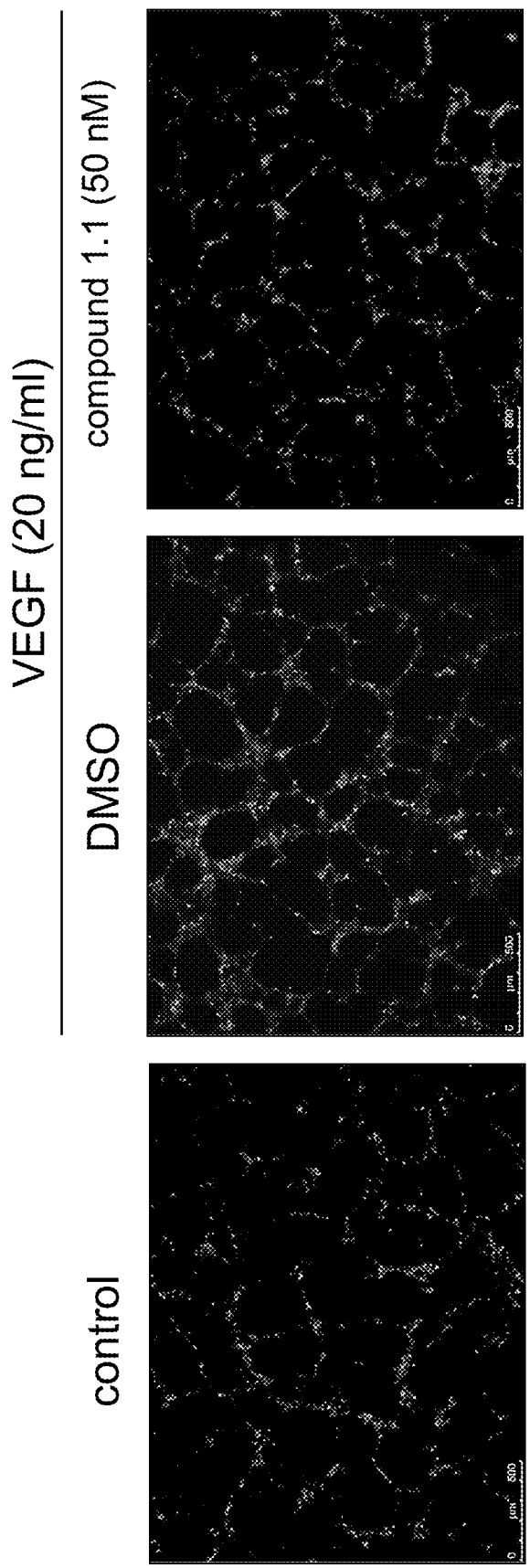
FIG. 26 is an image showing that compounds according to embodiments of the present invention (Compound 1.1 (SEQ ID NO: 2)) suppress tube formation in HRMEC.

FIG. 26 shows images of tube formation in the cells using fluorescence microscope, which can show that compound 1.1 (SEQ ID NO: 2) suppressed tube formation. Indeed, in ARPE-19 cells of human retinal pigment epithelium cells, compound 1.1 (SEQ ID NO: 2) suppressed expression of Nox-4, VEGF, VEGFR1, VEGFR2, Ang2, EPO, and EPOR proteins according to a concentration gradient thereof, and increased expression of Ang1 and Tie-2 was observed. As such, compound 1.1 (SEQ ID NO: 2) is effectively used for preventing, alleviating or treating ophthalmic indications such as diabetic retinopathy. In addition, by disrupting formation of signaling pathway complex of Myd88, the compound 1.1 (SEQ ID NO: 2) is effectively used for preventing, alleviating or treating geographic atrophy, wet-age-related macular disease (wet-AMD), dry-age-related macular disease (dry-AMD) and the like (*Cell* 149(4), (2012); 847-859).

Example 2.13

Effect on Diabetic Retinopathy

Streptozotocin (STZ) was administered at dose of 50 mg/kg to mice daily for 5 days, and a mouse model having induced diabetic retinopathy was obtained. The experimental group of the mouse model was injected with compound 1.1 (SEQ ID NO: 2), in an amount of 0.2 μg into one eye of the mouse, from the 20th day to 24th days from the administration, three times with two days of interval. After 50 days of administration, a DR sample that was not treated with compound 1.1 (SEQ ID NO: 2) and a DR sample treated with compound 1.1 (SEQ ID NO: 2) were collected.

Figure 27A:
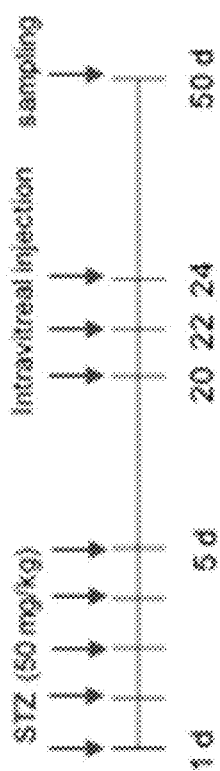
FIGS. 27A and 27B are images showing that compounds according to embodiments of the present invention suppress activated oxygen increased in a mice model with STZ-induced type 1 diabetic retinopathy.
Figure 27B:
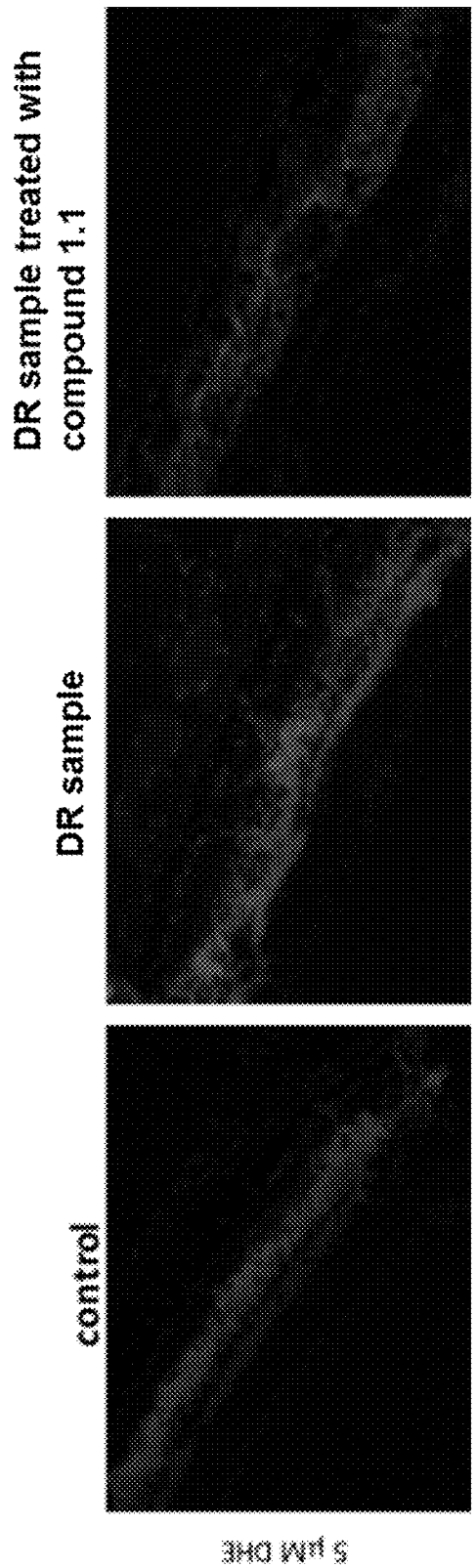

The collected retina tissues from each mouse group as described above were stained with 5 μM of dihydroethidium and active oxygen rates from each group were measured (FIG. 27B). The DR sample injected with compound 1.1 (SEQ ID NO: 2) showed reduced active oxygen rate as compared to the non-treated DR sample. Accordingly, compound 1.1 (SEQ ID NO: 2) of the present invention is effectively used for preventing, alleviating or treating ophthalmic indications such as diabetic retinopathy from the biological experiments using mice.

Example 2.14

Effect on Multiple Sclerosis

To confirm the effect of compound 1.1 (SEQ ID NO: 2) on multiple sclerosis, mice (10 weeks old, female) were sensitized with MOG35-55/CFU and PTX and an experimental autoimmune encephalomyelitis mouse model was obtained. Experimental methods were described in *Oncotarget*, Vol. 7 (2016), No. 13, 15382-15393, which is incorporated herein by reference.

Figure 28A:
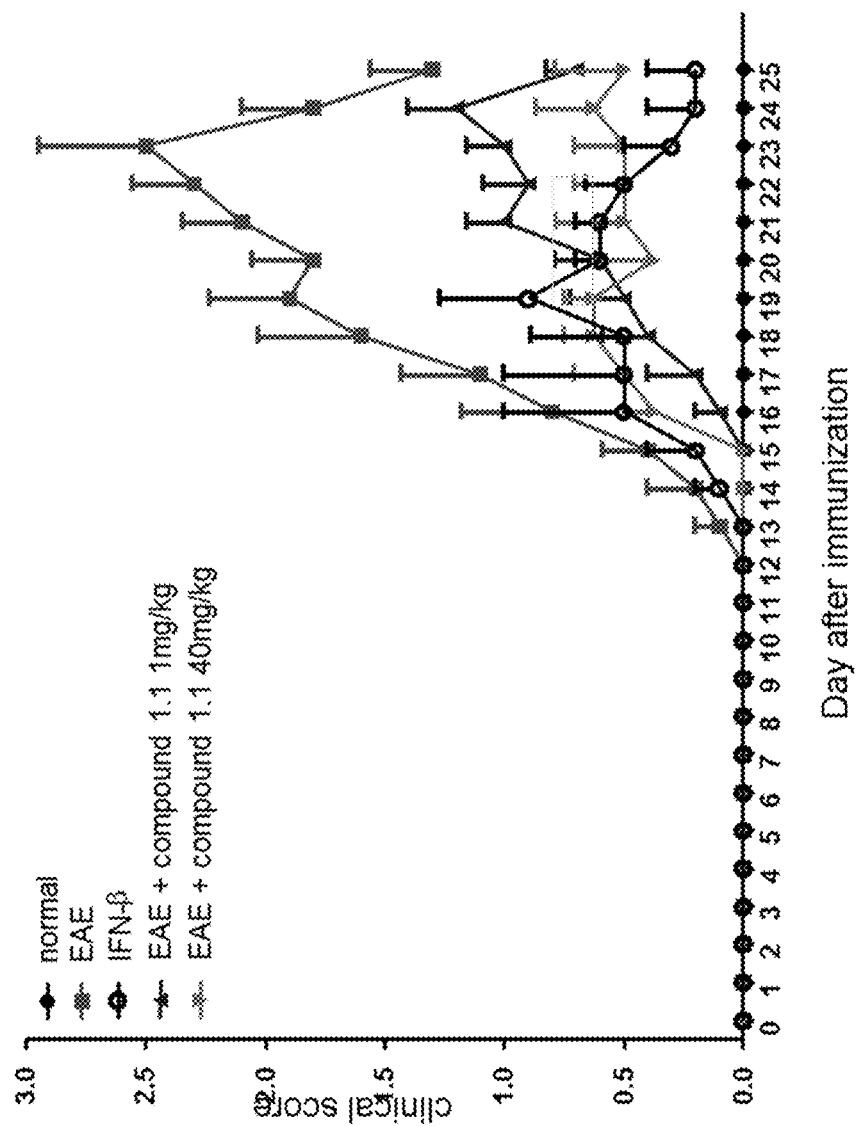
FIG. 28A is a graph showing that compounds according to embodiments of the present invention have a therapeutic effect in MOG-induced EAE mice. (Compound 1.1 (SEQ ID NO: 2)).

As shown in FIG. 28A, compound 1.1 (SEQ ID NO: 2) was hypodermically injected at dose of 1 mg/kg and 40 mg/kg for 25 days once in every other day. As reference group, 10000 unit of Interferon-beta was hypodermically injected for 25 days, once every other day. Clinical score were measured and presented. Consequently, compound 1.1 (SEQ ID NO: 2) showed to be effective in the treatment for multiple sclerosis at minimal dose of 1 mg/kg in comparison to the conventional drug interferon-beta currently used for multiple sclerosis treatment.

Figure 28B:
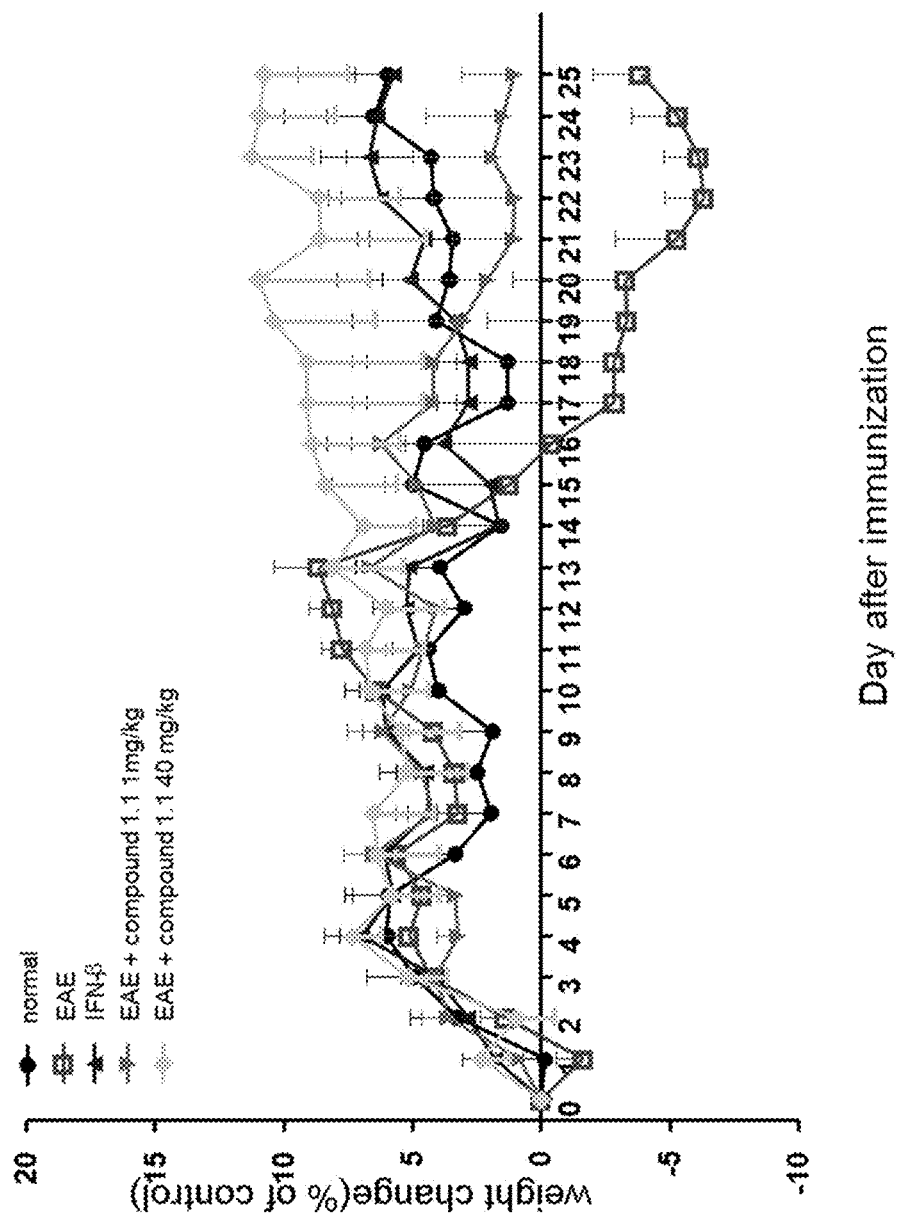
FIG. 28B is a graph showing that compounds according to embodiments of the present invention change the weight of MOG-induced EAE mice. (Compound 1.1 (SEQ ID NO: 2)).

In addition, when changes in body weights were measured from each experiment group, the group treated with compound 1.1 (SEQ ID NO: 2) did not have reduced weight as compared to the EAE disease model group (FIG. 28B). In other words, compound 1.1 (SEQ ID NO: 2), as compared to the current primary drug for treating multiple sclerosis, e.g. interferon-beta, exhibited the same or greater treatment effect and safety, and thus, is effectively used for preventing, alleviating or treating multiple sclerosis in experimental autoimmune encephalomyelitis model.

Example 2.15: Effect on Septicemia

To confirm the effects of compound 1.1 (SEQ ID NO: 2) on septicemia, 10 mice in each group (7-week old, male) were anesthetized, and thereafter, the appendicies were exposed by incision of abdomen. The lower portion of ileocecal valve of the exposed appendix was tied and a single hole was made by using a 22 gage syringe needle. The treated appendix was reinserted into the abdominal cavity, and grafted using thread to obtain a septicemia-induced mice model (cecal ligation and pucture model, CLP model). Experimental methods were described in EMBO Mol Med. (2015) Mar. 12; 7(5):577-92, which is incorporated herein by reference.

Figure 29:
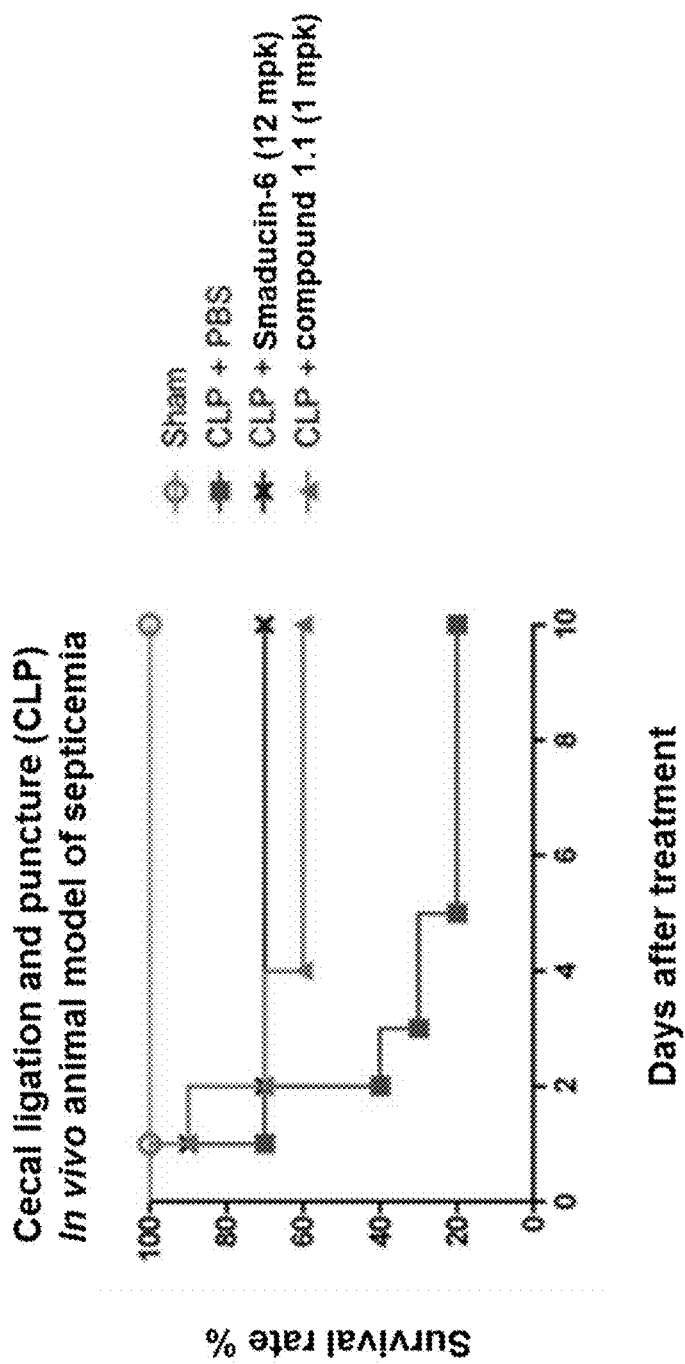
FIG. 29 is a graph showing that compounds according to embodiments of the present invention have a therapeutic effect in a Cecal ligation and puncture (CLP) model. (Compound 1.1 (SEQ ID NO: 2)).

Compound 1.1 (SEQ ID NO: 2) was hypodermically injected to the treated mice at dose of 1 mg/kg, after 2 hours from the CLP procedure, with 12 hour intervals, three times. As reference control, smaducin-6 was hypodermically injected at dose of 12 mg/kg as same method used for compound 1.1 (SEQ ID NO: 2). Survival rates of the mice from each group were measured (FIG. 29). Sham comparative group was not treated after incision of abdomen and anastomosis, CLP+PBS comparative group was treated with phosphate buffered saline (PBS) instead of drug compound after cecal ligation and puncture model was prepared. As a result, compound 1.1 (SEQ ID NO: 2) (1 mg/kg) was effective for the treatment of septicemia, which has not been previously treated with conventional drugs at low dosages compared to high dosages of smadudin-6 (e.g. 12 mg/kg), with 60% of survival rate. In other words, compound 1.1 (SEQ ID NO: 2) was effective on cecal ligation and puncture (CLP) model, indicating that compound 1.1 (SEQ ID NO: 2) is effectively used for preventing, alleviating or treating septicemia.

<Formulation 1> Granules

| Compound of Formula 1 (SEQ ID NO: 1) | 2 g |
| Lactose | 1 g |

The granules were prepared in accordance with the method known in the art.

<Formulation 2> Tablets

| Compound of Formula 1 (SEQ ID NO: 1) | 100 mg |
| Corn starch | 100 mg |
| Lactose | 100 mg |
| Stearic magnesium | 2 mg |

The tablets were prepared in accordance with the method known in the art.

<Formulation 3> Capsules

| Compound of Formula 1 (SEQ ID NO: 1) | 100 mg |
| Corn starch | 100 mg |
| Lactose | 100 mg |
| Stearic magnesium | 2 mg |

The capsules were prepared in accordance with the method known in the art.

<Formulation 4> Injections

| Compound of Formula 1 (SEQ ID NO: 1) | 100 mg |
| Mannitol | 180 mg |
| $Na_2HPO_4 \cdot 2H_2O$ | 26 mg |
| Distilled water | 2974 mg |

The injections were prepared in accordance with the method known in the art.

REFERENCES

1. *Toxicology and Applied Pharmacology* 279 (2014) 311-321
2. *International Immunopharmacology* 23 (2014) 294-303
3. *Seminars in Immunology* 26 (2014) 75-79
4. *Neurobiology of Aging* 22 (2001) 863-871
5. *J. Immunology* 175 (2005) 3463-3468
6. *Prot Natl Acad Sci.* 86 (1989) 6367-6371; J. Immunol. 143 (1989) 3949-3955; Nature 332 (1988) 83-85
7. *FASEB J.* 4 (1990) 2860-2867
8. *J. Immunol.* 147 (1991) 2777-2786
9. *Cell* 46(5) (1986) 705-16
10. *Annu Rev Immunol.* 16 (1998) 225
11. *Nature* 395 (1998) 297-300; Cell 93 (1998) 1231-1240
12. *Nature* 449 (2007), 361-365
13. *American Journal of Pathology,* 162(2), (2003)
14. *Nature Immunol.* 6, (2005), 507-514
15. *J Cell Physiol.* 196(2): (2003); 258-64)
16. *Nature Protocols,* 8(3), (2013) 627-637.
17. *The Journal of Clinical Investigation,* 124(11), (2014), 4976-4988.
18. *J. Virology,* 86(12), (2012), 6595-6604.
19. *J. Clin. Invest.,* 111 (2003), 1297-1308.
20. *Immunity,* 10 (1999), 39-49.
21. *Eur. J. Immunol.,* 36 (2006), 864-874.
22. *Immunity,* 25 (2006), 319-329.
23. *Cell* 118 (2004), 229-241.
24. *J. Immunol.* 179 (2007), 2690-2694.
25. *Oncotarget, Vol.* 7 (2016), No. 13, 15382-15393.
26. *Cell.* 149(4), (2012); 847-859.
27. *Nature Medicine,* 19(5), (2013), 595-602.
28. J. Immunol., 187 (2011), 1-14.
29. J. Inv. Derm., 132 (2012), 43-49.
30. Med. Inflamm., (2010), Article ID 928030
31. Hair The Transplant, 4 (2014), 4:1
32. Exp. Derm., 17 (2007), 12-19
33. DDT Dis. Mech. 5 (2009), e163-171
34. EMBO Mol Med. (2015) Mar. 12; 7(5):577-92
35. Expert opinion on emerging drugs (2015) 20(3):349-352
36. Cell. (2010) March 19; 140(6): 883-899
37. Progress in Retinal and Eye Research 37(2013) 68e89
38. P&T 41(2016), Jun no 6
39. Gut 56(2007):725-732.
40. World J Gastroenterol (2005); 11(16):2462-2466

All publications, including but not limited to patents and patent applications, cited in this specification are herein incorporated by reference as if each individual publication were specifically and individually indicated to be incorporated by reference herein as though fully set forth.

The invention claimed is:

1. A method for preventing, improving, or treating inflammatory bowel disease, the method comprising orally or rectally administering to a subject in need a compound represented by the following Formula 1, or a salt thereof:

[Formula 1]

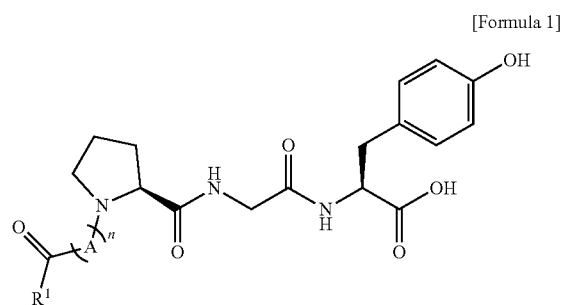

wherein:

n is 0, 1, or 2;

A is -a1-, which is an amino acid independently selected from the group consisting of alanine, (Ala, A), arginine (Arg, R), asparagine (Asn, N), aspartic acid (Asp, D), cysteine (Cys, C), glutamic acid (Glu, E), glutamine (Gln, Q), glycine (Gly, G), histidine (His, H), isoleucine (Ile, 1), leucine (Leu, L), lysine (Lys, K), methionine (Met, M), phenylalanine (Phe, F), proline (Pro, P), serine (Ser, S), threonine (Thr, T), tryptophan (Trp, W), tyrosine (Tyr, Y), and valine (Val, V), both terminal ends of the amino acid being coupled to a carbonyl group or an amine group by an amide bond;

$R^1$ is a straight chain or branched chain $C_{1-36}$ alkyl, a straight chain or branched chain $C_{2-36}$ alkenyl including at least one double bond, or a straight chain or branched chain $C_{2-36}$ alkynyl including at least one triple bond; and wherein a carbon atom of the carbonyl group attached to $R^1$ is directly bonded to a terminal nitrogen atom of -a1-, such that the terminal nitrogen atom forms an amide.

2. The method of claim 1, wherein the inflammatory bowel disease includes ulcerative colitis, Behcet's disease, or Crohn's disease.

3. The method of claim 1, wherein the compound inhibits formation of an inflammatory signal transduction complex mediated by MyD88, inhibits formation of an inflammatory signal transduction complex mediated by Pellino-1, inhibits formation of an inflammatory signal transduction complex mediated by Rip1, suppresses expression of at least one protein selected from the group consisting of G-CSF, IL-2, SCF, VEGF, CX3CL 1, IGFBP5, IGFBP6, IL-1α, IL-1β, IL-6, IL-9, MCP-1, MIP-3a, IL12p40/70, MIG, TNF-α, and VCAM-1, or suppresses activity of NF-κB.

4. A method for improving or treating inflammatory bowel disease, which comprises orally or rectally administering to a subject in need a composition containing a compound represented by the following Formula 1, or a salt thereof:

[Formula 1]

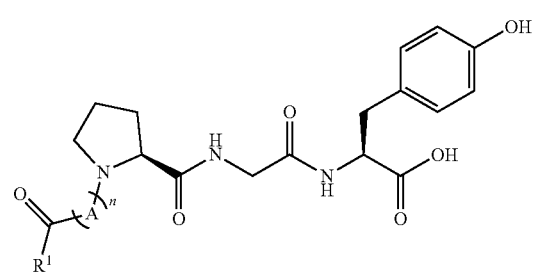

wherein:

n is 0, 1, or 2;

A is -a1-, which is an amino acid independently selected from the group consisting of alanine, (Ala, A), arginine (Arg, R), asparagine (Asn, N), aspartic acid (Asp, D), cysteine (Cys, C), glutamic acid (Glu, E), glutamine (Gln, Q), glycine (Gly, G), histidine (His, H), isoleucine (Ile, 1), leucine (Leu, L), lysine (Lys, K), methionine (Met, M), phenylalanine (Phe, F), proline (Pro, P), serine (Ser, S), threonine (Thr, T), tryptophan (Trp, W), tyrosine (Tyr, Y), and valine (Val, V), both terminal ends of the amino acid being coupled to a carbonyl group or an amine group by an amide bond;

$R^1$ is a straight chain or branched chain $C_{1-36}$ alkyl, a straight chain or branched chain $C_{2-36}$ alkenyl including at least one double bond, or a straight chain or branched chain $C_{2-36}$ alkynyl including at least one triple bond;

wherein a carbon atom of the carbonyl group attached to $R^1$ is directly bonded to a terminal nitrogen atom of -a1-, such that the terminal nitrogen atom forms an amide.

5. The method of claim 4, wherein the inflammatory bowel disease includes ulcerative colitis, Behcet's disease, or Crohn's disease.

6. A method for suppressing expression of inflammatory cytokines and/or chemokines, which comprises orally or rectally administering to a subject in need a compound represented by the following Formula 1, or a salt thereof:

[Formula 1]

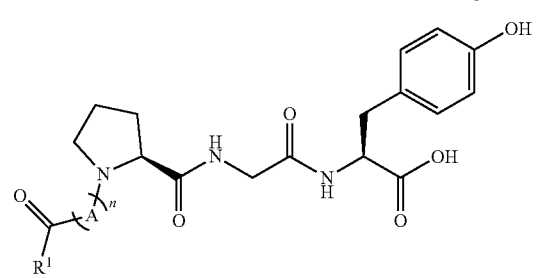

wherein:

n is 0, 1, or 2;

A is -a1-, which is an amino acid independently selected from the group consisting of alanine, (Ala, A), arginine (Arg, R), asparagine (Asn, N), aspartic acid (Asp, D), cysteine (Cys, C), glutamic acid (Glu, E), glutamine (Gln, Q), glycine (Gly, G), histidine (His, H), isoleucine (Ile, 1), leucine (Leu, L), lysine (Lys, K), methionine (Met, M), phenylalanine (Phe, F), proline (Pro, P), serine (Ser, S), threonine (Thr, T), tryptophan (Trp, W), tyrosine (Tyr, Y), and valine (Val, V), both terminal ends of the amino acid being coupled to a carbonyl group or an amine group by an amide bond;

$R^1$ is a straight chain or branched chain $C_{1-36}$ alkyl, a straight chain or branched chain $C_{2-36}$ alkenyl including at least one double bond, or a straight chain or branched chain $C_{2-36}$ alkynyl including at least one triple bond;

wherein a carbon atom of the carbonyl group attached to $R^1$ is directly bonded to a terminal nitrogen atom of -a1-, such that the terminal nitrogen atom forms an amide.

7. The method of claim 1, wherein $R^1$ is a $C_{5-17}$ alkyl, a $C_{5-17}$ alkenyl including at least one double bond, or a $C_{5-17}$ alkynyl including at least one triple bond.

8. The method of claim 7, wherein $R^1$ is n-pentadecyl.

9. The method of claim 4, wherein the inflammatory bowel disease involves formation of a Pellino-1 induced inflammatory signal transduction complex containing MyD88, RIP1, or both.

10. The method of claim 4, wherein $R^1$ is a $C_{5-17}$ alkyl, a $C_{5-17}$ alkenyl including at least one double bond, or a $C_{5-17}$ alkynyl including at least one triple bond.

11. The method of claim 10, wherein $R^1$ is n-pentadecyl.

12. The method of claim 6, wherein $R^1$ is a $C_{5-17}$ alkyl, a $C_{5-17}$ alkenyl including at least one double bond, or a $C_{5-17}$ alkynyl including at least one triple bond.

13. The method of claim 12, wherein $R^1$ is n-pentadecyl.

14. The method of claim 1, wherein the method comprises orally administering the compound represented by Formula 1 or salt thereof.

15. The method of claim 4, wherein the method comprises orally administering the compound represented by Formula 1 or salt thereof.

16. The method of claim 6, wherein the method comprises orally administering the compound represented by Formula 1 or salt thereof.

* * * * *

SEQUENCE LISTING

<160> NUMBER OF SEQ ID NOS: 17

<210> SEQ ID NO 1
<211> LENGTH: 5
<212> TYPE: PRT
<213> ORGANISM: Artificial Sequence
<220> FEATURE:
<223> OTHER INFORMATION: Formula 1 is synthesized.
<220> FEATURE:
<221> NAME/KEY: Standard_Amino_Acid
<222> LOCATION: (1)..(2)
<223> OTHER INFORMATION: X = Ala, Arg, Asn, Asp, Cys, Glu, Gln, Gly,
      His, Ile, Leu, Lys, Met, Phe, Pro, Ser, Thr, Trp, Tyr, or Val Any
      one or all of amino acids 1 to 2 can either be present or absent
<220> FEATURE:
<221> NAME/KEY: MOD_RES
<222> LOCATION: (1)..(1)
<223> OTHER INFORMATION: a straight chain or branched chain C2-37
      alkanoyl, a straight chain or branched chain C3-37 alkenoyl
      including at least one double bond, or a straight chain or
      branched chain C3-37 alkynoyl including at least one triple bond,
      on the N-terminus.

<400> SEQUENCE: 1

Xaa Xaa Pro Gly Tyr
1               5

<210> SEQ ID NO 2
<211> LENGTH: 4
<212> TYPE: PRT
<213> ORGANISM: Artificial Sequence
<220> FEATURE:
<223> OTHER INFORMATION: Formula A is synthesized.
<220> FEATURE:
<221> NAME/KEY: MOD_RES
<222> LOCATION: (1)..(1)
<223> OTHER INFORMATION: N-terminal straight chain C16 alkanoyl

<400> SEQUENCE: 2

Pro Pro Gly Tyr
1

<210> SEQ ID NO 3
<211> LENGTH: 4
<212> TYPE: PRT
<213> ORGANISM: Artificial Sequence
<220> FEATURE:
<223> OTHER INFORMATION: Formula C is synthesized.
<220> FEATURE:
<221> NAME/KEY: MOD_RES
<222> LOCATION: (1)..(1)
<223> OTHER INFORMATION: N-terminal straight chain C16 alkanoyl

<400> SEQUENCE: 3

Ala Pro Gly Tyr
1

<210> SEQ ID NO 4
<211> LENGTH: 4
<212> TYPE: PRT
<213> ORGANISM: Artificial Sequence
<220> FEATURE:
<223> OTHER INFORMATION: Formula D is synthesized.
<220> FEATURE:
<221> NAME/KEY: MOD_RES
<222> LOCATION: (1)..(1)
<223> OTHER INFORMATION: N-terminal straight chain C16 alkanoyl

<400> SEQUENCE: 4

Gly Pro Gly Tyr
1

```
<210> SEQ ID NO 5
<211> LENGTH: 4
<212> TYPE: PRT
<213> ORGANISM: Artificial Sequence
<220> FEATURE:
<223> OTHER INFORMATION: Formula E is synthesized.
<220> FEATURE:
<221> NAME/KEY: MOD_RES
<222> LOCATION: (1)..(1)
<223> OTHER INFORMATION: N-terminal linoleoyl

<400> SEQUENCE: 5

Gly Pro Gly Tyr
1

<210> SEQ ID NO 6
<211> LENGTH: 4
<212> TYPE: PRT
<213> ORGANISM: Artificial Sequence
<220> FEATURE:
<223> OTHER INFORMATION: Formula F is synthesized.
<220> FEATURE:
<221> NAME/KEY: MOD_RES
<222> LOCATION: (1)..(1)
<223> OTHER INFORMATION: N-terminal straight chain C16 alkanoyl

<400> SEQUENCE: 6

Phe Pro Gly Tyr
1

<210> SEQ ID NO 7
<211> LENGTH: 4
<212> TYPE: PRT
<213> ORGANISM: Artificial Sequence
<220> FEATURE:
<223> OTHER INFORMATION: Formula G is synthesized.
<220> FEATURE:
<221> NAME/KEY: MOD_RES
<222> LOCATION: (1)..(1)
<223> OTHER INFORMATION: N-terminal straight chain C6 alkanoyl

<400> SEQUENCE: 7

Pro Pro Gly Tyr
1

<210> SEQ ID NO 8
<211> LENGTH: 4
<212> TYPE: PRT
<213> ORGANISM: Artificial Sequence
<220> FEATURE:
<223> OTHER INFORMATION: Formula H is synthesized.
<220> FEATURE:
<221> NAME/KEY: MOD_RES
<222> LOCATION: (1)..(1)
<223> OTHER INFORMATION: N-terminal straight chain C8 alkanoyl

<400> SEQUENCE: 8

Pro Pro Gly Tyr
1

<210> SEQ ID NO 9
<211> LENGTH: 4
<212> TYPE: PRT
<213> ORGANISM: Artificial Sequence
<220> FEATURE:
<223> OTHER INFORMATION: Formula I is synthesized.
<220> FEATURE:
<221> NAME/KEY: MOD_RES
<222> LOCATION: (1)..(1)
```

<223> OTHER INFORMATION: N-terminal straight chain C10 alkanoyl

<400> SEQUENCE: 9

Pro Pro Gly Tyr
1

<210> SEQ ID NO 10
<211> LENGTH: 4
<212> TYPE: PRT
<213> ORGANISM: Artificial Sequence
<220> FEATURE:
<223> OTHER INFORMATION: Formula J is synthesized.
<220> FEATURE:
<221> NAME/KEY: MOD_RES
<222> LOCATION: (1)..(1)
<223> OTHER INFORMATION: N-terminal straight chain C18 alkanoyl

<400> SEQUENCE: 10

Pro Pro Gly Tyr
1

<210> SEQ ID NO 11
<211> LENGTH: 4
<212> TYPE: PRT
<213> ORGANISM: Artificial Sequence
<220> FEATURE:
<223> OTHER INFORMATION: Formula K is synthesized.
<220> FEATURE:
<221> NAME/KEY: MOD_RES
<222> LOCATION: (1)..(1)
<223> OTHER INFORMATION: N-terminal hex-5-enoyl

<400> SEQUENCE: 11

Pro Pro Gly Tyr
1

<210> SEQ ID NO 12
<211> LENGTH: 4
<212> TYPE: PRT
<213> ORGANISM: Artificial Sequence
<220> FEATURE:
<223> OTHER INFORMATION: Formula L is synthesized.
<220> FEATURE:
<221> NAME/KEY: MOD_RES
<222> LOCATION: (1)..(1)
<223> OTHER INFORMATION: N-terminal oleoyl

<400> SEQUENCE: 12

Pro Pro Gly Tyr
1

<210> SEQ ID NO 13
<211> LENGTH: 4
<212> TYPE: PRT
<213> ORGANISM: Artificial Sequence
<220> FEATURE:
<223> OTHER INFORMATION: Formula M is synthesized.
<220> FEATURE:
<221> NAME/KEY: MOD_RES
<222> LOCATION: (1)..(1)
<223> OTHER INFORMATION: N-terminal linoleoyl

<400> SEQUENCE: 13

Pro Pro Gly Tyr
1

<210> SEQ ID NO 14
<211> LENGTH: 5
<212> TYPE: PRT

```
<213> ORGANISM: Artificial Sequence
<220> FEATURE:
<223> OTHER INFORMATION: Formula N is synthesized.
<220> FEATURE:
<221> NAME/KEY: MOD_RES
<222> LOCATION: (1)..(1)
<223> OTHER INFORMATION: N-terminal straight chain C16 alkanoyl

<400> SEQUENCE: 14

Val Pro Pro Gly Tyr
1               5

<210> SEQ ID NO 15
<211> LENGTH: 5
<212> TYPE: PRT
<213> ORGANISM: Artificial Sequence
<220> FEATURE:
<223> OTHER INFORMATION: Formula O is synthesized.
<220> FEATURE:
<221> NAME/KEY: MOD_RES
<222> LOCATION: (1)..(1)
<223> OTHER INFORMATION: N-terminal straight chain C10 alkanoyl

<400> SEQUENCE: 15

Val Pro Pro Gly Tyr
1               5

<210> SEQ ID NO 16
<211> LENGTH: 4
<212> TYPE: PRT
<213> ORGANISM: Artificial Sequence
<220> FEATURE:
<223> OTHER INFORMATION: Synthetic

<400> SEQUENCE: 16

Pro Pro Gly Tyr
1

<210> SEQ ID NO 17
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: Standard_Amino_Acid
<222> LOCATION: (1)..(2)
<223> OTHER INFORMATION: Any one or all of amino acids 1 to 2 can either
      be present or absent
<220> FEATURE:
<221> NAME/KEY: MOD_RES
<222> LOCATION: (1)..(1)
<223> OTHER INFORMATION: N-terminal straight chain or branched chain
      C2-37 alkanoyl

<400> SEQUENCE: 17

Pro Pro Pro Gly Tyr
1               5
```